US012760056B2

(12) United States Patent
Michida et al.

(10) Patent No.: US 12,760,056 B2
(45) Date of Patent: Oct. 13, 2026

(54) METHOD FOR PRODUCING BICYCLIC PHOSPHORAMIDITE

(71) Applicant: DAIICHI SANKYO COMPANY, LIMITED, Tokyo (JP)

(72) Inventors: Makoto Michida, Kawasaki (JP); Kazutoshi Ukai, Shinagawa-ku (JP); Yuzo Abe, Chigasaki (JP); Moe Matsumoto, Hiratsuka (JP); Makoto Yamaoka, Hiratsuka (JP); Kei Kurahashi, Hiratsuka (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 828 days.

(21) Appl. No.: 17/769,483

(22) PCT Filed: Oct. 16, 2020

(86) PCT No.: PCT/JP2020/039050

§ 371 (c)(1),
(2) Date: Apr. 15, 2022

(87) PCT Pub. No.: WO2021/075538

PCT Pub. Date: Apr. 22, 2021

(65) Prior Publication Data

US 2023/0348522 A1 Nov. 2, 2023

(30) Foreign Application Priority Data

Oct. 18, 2019 (JP) ................................ 2019-191053

(51) Int. Cl.
*C07H 19/06* (2006.01)
*C07D 493/08* (2006.01)
*C07H 1/00* (2006.01)
*C07H 3/10* (2006.01)
*C07H 19/16* (2006.01)
*C07H 21/00* (2006.01)

(52) U.S. Cl.
CPC .......... *C07H 19/06* (2013.01); *C07D 493/08* (2013.01); *C07H 1/00* (2013.01); *C07H 3/10* (2013.01); *C07H 19/16* (2013.01); *C07H 21/00* (2013.01); *C07B 2200/13* (2013.01)

(58) Field of Classification Search
None
See application file for complete search history.

(56) References Cited

U.S. PATENT DOCUMENTS 6,525,191 B1 2/2003 Ramasamy
7,335,765 B2 * 2/2008 Kaneko .................. A61P 31/12 536/28.1
2002/0147332 A1 10/2002 Kaneko et al.
2006/0166908 A1 7/2006 Imanishi et al.
2007/0082861 A1 4/2007 Matsuo et al.
2020/0407394 A1 12/2020 Koizumi et al.

FOREIGN PATENT DOCUMENTS

EP 1152009 A1 11/2001
JP 2001-247596 A 9/2001
JP 2002-322192 A 11/2002
JP 2010-241836 A 10/2010
WO 98/39352 A1 9/1998
WO 99/14226 A2 3/1999
WO 2000/47599 A1 8/2000
WO 03/006475 A2 1/2003
WO 2004/048570 A1 6/2004
WO 2013/052523 A1 4/2013
WO 2013/191129 A1 12/2013
WO 2018/049534 A1 3/2018
WO 2019/172286 A1 9/2019
WO 2019/224172 A1 11/2019

OTHER PUBLICATIONS

Greene, T.W., et al., "Protective Groups in Organic Synthesis," Protective Groups in Organic Synthesis, Third Edition, Apr. 9, 1999, entire document.

International Search Report mailed Dec. 22, 2020, issued in corresponding Japanese Patent Application No. PCT/JP2020/039050, filed Oct. 16, 2020, 5 pages.

Morita et al., "2'-0,4'-C-Ethylene-Bridged Nucleic Acids (ENA): Highly Nuclease-Resistant and Thermodynamically Stable Oligonucleotides for Antisense Drug", Bioorganic & Medicinal Chemistry Letters, (2002), 12:73-76.

Morita et al., "Synthesis and Properties of 2'-0,4'-C-Ethylene-Bridged Nucleic Acids (ENA) as Effective Antisense Oligonucleotides", Bioorganic & Medicinal Chemistry, (2003), 11:2211-2226.

Bodepudi, V. et al., "Synthesis of 2'-Deoxy-7,8-dihydro-8-oxoguanosine and 2'-Deoxy-7,8-dihydro-8-oxoadenosine and Their Incorporation into Oligomeric DNA", Chem. Res. Toxicol., 1992, vol. 5, pp. 608-617.

Caner J. et al., "15N Double-Labeled Guanosine from Inosine through Ring-Opening—Ring-Closing and One-Pot Pd-Catalyzed C—O and C—N Cross-Coupling Reactions", The Journal of Organic Chemistry, 2010, vol. 75, pp. 4880-4883, American Chemical Society.

Koizumi, M. et al., "Improvement of single nucleotide polymorphism genotyping by allele-specific PCR using primers modified with an ENA residue", Analytical Biochemistry, 2005, vol. 340, pp. 287-294, Elsevier Inc.

(Continued)

*Primary Examiner* — Patrick T Lewis
(74) *Attorney, Agent, or Firm* — Christensen O'Connor Johnson Kindness PLLC

(57) ABSTRACT

The present invention provides a crystalline 2,4-bridged common intermediate useful for producing a plurality of ENA monomers, a method for stereoselectively producing the intermediate, and a method for efficiently producing ENA monomers using the intermediate.

18 Claims, No Drawings

Specification includes a Sequence Listing.

(56) References Cited

OTHER PUBLICATIONS

Mitsuoka, Y. et al., "Triazole- and Tetrazole-Bridged Nucleic Acids: Synthesis, Duplex Stability, Nuclease Resistance, and in Vitro and in Vivo Antisense Potency", The Journal of Organic Chemistry, 2017, vol. 82, pp. 12-24, American Chemical Society.

Supplementary Partial European Search Report mailed Nov. 11, 2023, issued in corresponding Application No. EP20877640.1, filed Oct. 16, 2020, 16 pages.

Nielsen, P., and J. Wengel, "Synthesis and chemoselective activation of phenyl 3,5-di-O-benzyl-2-O,4-C-methylene-1-thio-β-D•ribofuranoside: a key synthon towards α-LNA", Chemical Communications, Royal Society of Chemistry, UK, Jan. 1, 1998.

Office Action mailed Jan. 13, 2024, issued in corresponding Chinese Application No. 202080072429.5, filed Oct. 16, 2020, 18 pages.

* cited by examiner

SEQUENCE LISTING

```
<160> NUMBER OF SEQ ID NOS: 31

<210> SEQ ID NO 1
<211> LENGTH: 18
<212> TYPE: DNA
<213> ORGANISM: Artificial Sequence
<220> FEATURE:
<223> OTHER INFORMATION: DMD A001

<400> SEQUENCE: 1

cagttugccg ctgcccaa                                                 18


<210> SEQ ID NO 2
<211> LENGTH: 18
<212> TYPE: DNA
<213> ORGANISM: Artificial Sequence
<220> FEATURE:
<223> OTHER INFORMATION: DMD A002

<400> SEQUENCE: 2

tgttctgaca acagtttg                                                 18


<210> SEQ ID NO 3
<211> LENGTH: 18
<212> TYPE: DNA
<213> ORGANISM: Artificial Sequence
<220> FEATURE:
<223> OTHER INFORMATION: DMD A003

<400> SEQUENCE: 3

cgctgcccaa tgccaucc                                                 18
```

<210> SEQ ID NO 4
<211> LENGTH: 18
<212> TYPE: DNA
<213> ORGANISM: Artificial Sequence
<220> FEATURE:
<223> OTHER INFORMATION: DMD AO04

<400> SEQUENCE: 4
cataatgaaa acgccgcc 18

<210> SEQ ID NO 5
<211> LENGTH: 18
<212> TYPE: DNA
<213> ORGANISM: Artificial Sequence
<220> FEATURE:
<223> OTHER INFORMATION: DMD AO05

<400> SEQUENCE: 5
tucccaatuc tcaggaat 18

<210> SEQ ID NO 6
<211> LENGTH: 18
<212> TYPE: DNA
<213> ORGANISM: Artificial Sequence
<220> FEATURE:
<223> OTHER INFORMATION: DMD AO06

<400> SEQUENCE: 6
ccautugtau ttagcatg 18

<210> SEQ ID NO 7
<211> LENGTH: 18
<212> TYPE: DNA
<213> ORGANISM: Artificial Sequence
<220> FEATURE:
<223> OTHER INFORMATION: DMD AO07

<400> SEQUENCE: 7
ggctgcttug ccctcagc 18

<210> SEQ ID NO 8
<211> LENGTH: 17
<212> TYPE: DNA
<213> ORGANISM: Artificial Sequence
<220> FEATURE:
<223> OTHER INFORMATION: DMD AO08

<400> SEQUENCE: 8
gctaggtcag gtgcttu 17

<210> SEQ ID NO 9
<211> LENGTH: 18
<212> TYPE: DNA
<213> ORGANISM: Artificial Sequence
<220> FEATURE:
<223> OTHER INFORMATION: DMD AO09

<400> SEQUENCE: 9
accgcctucc actcagag 18

<210> SEQ ID NO 10
<211> LENGTH: 18
<212> TYPE: DNA
<213> ORGANISM: Artificial Sequence
<220> FEATURE:

-continued

<223> OTHER INFORMATION: DMD AO10

<400> SEQUENCE: 10
ggcatuucua guutggag 18

<210> SEQ ID NO 11
<211> LENGTH: 18
<212> TYPE: DNA
<213> ORGANISM: Artificial Sequence
<220> FEATURE:
<223> OTHER INFORMATION: DMD AO11

<400> SEQUENCE: 11
ggcattucta guttggag 18

<210> SEQ ID NO 12
<211> LENGTH: 18
<212> TYPE: DNA
<213> ORGANISM: Artificial Sequence
<220> FEATURE:
<223> OTHER INFORMATION: DMD AO12

<400> SEQUENCE: 12
agtutggaga tggcagtt 18

<210> SEQ ID NO 13
<211> LENGTH: 18
<212> TYPE: DNA
<213> ORGANISM: Artificial Sequence
<220> FEATURE:
<223> OTHER INFORMATION: DMD AO13

<400> SEQUENCE: 13
ctcctuccat gactcaag 18

<210> SEQ ID NO 14
<211> LENGTH: 18
<212> TYPE: DNA
<213> ORGANISM: Artificial Sequence
<220> FEATURE:
<223> OTHER INFORMATION: DMD AO14

<400> SEQUENCE: 14
ctgaaggtgt tcttgtac 18

<210> SEQ ID NO 15
<211> LENGTH: 18
<212> TYPE: DNA
<213> ORGANISM: Artificial Sequence
<220> FEATURE:
<223> OTHER INFORMATION: DMD AO15

<400> SEQUENCE: 15
ttccagccat tgtgttga 18

<210> SEQ ID NO 16
<211> LENGTH: 15
<212> TYPE: DNA
<213> ORGANISM: Artificial Sequence
<220> FEATURE:
<223> OTHER INFORMATION: GSD AO01

<400> SEQUENCE: 16
aauccgatgg cgaag 15

<210> SEQ ID NO 17
<211> LENGTH: 15
<212> TYPE: DNA
<213> ORGANISM: Artificial Sequence
<220> FEATURE:
<223> OTHER INFORMATION: GSD AO02

<400> SEQUENCE: 17
auccgatggc gaagc 15

<210> SEQ ID NO 18
<211> LENGTH: 15
<212> TYPE: DNA
<213> ORGANISM: Artificial Sequence
<220> FEATURE:
<223> OTHER INFORMATION: GSD AO03

<400> SEQUENCE: 18
uccgatggcg aagcu 15

<210> SEQ ID NO 19
<211> LENGTH: 16
<212> TYPE: DNA
<213> ORGANISM: Artificial Sequence
<220> FEATURE:
<223> OTHER INFORMATION: GSD AO04

<400> SEQUENCE: 19
aaauccgatg gcgaag 16

<210> SEQ ID NO 20
<211> LENGTH: 16
<212> TYPE: DNA
<213> ORGANISM: Artificial Sequence
<220> FEATURE:
<223> OTHER INFORMATION: GSD AO05

<400> SEQUENCE: 20
aauccgatgg cgaagc 16

<210> SEQ ID NO 21
<211> LENGTH: 16
<212> TYPE: DNA
<213> ORGANISM: Artificial Sequence
<220> FEATURE:
<223> OTHER INFORMATION: GSD AO06

<400> SEQUENCE: 21
auccgatggc gaagcu 16

<210> SEQ ID NO 22
<211> LENGTH: 15
<212> TYPE: DNA
<213> ORGANISM: Artificial Sequence
<220> FEATURE:
<223> OTHER INFORMATION: GSD AO07

<400> SEQUENCE: 22
aauccgaugg cgaag 15

<210> SEQ ID NO 23
<211> LENGTH: 15
<212> TYPE: DNA
<213> ORGANISM: Artificial Sequence
<220> FEATURE:
<223> OTHER INFORMATION: GSD AO08

<400> SEQUENCE: 23
auccgauggc gaagc 15

<210> SEQ ID NO 24
<211> LENGTH: 15
<212> TYPE: DNA
<213> ORGANISM: Artificial Sequence
<220> FEATURE:
<223> OTHER INFORMATION: GSD AO09

<400> SEQUENCE: 24
uccgauggcg aagcu 15

<210> SEQ ID NO 25
<211> LENGTH: 16
<212> TYPE: DNA
<213> ORGANISM: Artificial Sequence
<220> FEATURE:
<223> OTHER INFORMATION: GSD AO10

<400> SEQUENCE: 25
aaauccgaug gcgaag 16

<210> SEQ ID NO 26
<211> LENGTH: 16
<212> TYPE: DNA
<213> ORGANISM: Artificial Sequence
<220> FEATURE:
<223> OTHER INFORMATION: GSD AO11

<400> SEQUENCE: 26
aauccgaugg cgaagc 16

<210> SEQ ID NO 27
<211> LENGTH: 16
<212> TYPE: DNA
<213> ORGANISM: Artificial Sequence
<220> FEATURE:
<223> OTHER INFORMATION: GSD AO12

<400> SEQUENCE: 27
auccgauggc gaagcu 16

<210> SEQ ID NO 28
<211> LENGTH: 15
<212> TYPE: DNA
<213> ORGANISM: Artificial Sequence
<220> FEATURE:
<223> OTHER INFORMATION: GSD AO13

<400> SEQUENCE: 28
aauccgaugg cgaag 15

<210> SEQ ID NO 29
<211> LENGTH: 15
<212> TYPE: DNA
<213> ORGANISM: Artificial Sequence
<220> FEATURE:
<223> OTHER INFORMATION: GSD AO14

<400> SEQUENCE: 29
auccgauggc gaagc 15

<210> SEQ ID NO 30
<211> LENGTH: 16

-continued

```
<212> TYPE: DNA
<213> ORGANISM: Artificial Sequence
<220> FEATURE:
<223> OTHER INFORMATION: GSD A015

<400> SEQUENCE: 30

aaauccgaug gcgaag                                                    16


<210> SEQ ID NO 31
<211> LENGTH: 16
<212> TYPE: DNA
<213> ORGANISM: Artificial Sequence
<220> FEATURE:
<223> OTHER INFORMATION: GSD A016

<400> SEQUENCE: 31

aauccgaugg cgaagc                                                    16
```

METHOD FOR PRODUCING BICYCLIC PHOSPHORAMIDITE

CROSS REFERENCE TO RELATED APPLICATIONS

This application is the U.S. national phase of PCT/JP2020/039050, filed on Oct. 16, 2020, which claims priority to Japanese Application No. 2019-191053, filed on Oct. 18, 2019, each expressly incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 1660-P107USPNP_Seq_List_FINAL_20220310_ST25.txt. The text file is 5901 bytes; was created on Mar. 10, 2022; and is being submitted via Patent Center.

TECHNICAL FIELD

The present invention relates to a new crystalline common intermediate for producing a plurality of ENA monomers, including a pyrimidine base or a purine base such as A, G, T, and C, which serve as starting materials for oligonucleotides containing 2'-O,4'-C-ethylene-bridged nucleic acid (ENA), a method for stereoselectively synthesizing β-adducts in glycosylation using the intermediate, a method for producing the production intermediate, and a method for producing ENA monomers using the production intermediate.

BACKGROUND ART

ENA monomers are important compounds for producing modified nucleic acid drugs/diagnostic agents.

The important steps in ENA production are a 2,4-crosslinking reaction and a glycosylation reaction for forming the basic skeleton.

Generally, it is known that, in the case where an acyloxy group is present at the 2-position in a glycosylation reaction, a β-nucleoside is obtained by controlling the configuration by the neighboring group effect (see Patent Literature 1), whereas in the case where no acyloxy group is present at the 2-position, such as in a 2,4-crosslinked form and a 2-deoxy form, an α-nucleoside is preferentially obtained (see Patent Literature 2).

Therefore, when producing a β-ENA, a method of introducing the base before 2,4-ethylenoxylation while an acyloxy group is present at the 2-position is used (see Patent Literature 3 and 4, and Non Patent Literature 1 and 2).

However, such conventional methods have not been industrially satisfactory production methods, because column purification is required due to most of the intermediates, including the common intermediate (compound having a hydroxyl group or an acetyloxy group at the 2-position and a protected —O-ethylene group at the 5-position) before 2,4-crosslinking and glycosylation, being oily compounds, and the process from the common intermediate to each ENA monomer is long (see Non Patent Literature 2).

CITATION LIST

Patent Literature

Patent Literature 1: International Publication No. WO 98/39352

Patent Literature 2: International Publication No. WO 99/14226

Patent Literature 3: International Publication No. WO 00/47599

Patent Literature 4: International Publication No. WO 2013/191129

Non Patent Literature

Non Patent Literature 1: Bioorganic & Medicinal Chemistry Letters 12 (2002) 73-76

Non Patent Literature 2: Bioorganic & Medicinal Chemistry Letters 11 (2003) 2211-2226

SUMMARY OF INVENTION

Technical Problem

It is an object of the present invention to provide a crystalline 2,4-bridged common intermediate useful for producing ENA monomers, a method for stereoselectively producing the intermediate, and a method for efficiently producing ENA monomers using the intermediate.

Solution to Problem

As a result of dedicated studies on methods for efficiently producing ENA monomers, the inventors have found a new crystalline 2,4-bridged common intermediate, a method for producing the common intermediate, and a method for producing ENA monomers using the common intermediate, thereby accomplishing the present invention. The common intermediate is crystalline and can be purified by crystallization, and is therefore suitable for industrial production. Since the method for producing the common intermediate uses easily available and inexpensive starting materials and a plurality of steps are performed without isolation, the common intermediate can be obtained in fewer steps with high yield. Further, use of the common intermediate enables a 2,4-bridged skeleton to be constructed before the glycosylation step, to reduce the steps after base introduction and improve the yield, so that a plurality of ENA monomers can be separately produced efficiently. Further, the hydroxyl group at the 1-position is substituted with an iodine atom or a bromine atom in glycosylation using the intermediate, thereby enabling β-products to be selectively produced by controlling the stereochemistry even without the neighboring group effect of the acyl group at the 2-position. In the amidite-formation, which is the final step in ENA monomer production, use of a specific activator and a specific drying agent can reduce the equivalents of the amidite reagent, thereby enabling ENA monomers to be produced efficiently.

That is, the present invention includes the following aspects.

(1) A compound represented by formula (I):

[Formula 1]

(I)

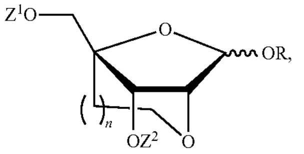

wherein $Z^1$ and $Z^2$ are identical or different and each represent a protective group for a hydroxy group, R represents a hydrogen atom or an aliphatic acyl group, and n represents an integer of 0 to 4;

(2) the compound according to (1), wherein R represents a hydrogen atom or an acetyl group;

(3) the compound according to (1) or (2), wherein $Z^1$ and $Z^2$ are identical or different and each represent an aliphatic acyl group, an aromatic acyl group, a methyl group substituted with 1 to 3 aryl groups, a methyl group substituted with 1 to 3 aryl groups in which each aryl ring is substituted with a lower alkyl, lower alkoxy, halogen, or cyano group, or a silyl group;

(4) the compound according to (1) or (2), wherein $Z^1$ and $Z^2$ are identical or different and each represent a benzyl group, a p-methoxybenzyl group, a t-butyldiphenylsilyl group, or a t-butyldimethylsilyl group;

(5) the compound according to (1) or (2), wherein $Z^1$ and $Z^2$ each represent a benzyl group;

(6) the compound according to any one of (1) to (5), wherein n is 1;

(7) a compound represented by formula (I'):

[Formula 2]

(I')

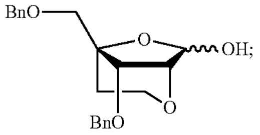

(8) a compound represented by formula (I"):

[Formula 3]

(I")

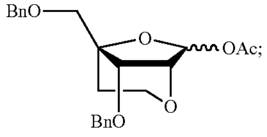

(9a) a method for producing a compound represented by formula (III):

[Formula 4]

(III)

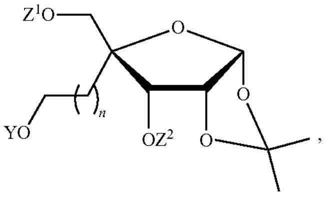

wherein $Z^1$ and $Z^2$ are identical or different and each represent a protective group for a hydroxy group, Y represents a methyl group substituted with 1 to 3 aryl groups, a methyl group substituted with 1 to 3 aryl groups in which each aryl ring is substituted with a lower alkyl, lower alkoxy, halogen, or cyano group, a lower alkoxymethyl group, a tetrahydropyranyl group, or a silyl group, and n represents an integer of 0 to 4, the method comprising: (i) a step of protecting the primary hydroxyl group of a compound represented by formula (XXIX):

[Formula 5]

(XXIX)

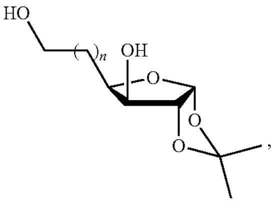

wherein n represents an integer of 0 to 4; (ii) a step of oxidizing the hydroxyl group of the compound represented by formula (XXX) obtained in step (i):

[Formula 6]

(XXX)

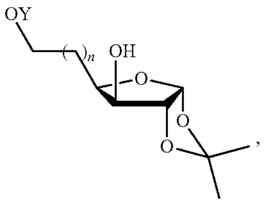

wherein Y and n have the same meanings as above; (iii) a step of stereoselectively hydroxymethylating the compound represented by formula (XXXI) obtained in step (ii):

[Formula 7]

(XXXI)

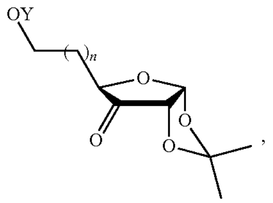

wherein Y and n have the same meanings as above, at the 4-position; (iv) a step of reducing the carbonyl group at the 3-position of the compound represented by formula (XXXII) obtained in step (iii):

[Formula 8]

(XXXII)

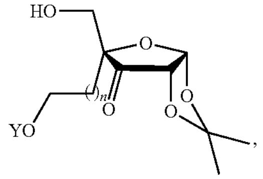

wherein Y and n have the same meanings as above; and (v) a step of protecting the hydroxyl groups of the compound represented by formula (XXXIII) obtained in step (iv):

[Formula 9]

(XXXIII)

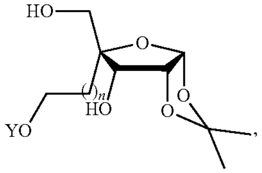

wherein Y and n have the same meanings as above;

(10a) the method according to (9a), wherein $Z^1$ and $Z^2$ are identical or different and each represent an aliphatic acyl group, an aromatic acyl group, a methyl group substituted with 1 to 3 aryl groups, a methyl group substituted with 1 to 3 aryl groups in which each aryl ring is substituted with a lower alkyl, lower alkoxy, halogen, or cyano group, or a silyl group;

(11a) the method according to (9a), wherein $Z^1$ and $Z^2$ are identical or different and each represent a benzyl group, a p-methoxybenzyl group, a t-butyldiphenylsilyl group, or a t-butyldimethylsilyl group;

(12a) the method according to (9a), wherein $Z^1$ and $Z^2$ each represent a benzyl group;

(13a) the method according to any one of (9a) to (12a), wherein Y represents a t-butyldiphenylsilyl group, a t-butyldimethylsilyl group, a tetrahydropyran-2-yl group, or a trityl group;

(14a) the method according to any one of (9a) to (12a), wherein Y represents a trityl group;

(15a) the method according to any one of (9a) to (14a), wherein n is 1;

(16a) the method according to any one of (9a) to (15a), wherein the organic layer of the solution containing the target compound after reaction in each of steps (i) to (v) is washed with water, and the organic layer obtained is used in the subsequent step, as it is;

(9) a method for producing a compound represented by formula (II):

[Formula 10]

(II)

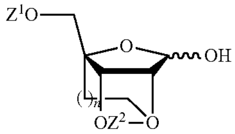

wherein $Z^1$ and $Z^2$ are identical or different and each represent a protective group for a hydroxy group, and n represents an integer of 0 to 4, the method comprising:

(i) a step of solvolyzing the acetal moiety of a compound represented by formula (III):

[Formula 11]

(III)

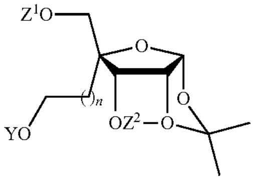

wherein $Z^1$, $Z^2$, and n have the same meanings as above, and Y represents a methyl group substituted with 1 to 3 aryl groups, a methyl group substituted with 1 to 3 aryl groups in which each aryl ring is substituted with a lower alkyl, lower alkoxy, halogen, or cyano group, a lower alkoxymethyl group, a tetrahydropyranyl group, or a silyl group, in a lower alkyl alcohol solvent in the presence of an acid catalyst, to deprotect Y;

(ii) a step of cyclizing the diol moiety of the compound represented by formula (IV) obtained in step (i):

[Formula 12]

(IV)

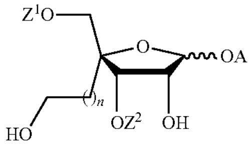

wherein $Z^1$, $Z^2$, and n have the same meanings as above, and A represents a lower alkyl group; and (iii) a step of hydrolyzing the anomer position of the compound represented by formula (V) obtained in step (ii):

[Formula 13]

(V)

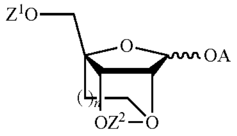

wherein $Z^1$, $Z^2$, A and n have the same meanings as above;

(10) the method according to (9), wherein $Z^1$ and $Z^2$ are identical or different and each represent an aliphatic acyl group, an aromatic acyl group, a methyl group substituted with 1 to 3 aryl groups, a methyl group substituted with 1 to 3 aryl groups in which each aryl ring is substituted with a lower alkyl, lower alkoxy, halogen, or cyano group, or a silyl group;

(11) the method according to (9), wherein $Z^1$ and $Z^2$ are identical or different and each represent a benzyl group, a p-methoxybenzyl group, a t-butyldiphenylsilyl group, or a t-butyldimethylsilyl group;

(12) the method according to (9), wherein $Z^1$ and $Z^2$ each represent a benzyl group;

(13) the method according to any one of (9) to (12), wherein A represents a methyl group, an ethyl group, or a propyl group;

(14) the method according to any one of (9) to (12), wherein A represents a methyl group;

(15) the method according to any one of (9) to (14), wherein Y represents a t-butyldiphenylsilyl group, a t-butyldimethylsilyl group, a tetrahydropyran-2-yl group, or a trityl group;

(16) the method according to any one of (9) to (14), wherein Y represents a trityl group;

(17) the method according to any one of (9) to (16), wherein n is 1;

(18) the method according to any one of (9) to (17), wherein the acid catalyst is sulfuric acid, p-toluenesulfonic acid, or methanesulfonic acid;

(19) the method according to any one of (9) to (18), wherein step (ii) is performed using a trivalent phosphorus reagent and an azodicarboxylate ester;

(20) the method according to (19), wherein the trivalent phosphorus reagent is triphenylphosphine or tri(n-butyl)phosphine;

(21) the method according to (19) or (20), wherein the azodicarboxylate ester is diethyl azodicarboxylate, diisopropyl azodicarboxylate, or di t-butyl azodicarboxylate;

(22) the method according to any one of (9) to (21), wherein step (iii) is performed using an acid;

(23) the method according to (22), wherein the acid is hydrochloric acid, sulfuric acid, trifluoroacetic acid, methanesulfonic acid, or p-toluenesulfonic acid;

(9b) the method according to (9), wherein $Z^1$ and $Z^2$ each represent a benzyl group, A represents a methyl group, Y represents a trityl group, and n is 1;

(9c) the method according to (9), wherein the acid catalyst is sulfuric acid, p-toluenesulfonic acid, or methanesulfonic acid, step (ii) is performed using a trivalent phosphorus reagent and an azodicarboxylate ester, and step (iii) is performed using an acid;

(9d) the method according to (9), wherein the acid catalyst is sulfuric acid, p-toluenesulfonic acid, or methanesulfonic acid, step (ii) is performed using a trivalent phosphorus reagent and an azodicarboxylate ester, the trivalent phosphorus reagent used for step (ii) is triphenylphosphine or tri(n-butyl)phosphine, the azodicarboxylate ester used for step (ii) is diethyl azodicarboxylate, diisopropyl azodicarboxylate, or di t-butyl azodicarboxylate, step (iii) is performed using an acid, and the acid used for step (iii) is hydrochloric acid, sulfuric acid, trifluoroacetic acid, methanesulfonic acid, or p-toluenesulfonic acid;

(9e) the method according to (9), wherein $Z^1$ and $Z^2$ each represent a benzyl group, A represents a methyl group, Y represents a trityl group, n is 1, the acid catalyst is sulfuric acid, p-toluenesulfonic acid, or methanesulfonic acid, step (ii) is performed using a trivalent phosphorus reagent and an azodicarboxylate ester, the trivalent phosphorus reagent used for step (ii) is triphenylphosphine or tri(n-butyl)phosphine, the azodicarboxylate ester used for step (ii) is diethyl azodicarboxylate, diisopropyl azodicarboxylate, or di t-butyl azodicarboxylate, step (iii) is performed using an acid, and the acid used for step (iii) is hydrochloric acid, sulfuric acid, trifluoroacetic acid, methanesulfonic acid, or p-toluenesulfonic acid;

(24) a method for producing a compound represented by formula (VI):

[Formula 14]

(VI)

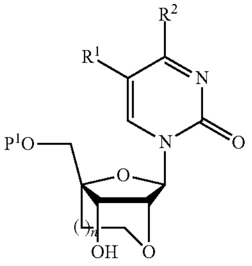

wherein $R^1$ represents a lower alkyl group or a hydrogen atom, $R^2$ represents a hydroxyl group, an amino group, or an amino group protected by an aliphatic acyl group or an aromatic acyl group, $P^1$ represents a trityl group optionally substituted with 1 to 3 lower alkoxy groups, and n represents an integer of 0 to 4, or a salt thereof, the method comprising:

(i) a step of reacting a compound represented by formula (II):

[Formula 15]

(II)

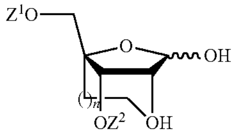

wherein $Z^1$ and $Z^2$ are identical or different and each represent a protective group for a hydroxy group, and n represents an integer of 0 to 4, with an activator in a solvent, to convert the hydroxyl group at the 1-position into a group that forms a leaving group; and (ii) a step of reacting the compound represented by formula (VII) obtained in step (i):

[Formula 16]

(VII)

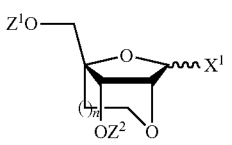

wherein $Z^1$, $Z^2$, and n have the same meanings as above, $X^1$ represents a group that forms a leaving group, with a compound represented by formula (VIII):

[Formula 17]

(VIII)

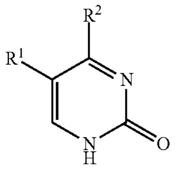

wherein $R^1$ and $R^2$ have the same meanings as above, or a salt thereof, in a solvent in the presence of a halogenating agent, to stereoselectively obtain a compound represented by formula (IX):

[Formula 18]

(IX)

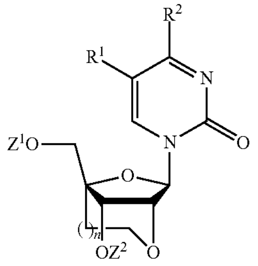

wherein $Z^1$, $Z^2$, $R^1$, $R^2$, and n have the same meanings as above, or a salt thereof;

(25) the method according to (24), wherein $Z^1$ and $Z^2$ are identical or different and each represent an aliphatic acyl group, an aromatic acyl group, a methyl group substituted with 1 to 3 aryl groups, a methyl group substituted with 1 to 3 aryl groups in which each aryl ring is substituted with a lower alkyl, lower alkoxy, halogen, or cyano group, or a silyl group;

(26) the method according to (24), wherein $Z^1$ and $Z^2$ are identical or different and each represent a benzyl group, a p-methoxybenzyl group, a t-butyldiphenylsilyl group, or a t-butyldimethylsilyl group;

(27) the method according to (24), wherein $Z^1$ and $Z^2$ each represent a benzyl group;

(28) the method according to any one of (24) to (27), wherein $P^1$ represents a 4,4'-dimethoxytrityl group;

(29) the method according to any one of (24) to (28), wherein $X^1$ represents a halogen atom, an aliphatic acyloxy group, a halogen-substituted lower alkylimidoxy group, or a halogen-substituted lower alkylsulfonyloxy group;

(30) the method according to any one of (24) to (28), wherein $X^1$ represents an iodine atom, an acetoxy group, or a trichloroacetimidoxy group;

(31) the method according to any one of (24) to (30), wherein n is 1;

(32) the method according to any one of (24) to (31), wherein $R^1$ represents a methyl group or a hydrogen atom;

(33) the method according to any one of (24) to (32), wherein $R^2$ represents a hydroxyl group or a benzoylamino group;

(34) the method according to any one of (24) to (31), wherein $R^1$ represents a methyl group, and $R^2$ represents a hydroxyl group;

(35) the method according to any one of (24) to (31), wherein $R^1$ represents a methyl group, and $R^2$ represents a benzoylamino group;

(36) the method according to any one of (24) to (35), comprising:

(iii) a step of reacting the compound represented by formula (IX) obtained in step (ii):

[Formula 19]

(IX)

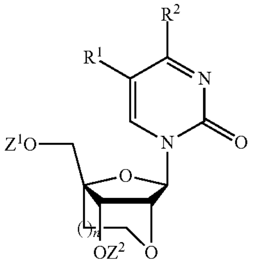

wherein $Z^1$, $Z^2$, $R^1$, $R^2$, and n have the same meanings as above, or a salt thereof, with a deprotection reagent for a hydroxyl group in a solvent, to deprotect $Z^1$ and $Z^2$; and (iv) a step of reacting the diol compound obtained in step (iii) or a salt thereof, with a protection reagent for a primary hydroxyl group, to obtain a compound represented by formula (VI):

[Formula 20]

(VI)

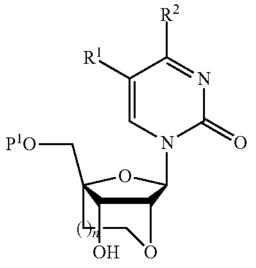

wherein $P^1$, $R^1$, $R^2$, and n have the same meanings as above, or a salt thereof;

(37) the method according to any one of (24) to (36), wherein the activator is acetic anhydride, benzoic anhydride, trichloroacetonitrile, carbonyldiimidazole, or diphenyl chlorophosphate;

(38) the method according to any one of (24) to (37), wherein the halogenating agent is chlorotrimethylsilane, bromotrimethylsilane, or iodotrimethylsilane;

(24a) the method according to (24), wherein $Z^1$ and $Z^2$ each represent a benzyl group, $P^1$ represents a 4,4'-dimethoxytrityl group, n is 1, $R^1$ represents a methyl group, and $R^2$ represents a benzoylamino group;

(24b) the method according to (24), wherein $Z^1$ and $Z^2$ each represent a benzyl group, $P^1$ represents a 4,4'-dimethoxytrityl group, $X^1$ represents an iodine atom, an acetoxy group, or a trichloroacetimidoxy group, n is 1, $R^1$ represents a methyl group, and $R^2$ represents a benzoylamino group;

(24c) the method according to (24), wherein the activator is acetic anhydride, benzoic anhydride, trichloroacetonitrile, carbonyldiimidazole, or diphenyl chlorophosphate, and the halogenating agent is chlorotrimethylsilane, bromotrimethylsilane, or iodotrimethylsilane;

(24d) the method according to (24), wherein $Z^1$ and $Z^2$ each represent a benzyl group, $P^1$ represents a 4,4'-dimethoxytrityl group, $X^1$ represents an iodine atom, an acetoxy group, or a trichloroacetimidoxy group, n is 1, $R^1$ represents a methyl group, $R^2$ represents a benzoylamino group, the activator is acetic anhydride, benzoic anhydride, trichloroacetonitrile, carbonyldiimidazole, or diphenyl chlorophosphate, and the halogenating agent is chlorotrimethylsilane, bromotrimethylsilane, or iodotrimethylsilane;

(39) a method for producing a compound represented by formula (X):

[Formula 21]

(X)

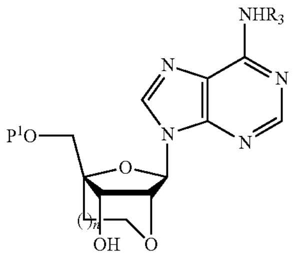

wherein $R^3$ represents an aliphatic acyl group or an aromatic acyl group, $P^1$ represents a trityl group optionally substituted with 1 to 3 lower alkoxy groups, and n represents an integer of 0 to 4, or a salt thereof, the method comprising:

(i) a step of reacting a compound represented by formula (II):

[Formula 22]

(II)

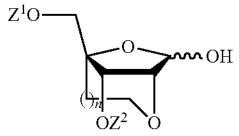

wherein $Z^1$ and $Z^2$ are identical or different and each represent a protective group for a hydroxy group, and n has the same meaning as above, with an activator in a solvent, to convert the hydroxyl group at the 1-position into a group that forms a leaving group;

(ii) a step of reacting the compound represented by formula (XI) obtained in step (i):

[Formula 23]

(XI)

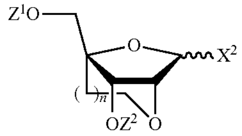

wherein $Z^1$, $Z^2$, and n have the same meanings as above, X represents a group that forms a leaving group, with a compound represented by formula (XII):

[Formula 24]

(XII)

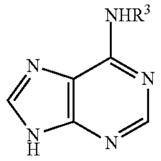

wherein $R^3$ has the same meaning as above, or a salt thereof, in a solvent in the presence of an acid reagent; and (iii) a step of then performing isomerization, to stereoselectively obtain a compound represented by formula (XIII):

[Formula 25]

(XIII)

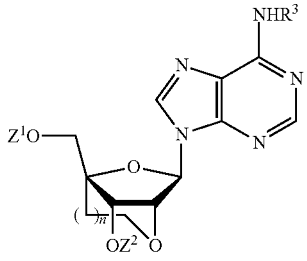

wherein $Z^1$, $Z^2$, $R^3$, and n have the same meanings as above, or a salt thereof;

(39a) the method according to (39), wherein isomerization is performed by heating in step (iii);

(40) the method according to (39), wherein $Z^1$ and $Z^2$ are identical or different and each represent an aliphatic acyl group, an aromatic acyl group, a methyl group substituted with 1 to 3 aryl groups, a methyl group substituted with 1 to 3 aryl groups in which each aryl ring is substituted with a lower alkyl, lower alkoxy, halogen, or cyano group, or a silyl group;

(41) the method according to (39) wherein $Z^1$ and $Z^2$ are identical or different and each represent a benzyl group, a p-methoxybenzyl group, a t-butyldiphenylsilyl group, or a t-butyldimethylsilyl group;

(42) the method according to (39), wherein $Z^1$ and $Z^2$ each represent a benzyl group;

(43) the method according to any one of (39) to (42), wherein $P^1$ represents a 4,4'-dimethoxytrityl group;

(44) the method according to any one of (39) to (43), wherein $X^2$ represents a halogen atom, an aliphatic acyloxy group, a halogen-substituted lower alkylimidoxy group, or a halogen-substituted lower alkylsulfonyloxy group;

(45) the method according to any one of (39) to (43), wherein $X^2$ represents an acetoxy group;

(46) the method according to any one of (39) to (45), wherein n is 1;

(47) the method according to any one of (39) to (46), wherein $R^3$ represents an acetyl group or a benzoyl group;

(48) the method according to any one of (39) to (46), wherein $R^3$ represents a benzoyl group;

(49) the method according to any one of (39) to (48), comprising:

(iv) a step of reacting the compound represented by formula (XIII) obtained in step (iii):

[Formula 26]

(XIII)

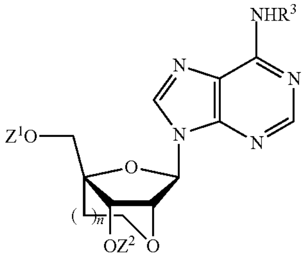

wherein $Z^1$, $Z^2$, $R^3$, and n have the same meanings as above, or a salt thereof, with a deprotection reagent for a hydroxyl group in a solvent, to deprotect $Z^1$ and $Z^2$; and (v) a step of reacting the diol compound obtained in step (iv) or a salt thereof, with a protection reagent for a primary hydroxyl group and selectively protecting the primary hydroxyl group, to obtain a compound represented by formula (X):

[Formula 27]

(X)

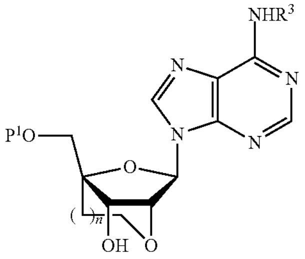

wherein $R^3$, n, and $P^1$ have the same meanings as above, or a salt thereof;

(50) the method according to any one of (39) to (49), wherein the activator is acetic anhydride, benzoic anhydride, trichloroacetonitrile, carbonyldiimidazole, or diphenyl chlorophosphate;

(51) the method according to any one of (39) to (50), wherein the acid reagent is trimethylsilyl trifluoromethanesulfonate and trifluoroacetic acid;

(39b) the method according to (39), wherein $Z^1$ and $Z^2$ each represent a benzyl group, $P^1$ represents a 4,4'-dimethoxytrityl group, n is 1, and $R^3$ represents a benzoyl group;

(39c) the method according to (39), wherein $Z^1$ and $Z^2$ each represent a benzyl group, $P^1$ represents a 4,4'-dimethoxytrityl group, $X^2$ represents an acetoxy group, n is 1, and $R^3$ represents a benzoyl group;

(39d) the method according to (39), wherein the activator is acetic anhydride, benzoic anhydride, trichloroacetonitrile, carbonyldiimidazole, or diphenyl chlorophosphate, and the acid reagent is trimethylsilyl trifluoromethanesulfonate and trifluoroacetic acid;

(39e) the method according to (39), wherein $Z^1$ and $Z^2$ each represent a benzyl group, $P^1$ represents a 4,4'-dimethoxytrityl group, $X^2$ represents an acetoxy group, n is 1, $R^3$ represents a benzoyl group, the activator is acetic anhydride, benzoic anhydride, trichloroacetonitrile, carbonyldiimidazole, or diphenyl chlorophosphate, and the acid reagent is trimethylsilyl trifluoromethanesulfonate and trifluoroacetic acid;

(52) a compound represented by formula (XIV):

[Formula 28]

(XIV)

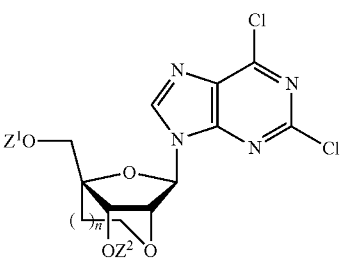

wherein $Z^1$ and $Z^2$ are identical or different and each represent a protective group for a hydroxy group, and n represents an integer of 0 to 4, or a salt thereof;

(53) the compound according to (52), wherein $Z^1$ and $Z^2$ are identical or different and each represent an aliphatic acyl group, an aromatic acyl group, a methyl group substituted with 1 to 3 aryl groups, a methyl group substituted with 1 to 3 aryl groups in which each aryl ring is substituted with a lower alkyl, lower alkoxy, halogen, or cyano group, or a silyl group, or a salt thereof;

(54) the compound according to (52), wherein $Z^1$ and $Z^2$ are identical or different and each represent a benzyl group, a p-methoxybenzyl group, a t-butyldiphenylsilyl group, or a t-butyldimethylsilyl group, or a salt thereof;

(55) the compound according to (52), wherein $Z^1$ and $Z^2$ each represent a benzyl group, or a salt thereof;

(56) the compound according to any one of (52) to (55), wherein n is 1, or a salt thereof;

(57) the compound represented by formula (XIV'):

[Formula 29]

(XIV')

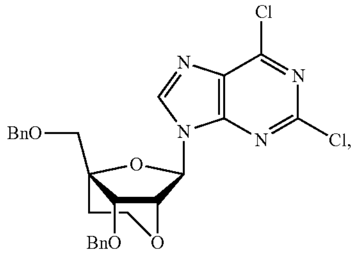

or a salt thereof;

(58) a method for producing a compound represented by formula (X):

[Formula 30]

(X)

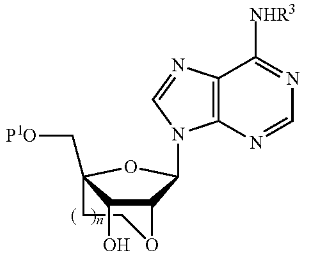

wherein $P^1$ represents a trityl group optionally substituted with 1 to 3 lower alkoxy groups, $R^3$ represents an aliphatic acyl group or an aromatic acyl group, and n represents an integer of 1 to 4, or a salt thereof, the method comprising:

(i) a step of reacting a compound represented by formula (XIV):

[Formula 31]

(XIV)

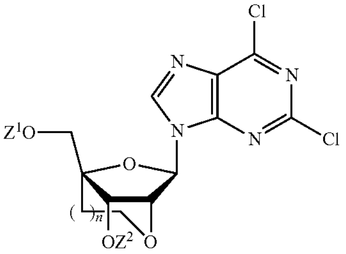

wherein $Z^1$ and $Z^2$ are identical or different and each represent a protective group for a hydroxy group, and n represents an integer of 0 to 4, or a salt thereof, with an aminating agent, to replace the chlorine atom at the 6-position of the purine ring with an amino group; and (ii) a step of reacting the compound represented by formula (XV) obtained in step (i):

[Formula 32]

(XV)

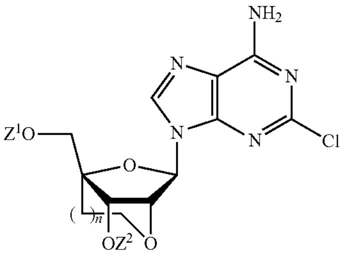

wherein $Z^1$, $Z^2$, and n have the same meanings as above, or a salt thereof, with a reducing agent in a solvent in the presence of a metal catalyst to replace the chlorine atom at the 2-position of the purine ring with a hydrogen atom and deprotect $Z^1$ and $Z^2$, to obtain a compound represented by formula (XVI):

[Formula 33]

(XVI)

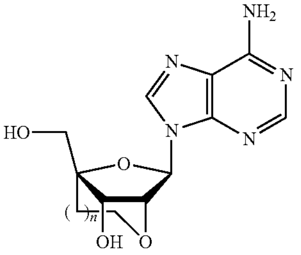

wherein n has the same meaning as above, or a salt thereof;

(58b) the method according to (58), wherein the metal catalyst is a metal catalyst supported on carbon;

(59) the method according to (58), wherein $Z^1$ and $Z^2$ are identical or different and each represent an aliphatic acyl group, an aromatic acyl group, a methyl group substituted with 1 to 3 aryl groups, a methyl group substituted with 1 to 3 aryl groups in which each aryl ring is substituted with a lower alkyl, lower alkoxy, halogen, or cyano group, or a silyl group;

(60) the method according to (58), wherein $Z^1$ and $Z^2$ are identical or different and each represent a benzyl group, a p-methoxybenzyl group, a t-butyldiphenylsilyl group, or a t-butyldimethylsilyl group;

(61) the method according to (58), wherein $Z^1$ and $Z^2$ each represent a benzyl group;

(62) the method according to any one of (58) to (61), wherein $P^1$ represents a 4,4'-dimethoxytrityl group;

(63) the method according to any one of (58) to (62), wherein n is 1;

(64) the method according to any one of (58) to (63), wherein $R^3$ represents an acetyl group or a benzoyl group;

(65) the method according to any one of (58) to (63), wherein $R^3$ represents a benzoyl group;

(66) the method according to any one of (58) to (65), comprising:

(iii) a step of reacting the compound represented by formula (XVI) obtained in step (ii):

[Formula 34]

(XVI)

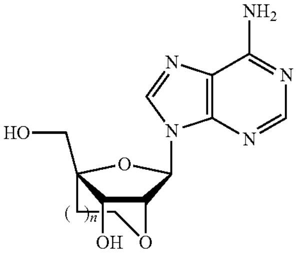

wherein n has the same meaning as above, or a salt thereof, with a protection reagent for a primary hydroxyl group to selectively protect a primary hydroxyl group; and (iv) a step of reacting the compound represented by formula (XVII) obtained in step (iii):

[Formula 35]

(XVII)

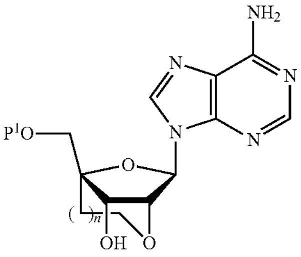

wherein $P^1$ and n have the same meanings as above, or a salt thereof, with an acylating agent, to obtain a compound represented by formula (X):

[Formula 36]

(X)

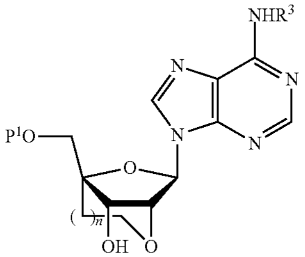

wherein $P^1$, $R^3$, and n have the same meanings as above, or a salt thereof;

(67) the method according to any one of (58) to (66), wherein the aminating agent is ammonia, aqueous ammonia solution, ammonium carbonate, or ammonium acetate;

(68) the method according to any one of (58) to (67), wherein the metal catalyst is palladium, palladium hydroxide, or platinum;

(69) the method according to any one of (58) to (68), wherein the reducing agent is hydrogen, formic acid, or ammonium formate;

(70) the method according to any one of (66) to (69), wherein the acylating agent is benzoyl chloride or benzoic anhydride;

(58a) the method according to (58), comprising: (iii-a) a step of reacting the compound represented by formula (XVI) obtained in step (ii) of (58):

[Formula 37]

(XVI)

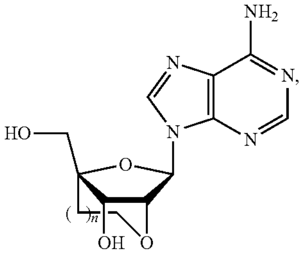

wherein n has the same meaning as above, or a salt thereof, with a protection reagent for a primary hydroxyl group, to selectively protect a primary hydroxyl group; and (iv-a) a step of reacting the compound represented by formula (XVII) obtained in step (iii-a):

[Formula 38]

(XVII)

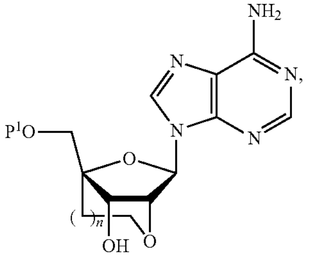

wherein $P^1$ and n have the same meanings as above, or a salt thereof, with an acylating agent, to obtain a compound represented by formula (X):

[Formula 39]

(X)

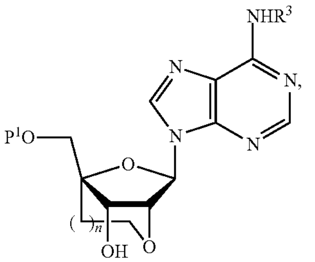

wherein $P^1$, $R^3$, and n have the same meanings as above, or a salt thereof, wherein $Z^1$ and $Z^2$ each represent a benzyl group, $P^1$ represents a 4,4'-dimethoxytrityl group, n is 1, $R^3$ represents a benzoyl group, the aminating agent is ammonia, aqueous ammonia solution, ammonium carbonate, or ammonium acetate, the metal catalyst is palladium, palladium hydroxide, or platinum, the reducing agent is hydrogen, formic acid, or ammonium formate, and the acylating agent is benzoyl chloride or benzoic anhydride;

(71) a method for producing a compound represented by formula (XVIII):

[Formula 40]

(XVIII)

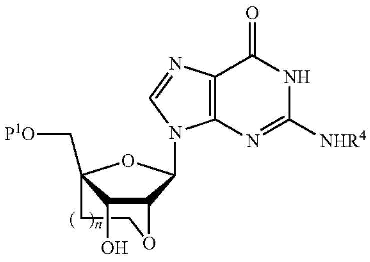

wherein $P^1$ represents a trityl group optionally substituted with 1 to 3 lower alkoxy groups, $R^4$ represents an aliphatic acyl group or an aromatic acyl group, and n represents an integer of 1 to 4, or a salt thereof, the method comprising:

(i) a step of reacting a compound represented by formula (XIV):

[Formula 41]

(XIV)

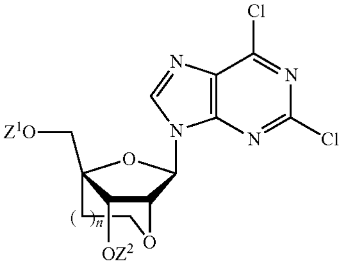

wherein $Z^1$ and $Z^2$ are identical or different and each represent a protective group for a hydroxy group, and n represents an integer of 0 to 4, or a salt thereof, with benzyl alcohol optionally substituted with a lower alkyl, lower alkoxy, halogen, or cyano group in a solvent in the presence of a base, to replace the chlorine atom at the 6-position of the purine ring with a benzyloxy group optionally substituted with a lower alkyl, lower alkoxy, halogen, or cyano group; and (ii) a step of cross-coupling the compound represented by formula (XIX) obtained in step (i):

[Formula 42]

(XIX)

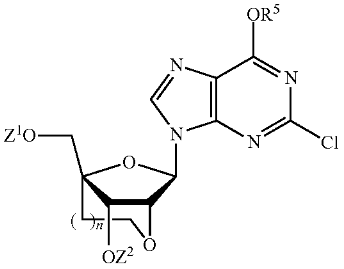

wherein $Z^1$, $Z^2$, and n have the same meanings as above, and $R^5$ represents a benzyl group optionally substituted with a lower alkyl, lower alkoxy, halogen, or cyano group, or a salt thereof, with an amidating agent in a solvent in the presence of a palladium catalyst and a phosphine ligand, to obtain a compound represented by formula (XX):

[Formula 43]

(XX)

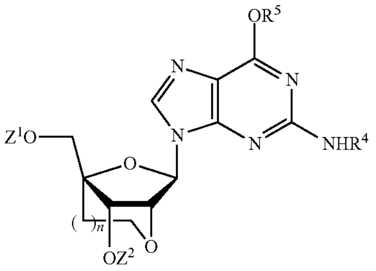

wherein $Z^1$, $Z^2$, $R^4$, $R^5$, and n have the same meanings as above, or a salt thereof;

(72) the method according to (71), wherein $Z^1$ and $Z^2$ are identical or different and each represent an aliphatic acyl group, an aromatic acyl group, a methyl group substituted with 1 to 3 aryl groups, a methyl group substituted with 1 to 3 aryl groups in which each aryl ring is substituted with a lower alkyl, lower alkoxy, halogen, or cyano group, or a silyl group;

(73) the method according to (71), wherein $Z^1$ and $Z^2$ are identical or different and each represent a benzyl group, a p-methoxybenzyl group, a t-butyldiphenylsilyl group, or a t-butyldimethylsilyl group;

(74) the method according to (71), wherein $Z^1$ and $Z^2$ each represent a benzyl group;

(75) the method according to any one of (71) to (74), wherein $P^1$ represents a 4,4'-dimethoxytrityl group;

(76) the method according to any one of (71) to (75), wherein n is 1;

(77) the method according to any one of (71) to (76), wherein $R^4$ represents an isobutyryl group;

(78) the method according to any one of (71) to (77), wherein $R^5$ represents a benzyl group;

(79) the method according to any one of (71) to (78), comprising:

(iii) a step of reacting the compound represented by formula (XX) obtained in step (ii):

[Formula 44]

(XX)

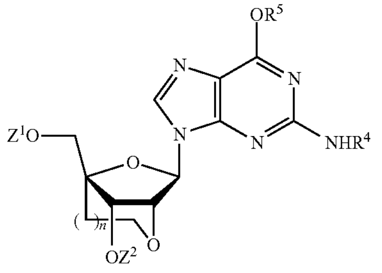

wherein $Z^1$, $Z^2$, $R^4$, $R^5$, and n have the same meanings as above, or a salt thereof, with a deprotection reagent for a hydroxyl group in a solvent, to deprotect $Z^1$, $Z^2$ and $R^5$; and (iv) a step of reacting the compound represented by formula (XXI) obtained in step (iii):

[Formula 45]

(XXI)

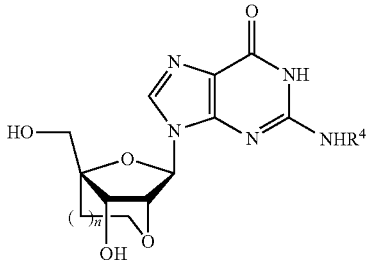

wherein $R^4$ and n have the same meanings as above, or a salt thereof, with a protection reagent for a primary hydroxyl group and selectively protecting the primary hydroxyl group, to obtain a compound represented by formula (XVIII):

[Formula 46]

(XVIII)

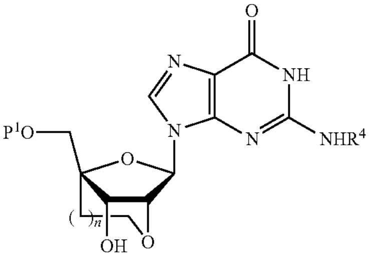

wherein $P^1$, $R^4$, and n have the same meanings as above, or a salt thereof;

(80) the method according to any one of (71) to (79), wherein the base is sodium hydroxide, sodium carbonate, cesium carbonate, triethylamine, pyridine, or 1,8-diazabicyclo[5.4.0]undec-7-ene;

(81) the method according to any one of (71) to (80), wherein the palladium catalyst is tris(dibenzylideneacetone) (chloroform)dipalladium, palladium (II) acetate, or tris(dibenzylideneacetone)dipalladium (0);

(82) the method according to any one of (71) to (81), wherein the phosphine ligand is 4,5'-bis(diphenylphosphino)-9,9' dimethylxanthene, 1,1'-bis(diphenylphosphino)ferrocene, 1,2-bis(diphenylphosphino)ethane, or 2-dicyclohexylphosphino-2'-(N,N-dimethylamino)biphenyl;

(83) the method according to any one of (71) to (82), wherein the amidating agent is acetyl amide, benzoyl amide, or isobutyl amide;

(84) the method according to any one of (79) to (83), wherein the deprotection reagent for a hydroxyl group is a metal catalyst and a reducing agent;

(84a) the method according to any one of (79) to (83), wherein the deprotection reagent for a hydroxyl group is a metal catalyst supported on carbon and hydrogen;

(85) the method according to (84), wherein the metal catalyst is palladium, palladium hydroxide, or platinum;

(86) the method according to (84) or (85), wherein the reducing agent is hydrogen, formic acid, or ammonium formate;

(71a) the method according to (71), comprising: (iii-a) a step of reacting the compound represented by formula (XX) obtained in step (ii) of (71):

[Formula 47]

(XX)

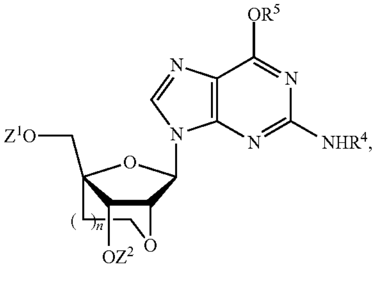

wherein $Z^1$, $Z^2$, $R^4$, $R^5$, and n have the same meanings as above, or a salt thereof, with a deprotection reagent for a hydroxyl group in a solvent, to deprotect $Z^1$, $Z^2$ and $R^5$; and (iv-a) a step of reacting the compound represented by formula (XXI) obtained in step (iii-a):

[Formula 48]

(XXI)

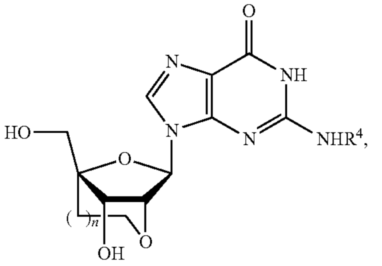

wherein $R^4$ and n have the same meanings as above, or a salt thereof, with a protection reagent for a primary hydroxyl group and selectively protecting the primary hydroxyl group, to obtain a compound represented by formula (XVIII):

[Formula 49]

(XVIII)

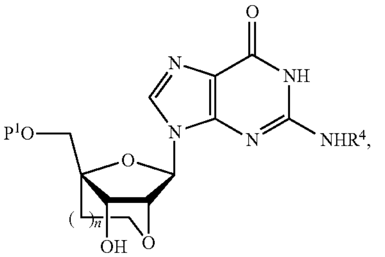

wherein $P^1$, $R^4$, and n have the same meanings as above, or a salt thereof, wherein $Z^1$ and $Z^2$ each represent a benzyl group, $P^1$ represents a 4,4'-dimethoxytrityl group, n is 1, $R^4$ represents an isobutyryl group, the base is sodium hydroxide, sodium carbonate, cesium carbonate, triethylamine, pyridine, or 1,8-diazabicyclo[5.4.0]undec-7-ene, the palladium catalyst is tris(dibenzylideneacetone) (chloroform)dipalladium, palladium (II) acetate, or tris(dibenzylideneacetone)dipalladium (0), the phosphine ligand is 4,5'-bis(diphenylphosphino)-9,9' dimethylxanthene, 1,1'-bis(diphenylphosphino)ferrocene, 1,2-bis(diphenylphosphino)ethane, or 2-dicyclohexylphosphino-2 '-(N,N-dimethylamino)biphenyl, the amidating agent is acetyl amide, benzoyl amide, or isobutyl amide, the deprotection reagent for a hydroxyl group is a metal catalyst supported on carbon and hydrogen, and the metal catalyst is palladium, palladium hydroxide, or platinum;

(87) a method for producing a compound represented by formula (XXII):

[Formula 50]

(XXII)

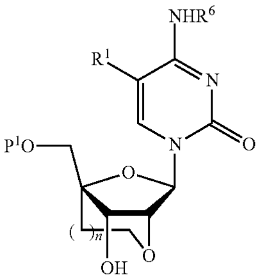

wherein $R^1$ represents a lower alkyl group or a hydrogen atom, $R^6$ represents an aliphatic acyl group or an aromatic acyl group, $P^1$ represents a trityl group optionally substituted with 1 to 3 lower alkoxy groups, and n represents an integer of 0 to 4, or a salt thereof, the method comprising:

(i) a step of reacting a compound represented by formula (XXIII):

[Formula 51]

(XXIII)

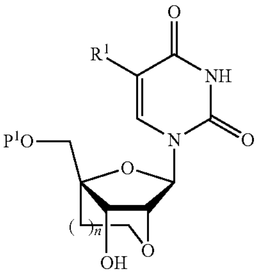

wherein $P^1$, $R^1$, and n have the same meanings as above, or a salt thereof, with a protection reagent for a hydroxyl group in a solvent, to protect the hydroxyl group at the 3'-position;

(ii) a step of reacting the compound represented by formula (XXIV) obtained in step (i):

[Formula 52]

(XXIV)

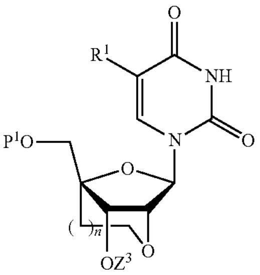

wherein $P^1$, $R^1$, and n have the same meanings as above, $Z^3$ represents an aliphatic acyl group or an aromatic acyl group, or a salt thereof, with an activator in a solvent in the presence of a base and a catalyst; and (iii) a step of then performing reaction with an aminating agent, to obtain a compound represented by formula (XXV):

[Formula 53]

(XXV)

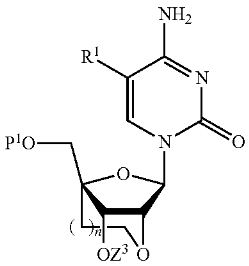

wherein $P^1$, $R^1$, $Z^3$, and n have the same meanings as above, or a salt thereof;

(88) the method according to (87), wherein $P^1$ represents a trityl group;

(89) the method according to (87) or (88), wherein $Z^3$ represents an acetyl group;

(90) the method according to any one of (87) to (89), wherein n is 1;

(91) the method according to any one of (87) to (90), wherein $R^1$ represents a methyl group or a hydrogen atom;

(92) the method according to any one of (87) to (91), wherein $R^6$ represents an acetyl group or benzoyl group;

(93) the method according to any one of (87) to (91), wherein $R^6$ represents a benzoyl group;

(94) the method according to any one of (87) to (93), comprising:

(iv) a step of reacting the compound represented by formula (XXV) obtained in step (iii):

[Formula 54]

(XXV)

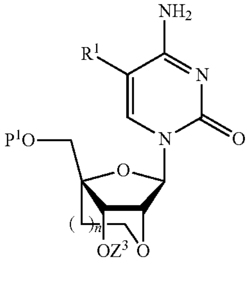

wherein $P^1$, $R^1$, $Z^3$, and n have the same meanings as above, or a salt thereof, with an acylating agent in a solvent, (v) a step of reacting the compound represented by formula (XXVI) obtained in step (iv):

[Formula 55]

(XXVI)

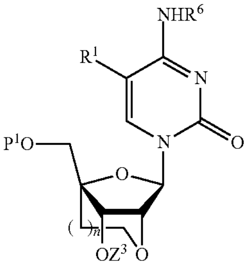

wherein $P^1$, $R^1$, $R^6$, $Z^3$, and n have the same meanings as above, or a salt thereof, with a deprotection reagent for a hydroxyl group and deprotecting only $Z^3$, to obtain a compound represented by formula (XXII):

[Formula 56]

(XXII)

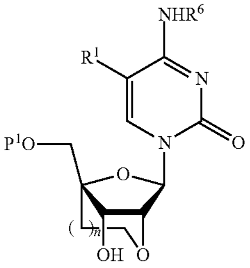

wherein $P^1$, $R^1$, $R^6$, and n have the same meanings as above, or a salt thereof;

(95) the method according to any one of (87) to (94), wherein the catalyst is N,N-dimethylaminopyridine or 1,8-diazabicyclo[5.4.0]undec-7-ene;

(96) the method according to any one of (87) to (95), wherein the activator is p-toluenesulfonyl chloride or 2,4,6-triisopropylbenzenesulfonyl chloride;

(97) the method according to any one of (87) to (96), wherein the aminating agent is ammonia, an aqueous ammonia solution, ammonium carbonate, or ammonium acetate;

(98) the method according to any one of (94) to (97), wherein the acylating agent is benzoyl chloride or benzoic anhydride;

(87a) the method according to (87), wherein $P^1$ represents a trityl group, $Z^3$ represents an acetyl group, n is 1, $R^1$ represents a methyl group or a hydrogen atom, and $R^6$ represents a benzoyl group;

(87b) the method according to (87), comprising: (iv-b) a step of reacting the compound represented by formula (XXV) obtained in step (iii) of (87):

[Formula 57]

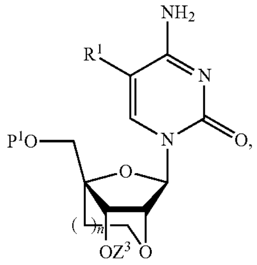

(XXV)

wherein $P^1$, $R^1$, $Z^3$, and n have the same meanings as above, or a salt thereof, with an acylating agent in a solvent; and (v-b) a step of reacting the compound represented by formula (XXVI) obtained in step (iv-b):

[Formula 58]

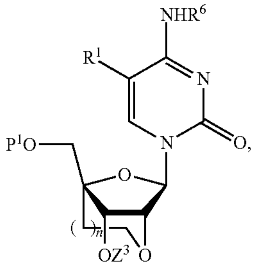

(XXVI)

wherein $P^1$, $R^1$, $R^6$, $Z^3$, and n have the same meanings as above, or a salt thereof, with a deprotection reagent for a hydroxyl group and deprotecting only $Z^3$, to obtain a compound represented by formula (XXII):

[Formula 58]

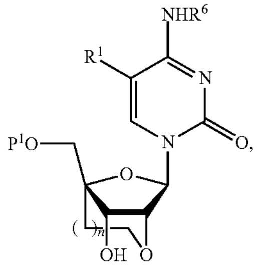

(XXII)

wherein $P^1$, $R^1$, $R^6$, and n have the same meanings as above, or a salt thereof, wherein the catalyst is N,N-dimethylaminopyridine or 1,8-diazabicyclo[5.4.0]undec-7-ene, the activator is p-toluenesulfonyl chloride or 2,4,6-triisopropylbenzenesulfonyl chloride, the aminating agent is ammonia, aqueous ammonia solution, ammonium carbonate, or ammonium acetate, and the acylating agent is benzoyl chloride or benzoic anhydride;

(87c) the method according to (87), comprising: (iv-c) a step of reacting the compound represented by formula (XXV) obtained in step (iii) of (87):

[Formula 60]

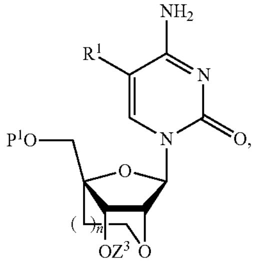

(XXV)

wherein $P^1$, $R^1$, $Z^3$, and n have the same meanings as above, or a salt thereof, with an acylating agent in a solvent, (v-c) a step of reacting the compound represented by formula (XXVI) obtained in step (iv-c):

[Formula 61]

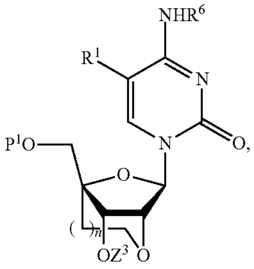

(XXVI)

wherein $P^1$, $R^1$, $R^6$, $Z^3$, and n have the same meanings as above, or a salt thereof, with a deprotection reagent for a hydroxyl group and deprotecting only $Z^3$, to obtain a compound represented by formula (XXII):

[Formula 62]

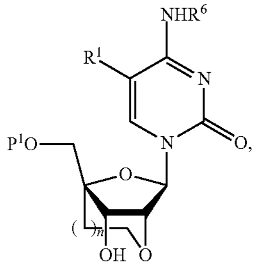

(XXII)

wherein $P^1$, $R^1$, $R^6$, and n have the same meanings as above, or a salt thereof, wherein $P^1$ represents a trityl group, $Z^3$ represents an acetyl group, n is 1, $R^1$ represents a methyl group or a hydrogen atom, $R^6$ represents a benzoyl group, the catalyst is N,N-dimethylaminopyridine, or 1,8-diazabicyclo[5.4.0]undec-7-ene, the activator is p-toluenesulfonyl chloride or 2,4,6-triisopropylbenzenesulfonyl chloride, the aminating agent is ammonia, aqueous ammonia solution, ammonium carbonate, or ammonium acetate, and the acylating agent is benzoyl chloride or benzoic anhydride;

(99) a production method comprising the steps of: reacting a compound represented by formula (XXVII):

[Formula 63]

(XXVII)

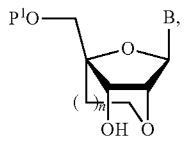

solvent in the presence of an activator and a drying agent, wherein $P^1$ represents a trityl group optionally substituted with 1 to 3 lower alkoxy groups, B represents a 2-oxo-pyrimidin-1-yl group optionally having one or more substituents selected from the group α below or a purin-9-yl group, and n represents an integer of 0 to 4, to produce a compound or a salt thereof represented by formula (XXVIII):

[Formula 64]

(XXVIII)

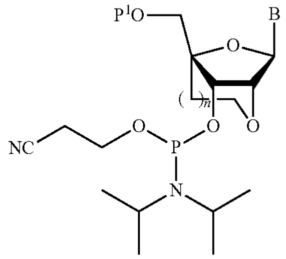

wherein $P^1$, B, and n have the same meanings as above. (group (α): a hydroxyl group, a protected hydroxyl group, a lower alkoxy group, a mercapto group, a protected mercapto group, a lower alkylthio group, an amino group, a protected amino group, a lower alkylamino group, a lower alkyl group, and a halogen atom;

(100) the method according to (99), wherein $P^1$ represents a 4,4'-dimethoxytrityl group;

(101) the method according to (99) or (100), wherein B represents a 2-oxo-4-hydroxy-5-methylpyrimidin-1-yl group, an amino group-protected 2-oxo-4-amino-pyrimidin-1-yl group, an amino group-protected 4-amino-5-methyl-2-oxo-pyrimidin-1-yl group, an amino group-protected 6-aminopurin-9-yl group, or an amino group-protected 2-amino-6-hydroxypurin-9-yl group;

(102) the method according to (99) or (100), wherein B represents a 2-oxo-4-hydroxy-5-methylpyrimidin-1-yl group, a 2-oxo-4-benzoylamino-pyrimidin-1-yl group, a 4-benzoylamino-5-methyl-2-oxo-pyrimidin-1-yl group, a 6-benzoylaminopurin-9-yl group, or a 2-isobutyrylamino-6-hydroxypurin-9-yl group;

(103) the method according to any one of (99) to (102), wherein n is 1;

(104) the method according to any one of (99) to (103), wherein the activator is pyridine trifluoroacetate, N-methylimidazole trifluoroacetate, N-isopropylimidazole trifluoroacetate, 5-benzylthiotetrazole, 5-phenyltetrazole, 4,5-dicyanoimidazole, or 2,4,5-tribromoimidazole;

(105) the method according to any one of (99) to (103), wherein the activator is 4,5-dicyanoimidazole;

(106) the method according to any one of (99) to (105), wherein the amidite-forming reagent is 2-cyanoethyl N,N,N',N'-tetraisopropyl phosphorodiamidite or 2-cyanoethyldiisopropyl chlorophosphoramidite;

(107) the method according to any one of (99) to (105), wherein the amidite-forming reagent is 2-cyanoethyl N,N,N',N'-tetraisopropyl phosphorodiamidite;

(108) the method according to any one of (99) to (107), wherein the drying agent is molecular sieve 3A, molecular sieve 4A, or molecular sieve 5A;

(99a) the method according to (99), wherein $P^1$ represents a 4,4'-dimethoxytrityl group, B represents a 2-oxo-4-hydroxy-5-methylpyrimidin-1-yl group, a 2-oxo-4-benzoylamino-pyrimidin-1-yl group, a 4-benzoylamino-5-methyl-2-oxo-pyrimidin-1-yl group, a 6-benzoylaminopurin-9-yl group, or a 2-isobutyrylamino-6-hydroxypurin-9-yl group, and n is 1;

(99b) the method according to (99), wherein the activator is pyridine trifluoroacetate, N-methylimidazole trifluoroacetate, N-isopropylimidazole trifluoroacetate, 5-benzylthiotetrazole, 5-phenyltetrazole, 4,5-dicyanoimidazole, or 2,4,5-tribromoimidazole, the amidite-forming reagent is 2-cyanoethyl N,N,N',N'-tetraisopropyl phosphorodiamidite or 2-cyanoethyl diisopropyl chlorophosphoramidite, and the drying agent is molecular sieve 3A, molecular sieve 4A, or molecular sieve 5A;

(99c) the method according to (99), wherein $P^1$ represents a 4,4'-dimethoxytrityl group, B represents 2-oxo-4-hydroxy-5-methylpyrimidin-1-yl group, 2-oxo-4-benzoylamino-pyrimidin-1-yl group, 4-benzoylamino-5-methyl-2-oxo-pyrimidin-1-yl group, 6-benzoylaminopurin-9-yl group, or 2-isobutyrylamino-6-hydroxypurin-9-yl group, n is 1, the activator is pyridine trifluoroacetate, N-methylimidazole trifluoroacetate, N-isopropylimidazole trifluoroacetate, 5-benzylthiotetrazole, 5-phenyltetrazole, 4,5-dicyanoimidazole, or 2,4,5-tribromoimidazole, the amidite-forming reagent is 2-cyanoethyl N,N,N',N'-tetraisopropyl phosphorodiamidite or 2-cyanoethyl diisopropyl chlorophosphoramidite, and the drying agent is molecular sieve 3A, molecular sieve 4A, or molecular sieve 5A;

(109) a method for producing an oligonucleotide, comprising:

(A) a step of synthesizing an ENA monomer by the method according to any one of (99) to (108); and (B) a step of extending the nucleotide chain according to a desired sequence using the ENA monomer obtained in step (A), a phosphoramidite compound of another nucleic acid, and/or a phosphoramidite compound of a ligand;

(110) the method according to (109), wherein the oligonucleotide consists of a sequence represented by any one formula selected from DMD AO01 to DMD AO15 below:

(SEQ ID NO: 1)

(DMD AO01) HO-$C^{e2s}$-$A^{m1s}$-$G^{m1s}$-$T^{e2s}$_$T^{e2s}$-$U^{m1s}$-$G^{m1s}$-$C^{e2s}$-$C^{e2s}$-$G^{m1s}$-$C^{e2s}$-$T^{e2s}$-$G^{m1s}$-$C^{e2s}$-$C^{e2s}$-$C^{e2s}$-$A^{m1s}$-$A^{m1s}$-$CH_2CH_2OH$;

-continued (SEQ ID NO: 2)
(DMD AO02) HO-$T^{e2s}$-$G^{m1s}$-$T^{e2s}$-$T^{e2s}$-$C^{e2s}$-$T^{e2s}$-$G^{m1s}$-$A^{m1s}$-$C^{e2s}$-$A^{m1s}$-$A^{m1s}$-$C^{e2s}$-$A^{m1s}$-$G^{m1s}$-$T^{e2s}$-$T^{e2s}$-$T^{e2s}$-$G^{m1s}$-$CH_2CH_2OH$;

(SEQ ID NO: 3)
(DMD AO03) HO-$C^{e2s}$-$G^{m1s}$-Ce25-$T^{e2s}$-$G^{m1s}$-$C^{m1s}$-$C^{e2s}$-$C^{e2s}$-$A^{m1s}$-$A^{m1s}$-$T^{e2s}$-$G^{m1s}$-$C^{e2s}$-$C^{e2s}$-$A^{m1s}$-$U^{m1s}$-$C^{e2s}$-$C^{e2s}$-$CH_2CH_2OH$;

(SEQ ID NO: 4)
(DMD AO04) HO-$C^{e2s}$-$A^{m1s}$-$T^{e2s}$-$A^{m1s}$-$A^{m1s}$-$T^{e2s}$-$G^{m1s}$-$A^{m1s}$-$A^{e2s}$-$A^{m1s}$-$A^{m1s}$-$C^{e2s}$-$G^{m1s}$-$C^{m1s}$-$C^{e2s}$-$G^{m1s}$-$C^{e2s}$-$C^{e2s}$-$CH_2CH_2OH$;

(SEQ ID NO: 5)
(DMD AO05) HO-$T^{e2s}$-$U^{m1s}C^{e2s}$-$C^{m1s}$-$C^{e2s}$-Ande-A $^{m1s}$-$T^{e2s}$-$U^{m1s}$-$C^{m1s}$-$T^{e2s}$-$C^{e2s}$-$A^{m1s}$-$G^{m1s}$-$G^{m1s}$-$A^{e2s}$-$A^{m1s}$-$T^{e2s}$-$CH_2CH_2OH$;

(SEQ ID NO: 6)
(DMD AO06) HO-$C^{e2s}$-$C^{e2s}$-$A^{m1s}$-$T^{m1s}$-$T^{e2s}$-$U^{m1s}$-$G^{m1s}$-$T^{e2s}$-$A^{m1s}$-$U^{m1s}$-$T^{e2s}$-$T^{e2s}$-$A^{m1s}$-$G^{m1s}$-$C^{e2s}$-$A^{m1s}$-$T^{e2s}$-$G^{m1s}$-$CH_2CH_2OH$;

(SEQ ID NO: 7)
(DMD AO07) HO-$G^{m1s}$-$G^{m1s}$-$C^{e2s}$-$T^{e2s}$-$G^{m1s}$-$C^{m1s}$-$T^{e2s}$-$T^{e2s}$-$U^{m1s}$-$G^{m1s}$-$C^{e2s}$-$C^{m1s}$-$C^{m1s}$-$T^{e2s}$-$C^{e2s}$-$A^{m1s}$-$G^{m1s}$-$C^{e2s}$-$CH_2CH_2OH$;

(SEQ ID NO: 8)
(DMD AO08) HO-$G^{m1s}$-$C^{e2s}$-$T^{e2s}$-$A^{m1s}$-$G^{m1s}$-$G^{m1s}$-$T^{e2s}$-$C^{e2s}$-$A^{m1s}$-$G^{m1s}$-$G^{m1s}$-$T^{e2s}$-$G^{m1s}$-$C^{m1s}$-$T^{e2s}$-$T^{e2s}$-$U^{m1s}$-$CH_2CH_2OH$;

(SEQ ID NO: 9)
(DMD AO09) HO-$A^{m1s}$-$C^{e2s}$-$C^{e2s}$-$G^{m1s}$-$C^{m1s}$-$C^{e2s}$-$T^{e2s}$-$U^{m1s}$-$C^{m1s}$-$C^{e2s}$-$A^{m1s}$-$C^{m1s}$-$T^{e2s}$-$C^{e2s}$-$A^{m1s}$-$G^{m1s}$-$A^{e2s}$-$G^{m1s}$-$CH_2CH_2OH$;

(SEQ ID NO: 10)
(DMD AO10) HO-$G^{e2s}$-$G^{e2s}$-$C^{e2s}$-$A^{e2s}$-$T^{e2s}$-$U^{m1s}$-$U^{m1s}$-$C^{m1s}$-$U^{m1s}$-$A^{m1s}$-$G^{m1s}$-$U^{m1s}$-$t^{m1s}$-Te25-$G^{e2s}$-$G^{e2s}$-$A^{e2s}$-$G^{e2s}$-$CH_2CH_2OH$;

(SEQ ID NO: 11)
(DMD AO11) HO-$G^{m1s}$-$G^{m1s}$-$C^{e2s}$-$A^{m1s}$-$T^{e2s}$-$T^{e2s}$-$U^{m1s}$-$C^{e2s}$-$T^{e2s}$-$A^{m1s}$-$G^{m1s}$-$U^{m1s}$-$T^{e2s}$-$T^{e2s}$-$G^{m1s}$-$G^{m1s}$-$A^{e2s}$-$G^{m1s}$-$CH_2CH_2OH$;

(SEQ ID NO: 12)
(DMD AO12) HO-$A^{e2s}$-$G^{m1s}$-$T^{e2s}$-$U^{m1s}$-$T^{e2s}$-$G^{m1s}$-$G^{m1s}$-$A^{e2s}$-$G^{m1s}$-$A^{m1s}$-Tes-$G^{m1s}$-$G^{m1s}$-$C^{e2s}$-$A^{e2s}$-$G^{m1s}$-$T^{e2s}$-$T^{e2s}$-$CH_2CH_2OH$;

-continued (SEQ ID NO: 13)
(DMD AO13) HO-$C^{e2s}$-$T^{e2s}$-$c^{m1s}$-$C^{e2s}$-$T^{e2s}$-$U^{m1s}$-$C^{e2s}$-Ce23-$A^{m1s}$-$T^{e2s}$-$G^{m1s}$-$A^{m1s}$-$C^{e2s}$-$T^{e2s}$-$C^{e2s}$-$A^{m1s}$-$A^{m1s}$-$G^{m1s}$-$CH_2CH_2OH$;

(SEQ ID NO: 14)
(DMD AO14) HO-$C^{e2s}$-$T^{e2s}$-$G^{m1s}$-$A^{m1s}$-$A^{m1s}$-$G^{m1s}$-$G^{m1s}$-$T^{e2s}$-$G^{m1s}$-$T^{e2s}$-$T^{e2s}$-$C^{e2s}$-$T^{e2s}$-$T^{e2s}$-$G^{m1s}$-$T^{e2s}$-$A^{m1s}$-$C^{e2s}$-$CH_2CH_2OH$;

and (SEQ ID NO: 15)
(DMD AO15) HO-$T^{e2s}$-$T^{e2s}$-$C^{m1s}$-$C^{e2s}$-$A^{m1s}$-$G^{m1s}$-$C^{e2s}$-$C^{e2s}$-$A^{m1s}$-$T^{e2s}$-$T^{e2s}$-$G^{m1s}$-$T^{e2s}$-$G^{m1s}$-$T^{e2s}$-$T^{e2s}$-$G^{m1s}$-$A^{m1s}$-$CH_2CH_2OH$, wherein the left side represents the 5' end, and the right side represents the 3' end, A, G, C, U, and T respectively represent adenosine, guanosine, cytidine, uridine, and thymidine in which D-ribofuranose is modified and the carbon atom at the 5'-position is phosphorothioate-bound to the structural unit displayed on the left side, the e2s attached to each nucleotide or nucleoside indicates that D-ribofuranose is 2'-0,4'-C-ethylene-bridged, and the 3'-position binds to the carbon atom at the 5'-position of the nucleotide or nucleoside adjacent to the right side via —OP(═S)(—OH)—O—, the e2t attached thereto indicates that D-ribofuranose is 2'-O,4'-C-ethylene-bridged, and the 3'-position binds to the hydrogen atom at the 3' end via —O—, the mis attached thereto indicates that D-ribofuranose is 2'-O-methylated, and the 3'-position binds to the carbon atom at the 5'-position of the nucleotide or nucleoside adjacent to the right side via —OP(═S)(—OH)—O—, and the m1t attached thereto indicates that D-ribofuranose is 2'-O-methylated, and the 3'-position binds to the hydrogen atom at the 3' end via —O—;

(111) the method according to (109), wherein the oligonucleotide consists of a sequence represented by any one formula selected from GSD AO01 to GSD AO16 below, and the ligand is represented by $X^{18}$ or $X^{20}$ in the following formulas:

(SEQ ID NO: 16)
(GSDAO01) $X^{18}$-$A^{m1s}$-$A^{e2s}$-$g^{m1s}$-$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H;

(SEQ ID NO: 17)
(GSDAO02) $X^{18}$-$A^{e2s}$-$U^{m1s}$-$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1s}$-$C^{e2t}$-H;

(SEQ ID NO: 18)
(GSDAO03) $X^{18}$-$U^{m1s}$-$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{s2s}$-$G^{m1s}$-$C^{e2s}$-$U^{m1t}$-H;

-continued (SEQ ID NO: 19)
(GSDA004) $X^{18}$-$A^{m1s}$-$A^{m1s}$-$A^{e2s}$-$U^{m1s}$-$C^{m1s}$-$C^{e2s}$-
$G^{m1s}$-$A^{m1s}$-$T^{e2s}$-$G^{m1s}$-$G^{m1s}$-$C^{e2s}$-$G^{m1s}$-$A^{m1s}$-$A^{e2s}$
-$G^{m1t}$-H;

(SEQ ID NO: 20)
(GSDA005) $X^{18}$-$A^{m1s}$-$A^{e2s}$-$U^{m1s}$-$C^{m1s}$-$C^{e2s}$-$G^{m1s}$-
$A^{m1s}$-$T^{e2s}$-$G^{m1s}$-$G^{m1s}$-$C^{e2s}$-$G^{m1s}$-$A^{m1s}$-$A^{e2s}$-$G^{m1s}$
-$C^{e2t}$-H;

(SEQ ID NO: 21)
(GSDA006) $X^{18}$-$A^{e2s}$-$U^{m1s}$-$C^{m1s}$-$C^{e2s}$-$G^{m1s}$-$A^{m1s}$-
$T^{e2s}$-$G^{m1s}$-$G^{m1s}$-$C^{e2s}$-$G^{m1s}$-$A^{m1s}$-$A^{e2s}$-$G^{m1s}$-$C^{e2s}$
-$U^{m1t}$-H;

(SEQ ID NO: 22)
(GSDA007) $X^{18}$-$A^{m1s}$-$A^{e2s}$-$U^{m1s}$-$C^{m1s}$-$C^{e2s}$-$G^{m1s}$-
$A^{m1s}$-$U^{m1s}$-$G^{m1s}$-$G^{m1s}$-$C^{e2s}$-$G^{m1s}$-$A^{m1s}$-$A^{e2s}$-$G^{m1t}$
-H;

(SEQ ID NO: 23)
(GSDA008) $X^{18}$-$A^{e2s}$-$U^{m1s}$-$C^{m1s}$-$C^{e2s}$-$G^{m1s}$-$A^{e2s}$-
$U^{m1s}$-$G^{m1s}$-$G^{m1s}$-$C^{e2s}$-$G^{m1s}$-$A^{m1s}$-$A^{e2s}$-$G^{m1s}$-$C^{e2t}$
-H;

(SEQ ID NO: 24)
(GSDA009) $X^{18}$-$U^{m1s}$-$C^{m1s}$-$C^{e2s}$-$G^{m1s}$-$A^{e2s}$-$U^{m1s}$-
$G^{m1s}$-$G^{m1s}$-$C^{e2s}$-$G^{m1s}$-$A^{m1s}$-Ae25-$G^{m1s}$-$C^{e2s}$-$U^{m1t}$-
H;

(SEQ ID NO: 25)
(GSDA010) $X^{18}$-$A^{m1s}$-$A^{m1s}$-$A^{e2s}$-$U^{m1s}$-$c^{m1s}$-$C^{e2s}$-
$G^{m1s}$-$A^{e2s}$-$U^{m1s}$-$G^{m1s}$-$G^{m1s}$-$C^{e2s}$-$G^{m1s}$-$A^{m1s}$-$A^{e2s}$
-Gmt-H;

(SEQ ID NO: 26)
(GSDA011) $X^{18}$-$A^{m1s}$-$A^{e2s}$-$U^{m1s}$-$C^{m1s}$-$C^{e2s}$-$G^{m1s}$-
$A^{e2s}$-$U^{m1s}$-$G^{m1s}$-$G^{m1s}$-$C^{e2s}$-$G^{m1s}$-$A^{m1s}$-Ae23-$G^{m1s}$-
$C^{e2t}$-H1;

(SEQ ID NO: 27)
(GSDA012) $X^{18}$-$A^{e2s}$-$U^{m1s}$-$C^{m1s}$-$C^{e2s}$-$G^{m1s}$-$A^{e2s}$-
$U^{m1s}$-$G^{m1s}$-$G^{m1s}$-$C^{e2s}$-$G^{m1s}$-$A^{m1s}$-$A^{e2s}$-$G^{m1s}$-$C^{e2s}$
-$U^{m1t}$-H;

(SEQ ID NO: 28)
(GSDA013) $X^{20}$-$A^{m1s}$-$A^{e2s}$-$U^{m1s}$-$c^{m1s}$-$C^{e2s}$-$G^{m1s}$-
$A^{e2s}$-$U^{m1s}$-$G^{m1s}$-$G^{m1s}$-$C^{e2s}$-$G^{m1s}$-$A^{m1s}$-$A^{e2s}$-$G^{m1t}$
-H;

(SEQ ID NO: 29)
(GSDA014) $X^{20}$-$A^{e2s}$-$U^{m1s}$-$C^{m1s}$-$C^{e2s}$-$G^{m1s}$-$A^{e2s}$-
$U^{m1s}$-$G^{m1s}$-$c^{m1s}$-$C^{e2s}$-$G^{m1s}$-$A^{m1s}$-$A^{e2s}$-$G^{m1s}$-$C^{e2t}$-
H;

-continued (SEQ ID NO: 30)
(GSDA015) $X^{20}$-$A^{m1s}$-$A^{m1s}$-$A^{e2s}$-$U^{m1s}$-$C^{m1s}$-$C^{e2s}$-
$G^{m1s}$-$A^{e2s}$-$U^{m1s}$-$G^{m1s}$-$G^{m1s}$-$C^{e2s}$-$G^{m1s}$-$A^{m1s}$-$A^{e2s}$
-$G^{m1t}$-H;

and (SEQ ID NO: 31)
(GSDA016) $X^{20}$-$A^{m1s}$-$A^{e2s}$-$U^{m1s}$-$C^{m1s}$-$C^{e2s}$-$G^{m1s}$-
$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-
$C^{e2t}$-H, wherein the left side represents the 5' end, and the right side represents the 3' end, A, G, C, U, and T respectively represent adenosine, guanosine, cytidine, uridine, and thymidine in which D-ribofuranose is modified and the carbon atom at the 5'-position is phosphorothioate-bound to the structural unit displayed on the left side, the e2s attached to each nucleotide or nucleoside indicates that D-ribofuranose is 2'-0,4'-C-ethylene-bridged, and the 3'-position binds to the carbon atom at the 5'-position of the nucleotide or nucleoside adjacent to the right side via —OP(═S)(—OH)—O—, the e2t attached thereto indicates that D-ribofuranose is 2'-O,4'-C-ethylene-bridged, and the 3'-position binds to the hydrogen atom at the 3' end via —O—, the mis attached thereto indicates that D-ribofuranose is 2'-O-methylated, and the 3'-position binds to the carbon atom at the 5'-position of the nucleotide or nucleoside adjacent to the right side via —OP(═S)(—OH)—O—, the m1t attached thereto indicates that D-ribofuranose is 2'-O-methylated, and the 3'-position binds to the hydrogen atom at the 3' end via —O—, and $X^{18}$ and $X^{20}$ respectively represent GalNAc units represented by the following formulas, wherein the bond bound to the phosphate group indicates its bonding to the carbon atom at the 5' end of the oligonucleotide to form a phosphodiester bond:

[Formula 65]

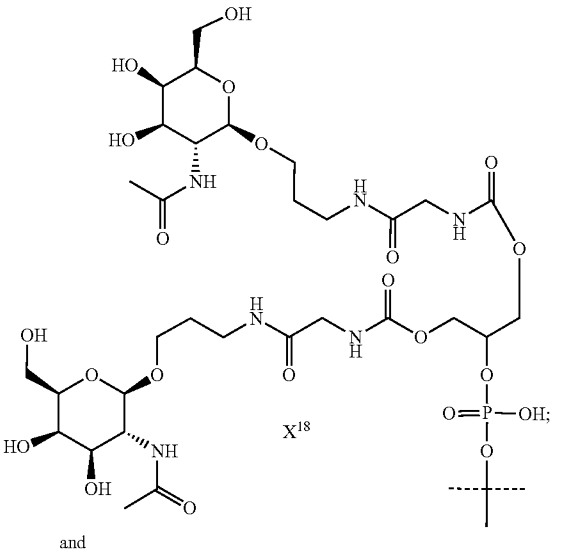

$X^{18}$ and

-continued

[Formula 66]

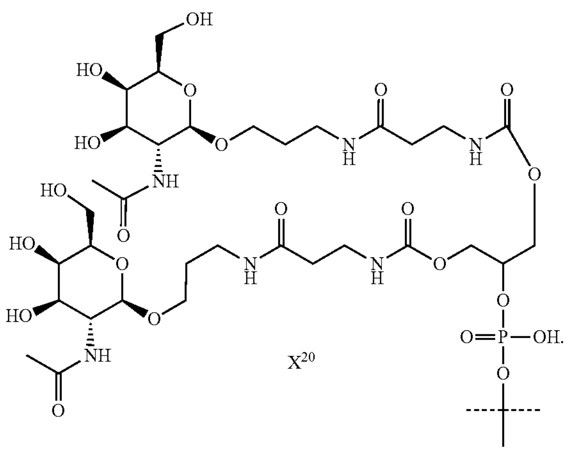

X[20]

ADVANTAGEOUS EFFECT OF INVENTION

The present invention enabled a plurality of ENA monomers to be separately produced, efficiently.

DESCRIPTION OF EMBODIMENTS

The present invention will be described further in detail.

In the present invention, the "protective group for a hydroxyl group" in $Z^1$ and $Z^2$ and the protective group for a "protected hydroxyl group" in the group α each refer to a protective group capable of being cleaved by a chemical method such as hydrogenolysis, hydrolysis, electrolysis, and photolysis, or a biological method such as hydrolysis in the human body. Examples of the protective group include: "aliphatic acyl groups" including alkylcarbonyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, and heneicosanoyl, carboxylated alkylcarbonyl groups such as succinoyl, glutaroyl, and adipoyl, halogeno-lower alkylcarbonyl groups such as chloroacetyl, dichloroacetyl, trichloroacetyl, and trifluoroacetyl, lower alkoxy lower alkylcarbonyl groups such as methoxyacetyl, and unsaturated alkylcarbonyl groups such as (E)-2-methyl-2-butenoyl; "aromatic acyl groups" including arylcarbonyl groups such as benzoyl, α-naphthoyl, and β-naphthoyl, halogeno-arylcarbonyl groups such as 2-bromobenzoyl and 4-chlorobenzoyl, lower alkylated arylcarbonyl groups such as 2,4,6-trimethylbenzoyl and 4-toluoyl, lower alkoxylated arylcarbonyl groups such as 4-anisoyl, carboxylated arylcarbonyl groups such as 2-carboxybenzoyl, 3-carboxybenzoyl, and 4-carboxybenzoyl, nitrated arylcarbonyl groups such as 4-nitrobenzoyl and 2-nitrobenzoyl, lower alkoxycarbonylated arylcarbonyl groups such as 2-(methoxycarbonyl)benzoyl, and arylated arylcarbonyl groups such as 4-phenylbenzoyl; "tetrahydropyranyl or tetrahydrothiopyranyl groups" such as tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl; "tetrahydrofuranyl or tetrahydrothiofuranyl groups" such as tetrahydrofuran-2-yl and tetrahydrothiofuran-2-yl; "silyl groups" including tri-lower alkylsilyl groups such as trimethylsilyl, triethylsilyl, isopropyldimethylsilyl, t-butyldimethylsilyl, methyldiisopropylsilyl, methyldi-t-butylsilyl, and triisopropylsilyl, tri-lower alkylsilyl groups substituted with one or two aryl groups such as diphenylmethylsilyl, diphenyl butylsilyl, diphenylisopropylsilyl, and phenyldiisopropylsilyl; "lower alkoxymethyl groups" such as methoxymethyl, 1,1-dimethyl-1-methoxymethyl, ethoxymethyl, propoxymethyl, isopropoxymethyl, butoxymethyl, and t-butoxymethyl; "lower alkoxylated lower alkoxymethyl groups" such as 2-methoxyethoxymethyl; "halogeno-lower alkoxymethyl" such as 2,2,2-trichloroethoxymethyl and bis(2-chloroethoxy)methyl; "lower alkoxyethyl groups" such as 1-ethoxyethyl and 1-(isopropoxy)ethyl; "ethyl halide groups" such as 2,2,2-trichloroethyl; "methyl groups substituted with 1 to 3 aryl groups" such as benzyl, α-naphthylmethyl, β-naphthylmethyl, diphenylmethyl, triphenylmethyl, α-naphthyldiphenylmethyl, and 9-anthril methyl; "methyl groups substituted with 1 to 3 aryl groups in which each aryl ring is substituted with a lower alkyl, lower alkoxy, halogen, or cyano group" such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl, and 4-cyanobenzyl; "lower alkoxycarbonyl groups" such as methoxycarbonyl, ethoxycarbonyl, t-butoxycarbonyl, and isobutoxycarbonyl; "lower alkoxycarbonyl groups substituted with a halogen or a tri-lower alkylsilyl group" such as 2,2,2-trichloroethoxycarbonyl, and 2-trimethylsilylethoxycarbonyl; "alkenyloxycarbonyl groups" such as vinyloxycarbonyl and aryloxycarbonyl; and "aralkyloxycarbonyl groups in which the aryl ring is optionally substituted with one or two lower alkoxy or nitro groups" such as benzyloxycarbonyl, 4-methoxybenzyloxycarbonyl, 3,4-dimethoxybenzyloxycarbonyl, 2-nitrobenzyloxycarbonyl, and 4-nitrobenzyloxycarbonyl.

The "protective group for a hydroxyl group" in $Z^1$ and $Z^2$ is preferably one of the "aliphatic acyl group", "aromatic acyl group", "methyl group substituted with 1 to 3 aryl groups", "methyl group substituted with 1 to 3 aryl groups in which each aryl ring is substituted with a lower alkyl, lower alkoxy, halogen, or cyano group", or "silyl group", more preferably an acetyl group, a benzoyl group, a benzyl group, a p-methoxybenzoyl group, a dimethoxytrityl group, a monomethoxytrityl group, or a t-butyldiphenylsilyl group, even more preferably a benzyl group.

In the "protected hydroxyl group" in the group α, the protective group is one of the "aliphatic acyl group" or "aromatic acyl group", more preferably a benzoyl group.

In the present invention, the "lower alkyl group" in A, $R^1$, and the group α represents a linear or branched alkyl group having 1 to 6 carbon atoms, and examples thereof include a methyl group, an ethyl group, a n-propyl group, an isopropyl group, a n-butyl group, an isobutyl group, a s-butyl group, a t-butyl group, a n-pentyl group, an isopentyl group, a 2-methylbutyl group, a neopentyl group, a 1-ethylpropyl group, a n-hexyl group, an isohexyl group, a 4-methylpentyl group, a 3 -methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, and a 2-ethylbutyl group.

The "lower alkyl group" in A is preferably a methyl group, an ethyl group, or a propyl group, more preferably a methyl group.

The "lower alkyl group" in $R^1$ is preferably a methyl group.

In the present invention, the "lower alkoxy group" in the group α represents a group in which the "lower alkyl group" is bound to an oxygen atom, and examples thereof include methoxy, ethoxy, n-propoxy, isopropoxy, n-butoxy, isobutoxy, s-butoxy, and t-butoxy groups, preferably a methoxy or ethoxy group.

In the present invention, examples of the protective group for "protected mercapto groups" in the group α include "groups that form disulfides" including alkylthio groups such as methylthio, ethylthio, and t-butylthio groups, and arylthio groups such as a benzylthio group, as well as those described as protective groups for a hydroxyl group, preferably "aliphatic acyl groups" or "aromatic acyl groups", more preferably a benzoyl group.

In the present invention, the "lower alkylthio group" in the group a represents a group in which the "lower alkyl group" is bound to a sulfur atom, and examples thereof include methylthio, ethylthio, propylthio, isopropylthio, butylthio, isobutylthio, s-butylthio, and t-butylthio groups, preferably a methylthio or ethylthio group.

In the present invention, examples of the protective group for "protected amino groups" in the group α include: "aliphatic acyl groups" including alkylcarbonyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, and heneicosanoyl groups, carboxylated alkylcarbonyl groups such as succinoyl, glutaroyl, and adipoyl groups, halogeno-lower alkylcarbonyl groups such as chloroacetyl, dichloroacetyl, trichloroacetyl, and trifluoroacetyl groups, lower alkoxy lower alkylcarbonyl groups such as a methoxyacetyl group, and unsaturated alkylcarbonyl groups such as an (E)-2-methyl-2-butenoyl group; "aromatic acyl groups" including arylcarbonyl groups such as benzoyl, α-naphthoyl, and β-naphthoyl groups, halogeno-arylcarbonyl groups such as 2-bromobenzoyl and 4-chlorobenzoyl groups, lower alkylated arylcarbonyl groups such as 2,4,6-trimethylbenzoyl and 4-toluoyl, lower alkoxylated arylcarbonyl groups such as a 4-anisoyl group, carboxylated arylcarbonyl groups such as 2-carboxybenzoyl, 3-carboxybenzoyl, and 4-carboxybenzoyl groups, nitrated arylcarbonyl groups such as 4-nitrobenzoyl and 2-nitrobenzoyl groups, lower alkoxycarbonylated arylcarbonyl groups such as a 2-(methoxycarbonyl) benzoyl group, and arylated arylcarbonyl groups such as a 4-phenylbenzoyl group; "lower alkoxycarbonyl groups" such as methoxycarbonyl, ethoxycarbonyl, t-butoxycarbonyl, and isobutoxycarbonyl groups; "lower alkoxycarbonyl groups substituted with a halogen or a tri-lower alkylsilyl group" such as 2,2,2-trichloroethoxycarbonyl and 2-trimethylsilylethoxycarbonyl groups; "alkenyloxycarbonyl groups" such as vinyloxycarbonyl and aryloxycarbonyl groups; "aralkyloxycarbonyl groups in which the aryl ring is optionally substituted with one or two lower alkoxy or nitro groups" such as benzyloxycarbonyl, 4-methoxybenzyloxycarbonyl, 3,4-dimethoxybenzyloxycarbonyl, 2-nitrobenzyloxycarbonyl, and 4-nitrobenzyloxycarbonyl groups, preferably an "aliphatic acyl group" or an "aromatic acyl group", more preferably a benzoyl group.

In the present invention, the "lower alkylamino group" in the group α represents a group in which one or two hydrogen atoms of the amino group are each replaced with the "lower alkyl group", and examples thereof include methylamino, ethylamino, propylamino, isopropylamino, butylamino, isobutylamino, s-butylamino, t-butylamino, dimethylamino, diethylamino, dipropylamino, diisopropylamino, dibutylamino, diisobutylamino, di(s-butyl)amino, and di(t-butyl) amino groups, preferably a methylamino, ethylamino, dimethylamino, diethylamino, or diisopropylamino group.

In the present invention, examples of the "halogen atom" in $X^1$, $X^2$, and the group α include a fluorine atom, a chlorine atom, a bromine atom, and an iodine atom.

In the present invention, examples of the "group that forms a leaving group" in $X^1$ and $X^2$ include a halogen atom, aliphatic acyloxy groups, halogen-substituted lower alkylimidoxy groups, and halogen-substituted lower alkylsulfonyloxy groups.

The "group that forms a leaving group" in $X^1$ is preferably an iodine atom, an acetoxy group, or a trichloroacetimidoxy group.

The "group that forms a leaving group" in $X^2$ is preferably an acetoxy group.

In the present invention, examples of the "methyl group substituted with 1 to 3 aryl groups" in Y include benzyl, α-naphthylmethyl, β-naphthylmethyl, diphenylmethyl, trityl, α-naphthyldiphenylmethyl, and 9-anthrilmethyl groups, preferably a trityl group.

In the present invention, examples of the "methyl group substituted with 1 to 3 aryl groups in which each aryl ring is substituted with a lower alkyl, lower alkoxy, halogen, or cyano group" in Y include 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl(4,4'-dimethoxytrityl), 2-nitrobenzyl, 4-nitrobenzyl, 4-chlorobenzyl, 4-bromobenzyl, and 4-cyanobenzyl groups.

In the present invention, the "lower alkoxymethyl group" in Y is a group in which a methyl group is bound to the "lower alkoxy group". Examples thereof include methoxymethyl, 1,1-dimethyl-1-methoxymethyl, ethoxymethyl, propoxymethyl, isopropoxymethyl, butoxymethyl, and t-butoxymethyl groups, preferably a methoxymethyl group.

In the present invention, examples of the "tetrahydropyranyl group" in Y include tetrahydropyran-2-yl, 3-bromotetrahydropyran-2-yl, and 4-methoxytetrahydropyran-4-yl groups, preferably a tetrahydropyran-2-yl group.

In the present invention, examples of the "silyl group" in Y include tri-lower alkylsilyl groups such as trimethylsilyl, triethylsilyl, isopropyldimethylsilyl, t-butyldimethylsilyl, methyldiisopropylsilyl, methyldi-t-butylsilyl, and triisopropylsilyl groups, and tri-lower alkylsilyl groups substituted with one or two aryl groups such as diphenylmethylsilyl, diphenyl butylsilyl, diphenylisopropylsilyl, and phenyldiisopropylsilyl groups, preferably a t-butyldiphenylsilyl group or a t-butyldimethylsilyl group.

The "trityl group optionally substituted with 1 to 3 lower alkoxy groups" in $P^1$ represents a group in which 1 to 3 hydrogen atoms of the phenyl group in the trityl group are each replaced with the "lower alkoxy group", and examples thereof include a trityl group, a monomethoxytrityl group, or a dimethoxytrityl group, preferably a 4,4'-dimethoxytrityl group.

In the present invention, examples of the "aliphatic acyl group" in R, $R^3$, $R^4$, $R^6$, and $Z^3$ include alkylcarbonyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, and heneicosanoyl groups, carboxylated alkylcarbonyl groups such as succinoyl, glutaroyl, and adipoyl groups, halogeno-lower alkylcarbonyl groups such as chloroacetyl, dichloroacetyl, trichloroacetyl, and trifluoroacetyl groups, lower alkoxy lower alkylcarbonyl groups such as a methoxyacetyl group, and unsaturated alkylcarbonyl groups such as an (E)-2-methyl-2-butenoyl group.

The "aliphatic acyl group" in R, $R^3$, $R^6$ and $Z^3$ is preferably an acetyl group.

The "aliphatic acyl group" in $R^4$ is preferably an isobutyryl group.

In the present invention, examples of the "aromatic acyl group" in $R^3$, $R^4$, $R^6$, and $Z^3$ include arylcarbonyl groups such as benzoyl, α-naphthoyl, and β-naphthoyl groups, halogeno-arylcarbonyl groups such as 2-bromobenzoyl and 4-chlorobenzoyl groups, lower alkylated arylcarbonyl groups such as 2,4,6-trimethylbenzoyl and 4-toluoyl groups, lower alkoxylated arylcarbonyl groups such as a 4-anisoyl group, carboxylated arylcarbonyl groups such as 2-carboxybenzoyl, 3-carboxybenzoyl, and 4-carboxybenzoyl groups, nitrated arylcarbonyl groups such as 4-nitrobenzoyl and 2-nitrobenzoyl groups, lower alkoxycarbonylated arylcarbonyl groups such as a 2-(methoxycarbonyl)benzoyl group, and arylated arylcarbonyl groups such as a 4-phenylbenzoyl group.

The "aromatic acyl group" in $R^3$, $R^4$, $R^6$, and $Z^3$ is preferably a benzoyl group.

In the present invention, the "amino group protected by an aliphatic acyl group or an aromatic acyl group" in $R^2$ represents a group in which an amino group is substituted with the "aliphatic acyl group" or "aromatic acyl group". Examples of the "amino group protected by an aliphatic acyl group" in $R^2$ include formylamino, acetylamino, propionylamino, butyrylamino, isobutyrylamino, pentanoylamino, pivaloylamino, valerylamino, chloroacetylamino, dichloroacetylamino, trichloroacetylamino, trifluoroacetylamino, methoxyacetylamino, and (E)-2-methyl-2-butenoylamino groups. Examples of the "amino group protected by an aromatic acyl group" in $R^2$ include benzoylamino, α-naphthoylamino, β-naphthoylamino, 2-bromobenzoylamino, 4-chlorobenzoylamino, 2,4,6-trimethylbenzoylamino, 4-toluoylamino, 4-anisoylamino, 2-carboxybenzoylamino, 3-carboxybenzoylamino, 4-carboxybenzoylamino, 4-nitrobenzoylamino, 2-nitrobenzoylamino, 2-(methoxycarbonyl)benzoylamino, and 4-phenylbenzoylamino groups, preferably a benzoylamino group.

In the present invention, examples of the "benzyl group optionally substituted with a lower alkyl, lower alkoxy, halogen, or cyano group" in $R^5$ include benzyl, 4-methylbenzyl, 2,4,6-trimethylbenzyl, 3,4,5-trimethylbenzyl, 4-methoxybenzyl, 4-chlorobenzyl, 4-bromobenzyl, and 4-cyanobenzyl groups, preferably a benzyl group.

In formulas (XXVII) and (XXVIII) above, the "purin-9-yl group optionally having one or more substituents selected from the group α" in B is preferably a 6-aminopurin-9-yl (that is, adeninyl), amino group-protected 6-aminopurin-9-yl, 2,6-diaminopurin-9-yl, 2-amino-6-chloropurin-9-yl, 2-amino-6-fluoropurin-9-yl, amino group-protected 2-amino-6-fluoropurin-9-yl, 2-amino-6-bromopurin-9-yl, amino group-protected 2-amino-6-bromopurin-9-yl, 2-amino-6-hydroxypurin-9-yl (that is, guaninyl), amino group-protected 2-amino-6-hydroxypurin-9-yl, 2-amino-6-hydroxypurin-9-yl with an amino group and a hydroxyl group protected, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-9-yl, or 6-mercaptopurin-9-yl group, more preferably an amino group-protected 6-aminopurin-9-yl group or an amino group-protected 2-amino-6-hydroxypurin-9-yl group, even more preferably a 6-benzoylaminopurin-9-yl or 2-isobutyrylamino-6-hydroxypurin-9-yl group.

In formulas (XXVII) and (XXVIII) above, the "2-oxo-pyrimidin-1-yl group optionally having one or more substituents selected from the group α" in B is preferably a 2-oxo-4-amino-pyrimidin-1-yl (that is, cytosinyl), amino group-protected 2-oxo-4-amino-pyrimidin-1-yl, 2-oxo-4-amino-5-fluoro-pyrimidin-1-yl, amino group-protected 2-oxo-4-amino-5-fluoro-pyrimidin-1-yl, 4-amino-2-oxo-5-chloro-pyrimidin-1-yl, 2-oxo-4-methoxy-pyrimidin-1-yl, 2-oxo-4-mercapto-pyrimidin-1-yl, 2-oxo-4-hydroxy-pyrimidin-1-yl (that is, uracinyl), 2-oxo-4-hydroxy-5-methylpyrimidin-1-yl (that is, thyminyl), 4-amino-5-methyl-2-oxo-pyrimidin-1-yl (that is, 5-methylcytosinyl), or amino group-protected 4-amino-5 -methyl-2-oxo-pyrimidin-1-yl group, more preferably a 2-oxo-4-hydroxy-5-methylpyrimidin-1-yl group, an amino group-protected 2-oxo-4-amino-pyrimidin-1-yl group, or an amino group-protected 4-amino-5-methyl-2-oxo-pyrimidin-1-yl group, even more preferably a 2-oxo-4-hydroxy-5-methylpyrimidin-1-yl group, a 2-oxo-4-benzoylamino-pyrimidin-1-yl group, or a 4-benzoylamino-5-methyl-2-oxo-pyrimidin-1-yl group.

In the present invention, n is an integer of 0 to 4, preferably 0 or 1, more preferably 1.

The "salt thereof" refers to a salt that can be formed by the compound of the present invention, and preferable examples of the salt thereof include metal salts including alkali metal salts such as sodium salts, potassium salts, and lithium salts, alkaline earth metal salts such as calcium salts and magnesium salts, aluminum salts, iron salts, zinc salts, copper salts, nickel salts, and cobalt salts; amine salts including inorganic salts such as ammonium salts, and organic salts such as t-octylamine salts, dibenzyl amine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethyl amine salts, piperazine salts, tetramethyl ammonium salts, tris(hydroxymethyl)aminomethane salts; inorganic acid salts including hydrohalides such as hydrofluorates, hydrochlorides, hydrobromides, and hydroiodides, nitrates, perchlorates, sulfates, and phosphates; organic acid salts such as lower alkane sulfonates such as methanesulfonates, trifluoromethanesulfonates, and ethanesulfonates, aryl sulfonates such as benzene sulfonates and p-toluenesulfonates, acetates, malates, fumarates, succinates, citrates, tartrates, oxalates, and maleates; and amino acid salts such as glycine salts, lysine salts, arginine salts, ornithine salts, glutamates, and aspartates.

In the present invention, the carbonyl group of a thymine derivative or a guanine derivative can be a "tautomer". A tautomer is one of two or more structural isomers that exist in equilibrium, easily converted from an isomer into another isomer, and exists as a mixture of a tautomer pair in a solution. Under conditions where tautomerization is possible, the chemical equilibrium of tautomers is reached, but the exact ratio depends on several factors including the temperature, the solvent, and the pH. The concept of tautomers that can be transformed into each other by tautomerization is called tautomerism.

Examples of the amide-imide acid tautomer in a thymine derivative and a guanine derivative are as shown below.

[Formula 67]

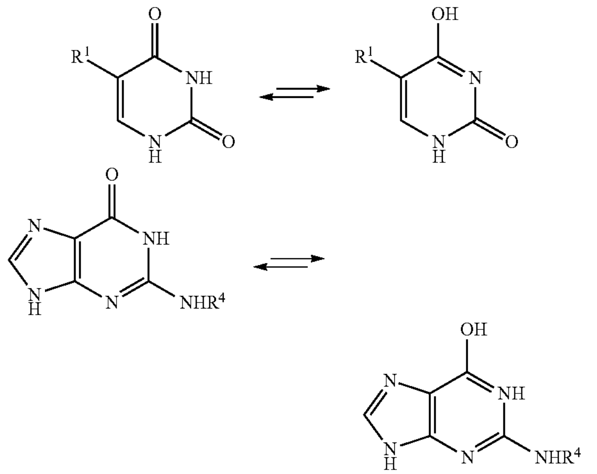

In the present invention, the "protection reagent for a hydroxyl group" refers to a reagent used for introducing the "protective group for a hydroxyl group" into a hydroxyl group of a nucleoside analog and its production intermediate. For example, in the case where the "protective group for a hydroxyl group" is:

(1) a benzyl group, examples thereof include benzyl chloride, benzyl bromide, benzyl iodide, and benzyl trichloroacetoimidate, (2) a trityl group, examples thereof include trityl chloride and trityl trifluorosulfonate, (3) a t-butyldimethylsilyl group, examples thereof include t-butyldimethylsilyl chloride, or (4) an acetyl group, examples thereof include acetic anhydride and acetyl chloride.

In the present invention, the "protection reagent for a primary hydroxyl group" refers to a reagent used for introducing the "trityl group optionally substituted with 1 to 3 lower alkoxy groups" into the sugar hydroxyl group at the 5-position of a nucleoside analog, and examples thereof include trityl chloride, trityl trifluorosulfonate, 4-monomethoxytrityl chloride, 4,4'-dimethoxytrityl chloride, and 4,4'-dimethoxytrityl trifluorosulfonate, preferably 4,4'-dimethoxytrityl chloride.

In the present invention, the "deprotection reagent for a hydroxyl group" refers to a reagent to be added for removing the "protective group for a hydroxyl group". For example, in the case of the "protective group for a hydroxyl group" is:

(1) a benzyl group, examples thereof include metal catalysts such as palladium, palladium hydroxide, and platinum, reducing agents such as hydrogen, formic acid, and ammonium formate, iron (III) chloride, and boron trichloride, (2) a trityl group, examples thereof include acid catalysts such as sulfuric acid, p-toluenesulfonic acid, and methanesulfonic acid, or (3) an acetyl group, examples thereof include inorganic bases such as sodium hydroxide, potassium hydroxide, and sodium carbonate, and organic bases such as ammonia and alkylamine.

In the present invention, the metal catalyst can be a metal catalyst supported or not supported on a carrier (preferably, carbon), preferably a metal catalyst supported on carbon (preferably palladium, palladium hydroxide, or platinum supported on carbon, more preferably palladium supported on carbon).

In the present invention, the "acylating agent" refers to a reagent used for introducing the "protective group for an amino group" into an amino group of a nucleoside analog. For example, in the case of:

(1) an acetyl group, examples thereof include acetic anhydride and acetyl chloride, (2) a benzoyl group, examples thereof include benzoyl chloride, benzoic anhydride, and benzoic acid, or (3) an isobutyryl group, examples thereof include isobutyl chloride isobutyric anhydride.

In the present invention, the "aminating agent" refers to a reagent used for replacing the chlorine atom at the 6-position of the purine ring or the carbonyl group at the 4-position of a pyrimidine ring with an amino group, and examples thereof include ammonia, an aqueous ammonia solution or ammonium carbonate, and ammonia salts such as ammonium acetate, preferably an aqueous ammonia solution.

In the present invention, the "amidating agent" refers to a reagent used for converting the chlorine atom at the 6-position of the purine ring into an aliphatic amide or an aromatic amide in the cross-coupling reaction, and examples thereof include acetyl amide, benzoyl amide, and isobutyl amide, preferably isobutyl amide.

In the present invention, the "activator" in the glycosylation reaction refers to a reagent used for converting the hydroxyl group at the 1-position of the sugar into the "group that forms a leaving group", and examples thereof include acetic anhydride, benzoic anhydride, trichloroacetonitrile, carbonyldiimidazole, and diphenyl chlorophosphate, preferably acetic anhydride or trichloroacetonitrile.

In the present invention, the "halogenating agent" in the glycosylation reaction refers to a reagent used for halogenating the "group that forms a leaving group" in order for the glycosylation reaction to proceed stereoselectively, and examples thereof include chlorotrimethylsilane (TMSCl), bromotrimethylsilane (TMSBr), and iodotrimethylsilane (TMSI), preferably TMSI.

In the present invention, the "activator" in the amination reaction refers to a reagent used for converting a hydroxyl group into a leaving group, and examples thereof include p-toluenesulfonyl chloride and 2,4,6-triisopropylbenzenesulfonyl chloride, preferably 2,4,6-triisopropylbenzenesulfonyl chloride.

In the present invention, the "activator" in the amidite-forming reaction refers to a reagent used for forming an active intermediate of the amidite reagent, and examples thereof include 5-benzylthiotetrazole, 5-phenyltetrazole, dibromoimidazole, dicyanoimidazole, and N-alkylimidazole trifluoroacetate, preferably 4,5-dicyanoimidazole. The amount of the activator to be used is 0.01 to 1.0 equivalent, preferably 0.1 to 0.5 equivalents, with respect to the compound of formula (XXVII).

In the present invention, the "amidite-forming reagent" in the amidite-forming reaction refers to a reagent used for introducing a group containing a phosphorus atom useful for forming a bond between nucleosides into the sugar hydroxyl group at the 3-position of a nucleoside analog, and examples thereof include 2-cyanoethyl N,N,N',N'-tetraisopropyl phosphorodiamidite and 2-cyanoethyldiisopropyl chlorophosphoramidite, preferably 2-cyanoethyl N,N,N',N'-tetraisopropyl phosphorodiamidite. The amount of the amidite-forming reagent to be used is 1.0 to 1.5 equivalent, preferably 1.1 to 1.3 equivalent, with respect to the compound of formula (XXVII).

In the present invention, the "drying agent" in the amidite-forming reaction is a reagent used for absorbing water in the reaction solution, and examples thereof include molecular sieve 3A, molecular sieve 4A, and molecular sieve 5A, preferably molecular sieve 4A.

The compound (2A) of the present invention can be produced by method A described below.

(Method A)

[Formula 68]

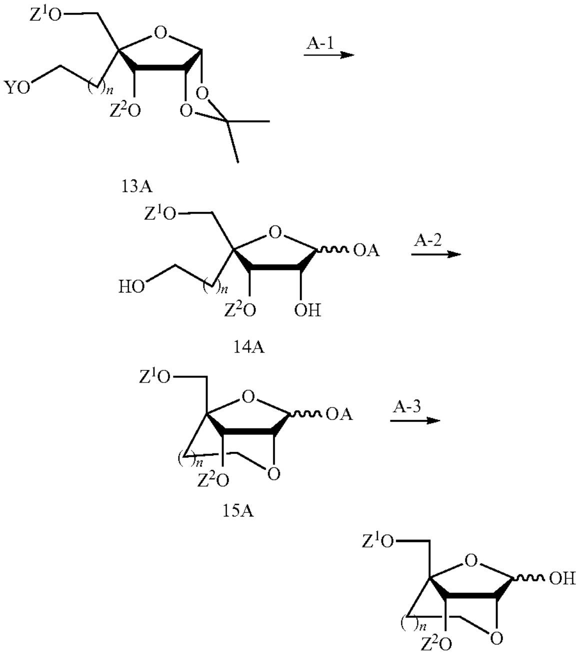

13A
14A
15A
2A

In method A, A, Y, $Z^1$, and $Z^2$ have the same meanings as above. $Z^1$ and $Z^2$ each represent a protective group for a hydroxyl group that is stable under the Y deprotection conditions.

Hereinafter, each step of method A will be described in detail.

(Step A-1)

This step is a step of deprotecting Y and the protective groups for hydroxyl groups at the 1-and 2-positions of a compound (13A) that can be produced by method C and method D, which will be described below, in an alcohol solvent in the presence of an acid catalyst, to produce a compound (14A). In the case of n=0, this step may be omitted, and step A-2 may be performed using a compound (14A') to be produced by method B, which will be described below.

Examples of the alcohol solvent to be used include alcohols such as methanol, ethanol, and propanol, preferably methanol.

Examples of the acid catalyst to be used include sulfuric acid, p-toluenesulfonic acid, and methanesulfonic acid, preferably sulfuric acid.

The reaction temperature is generally 0° C. to 100° C., preferably 40 to 60° C.

The reaction time differs depending on the type and the amount of the acid catalyst to be used but is generally 1 hour to 48 hours, preferably 10 hours to 24 hours.

After completion of the reaction, an alcohol solution of the target compound (14A) of this reaction is obtained, for example, by neutralizing the reaction solution with triethylamine, adding water thereto to crystallize methoxytriphenyl methane as a co-product, and filtering it out to separate a hydroalcoholic solution containing the target compound. Water and toluene are added to the hydroalcoholic solution following further washing with n-heptane for separation, and a toluene solution obtained by concentrating the organic layer obtained above can be used for the following step, as it is.

The compound obtained can be further purified by conventional methods such as recrystallization and silica gel chromatography, if necessary.

(Step A-2)

This step is a step of cyclizing the diol moiety of the compound (14A) produced in step A-1 in a solvent using a trivalent phosphorus reagent and an azodicarboxylate ester, to produce a compound (15A).

Examples of the solvent to be used include hydrocarbon halides such as methylene chloride, chloroform, and 1,2-dichloroethane, hydrocarbons such as benzene and toluene, and ethers such as tetrahydrofuran and dimethyl ether, preferably toluene.

Examples of the trivalent phosphorus reagent to be used include triphenylphosphine and tri(n-butyl)phosphine, preferably triphenylphosphine.

Examples of the azodicarboxylate ester to be used include diethyl azodicarboxylate, diisopropyl azodicarboxylate, and di t-butyl azodicarboxylate, preferably diisopropyl azodicarboxylate.

The reaction temperature is generally 0° C. to 50° C., preferably 10 to 40° C.

The reaction time differs depending on the type and the amount of the trivalent phosphorus reagent to be used but is generally 1 hour to 24 hours, preferably 1 hour to 3 hours.

After completion of the reaction, a toluene solution of the target compound (15A) of this reaction can be obtained, for example, by adding magnesium chloride to the reaction solution, followed by stirring, to form a poorly soluble phosphine complex and removing phosphine oxide as a co-product by filtration. Further, hydrazine diester as another co-product can also be effectively removed by washing the toluene layer with methanol water. A toluene solution obtained by concentrating the organic layer obtained can be used for the following step, as it is.

The compound obtained can be further purified by conventional methods such as recrystallization and silica gel chromatography, if necessary.

(Step A-3)

This step is a step of allowing an acid to act in a solvent and hydrolyzing the anomer position of the compound (15A) produced in step A-2, to produce a compound (2A).

Examples of the solvent to be used include water-soluble solvents such as acetic acid, water, and alcohol, hydrocarbon halides such as methylene chloride, chloroform, and 1,2-dichloroethane, hydrocarbons such as benzene and toluene, and ethers such as tetrahydrofuran and dimethyl ether, preferably acetic acid.

Examples of the acid to be used include hydrochloric acid, sulfuric acid, trifluoroacetic acid, methanesulfonic acid, and p-toluenesulfonic acid, preferably hydrochloric acid.

The reaction temperature is generally 0° C. to 50° C., preferably 20 to 30° C.

The reaction time differs depending on the type and the amount of the acid to be used but is generally 1 hour to 24 hours, preferably 1 hour to 3 hours.

After completion of the reaction, the target compound (2A) of this reaction can be crystallized, for example, by adding water to the reaction solution, followed by cooling and then stirring.

The compound obtained can be further purified by conventional methods such as recrystallization and silica gel chromatography, if necessary.

The compound (14A) (in the case of n=0) can be produced by method B described below.

(Method B)

[Formula 69]

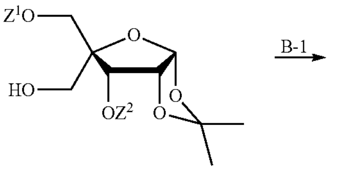

1B

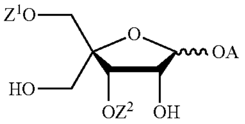

14A'

In method B, A, $Z^1$, and $Z^2$ have the same meanings as above.

Hereinafter, the process of method B will be described in detail.

(Step B-1)

This step is a step of producing the compound (14A') using a compound (1B) produced according to the method for producing a compound (7) of International Publication No. WO 00/47599. The compound (14A') can be produced by deprotecting the protective groups for hydroxyl groups at the 1-and 2-positions of the compound (1B) according to step A-1 of method A.

The compound (13A) (in the case of n=1) can be produced by method C described below.

(Method C)

[Formula 70]

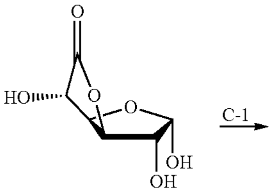

4

-continued

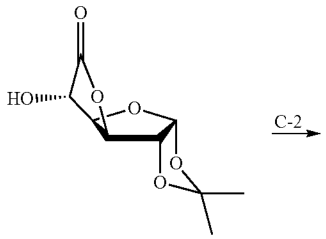

5

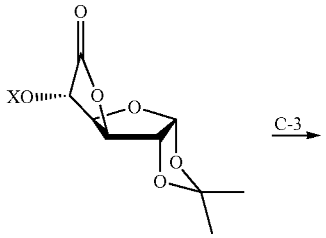

6

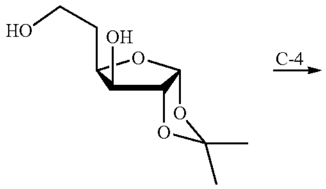

7

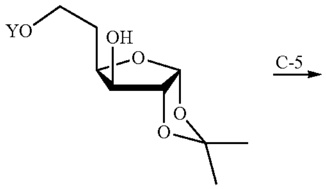

8

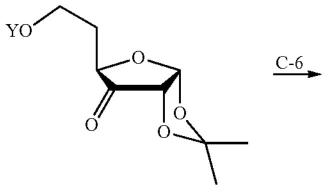

9

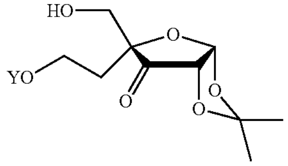

+

10

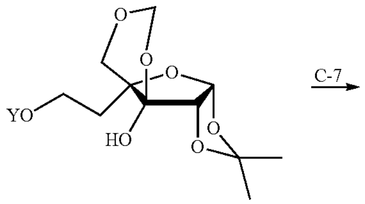

11

-continued

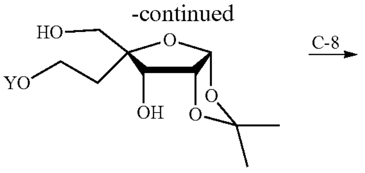

12

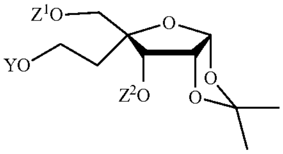

13

In method C, X represents a group that forms a leaving group together with an oxygen atom. Y, $Z^1$, and $Z^2$ have the same meanings as above.

Examples of X include lower alkylsulfonyl groups such as methanesulfonyl and ethanesulfonyl groups, halogen-substituted lower alkylsulfonyl groups such as a trifluoromethanesulfonyl group, aryl sulfonyl groups such as a p-toluenesulfonyl group, preferably a methanesulfonyl group or a p-toluenesulfonyl group.

Hereinafter, each step of method C will be described in detail.

(Step C-1)

This step is a step of reacting a compound (4) in an acetone solvent in the presence of an acid catalyst, to produce a compound (5).

Examples of the acid catalyst to be used include sulfuric acid, p-toluenesulfonic acid, and methanesulfonic acid, preferably sulfuric acid.

The reaction temperature differs depending on the acid catalyst to be used but is generally 0° C. to 50° C., preferably 30 to 40° C.

The reaction time differs depending on the type and the amount of the acid catalyst to be used but is generally 10 minutes to 24 hours, preferably 10 hours to 20 hours.

After completion of the reaction, the target compound (5) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

(Step C-2)

This step is a step of reacting a leaving group-introducing reagent with the compound (5) produced in step C-1 in a solvent in the presence of a base, to produce a compound (6).

Examples of the solvent to be used include amides such as dimethylacetamide and dimethylformamide, hydrocarbon halides such as methylene chloride, chloroform, and 1,2-dichloroethane, hydrocarbons such as benzene and toluene, ethers such as tetrahydrofuran and dimethyl ether, and esters such as methyl acetate, ethyl acetate, and propyl acetate, preferably dimethylacetamide.

Examples of the base to be used include bases such as triethylamine, pyridine, dimethylaminopyridine, and 1-methylimidazole, preferably 1-methylimidazole.

Examples of the leaving group-introducing reagent to be used include p-toluenesulfonyl chloride, methanesulfonyl chloride, and trifluoromethanesulfonic anhydride, preferably p-toluenesulfonyl chloride.

The reaction temperature differs depending on the leaving group-introducing reagent to be used but is generally 0° C. to 50° C., preferably 20 to 30° C.

The reaction time differs depending on the type and the amount of the leaving group-introducing reagent to be used but is generally 10 minutes to 24 hours, preferably 1 hour to 5 hours.

After completion of the reaction, the target compound (6) of this reaction is obtained, for example, by adding water to the reaction solution for crystallization.

The compound obtained can be further purified by conventional methods such as recrystallization and silica gel chromatography, if necessary.

(Step C-3)

This step is a step of reacting a hydride reducing agent with the compound (6) produced in step C-2 in a solvent, to produce a compound (7).

Examples of the solvent to be used include hydrocarbon halides such as methylene chloride, chloroform, and 1,2-dichloroethane, hydrocarbons such as benzene and toluene, and ethers such as tetrahydrofuran and dimethyl ether, preferably tetrahydrofuran.

Examples of the hydride reducing agent to be used include sodium bis(2-methoxyethoxy)aluminum hydride, lithium aluminum hydride, and diisobutylaluminum hydride, preferably sodium bis(2-methoxyethoxy)aluminum hydride.

The reaction time differs depending on the type and the amount of the hydride reducing agent to be used but is generally 10 minutes to 24 hours, preferably 1 hour to 3 hours.

After completion of the reaction, the target compound (7) of this reaction is obtained, for example, by adding acetone and an aqueous L-potassium sodium tartrate solution to the reaction solution, then separating an organic layer containing the target compound, washing it with water, and then distilling off the solvent.

The compound obtained can be further purified by conventional methods such as recrystallization and silica gel chromatography, if necessary.

(Step C-4)

This step is a step of introducing a protective group selectively into a primary hydroxyl group of the compound (7) produced in step C-3 in a solvent in the presence of a base, to produce a compound (8).

Examples of the solvent to be used include amides such as dimethylacetamide and dimethylformamide, hydrocarbons such as benzene and toluene, hydrocarbon halides such as methylene chloride, chloroform, and 1,2-dichloroethane, ethers such as tetrahydrofuran and dimethyl ether, and esters such as methyl acetate, ethyl acetate, and propyl acetate, preferably toluene.

Examples of the base to be used include bases such as triethylamine, pyridine, dimethylaminopyridine, 1-methylimidazole, and 4-methylmorpholine, preferably 4-methylmorpholine.

Examples of the protection reagent for a primary hydroxyl group to be used include trityl chloride and 4,4'-dimethoxytrityl chloride, preferably trityl chloride.

The reaction temperature differs depending on the protection reagent to be used but is generally 0° C. to 50° C., preferably 20 to 30° C.

The reaction time differs depending on the type and the amount of the protection reagent for a primary hydroxyl group to be used but is generally 10 minutes to 24 hours, preferably 1 hour to 5 hours.

After completion of the reaction, the target compound (8) of this reaction is obtained, for example, by adding water to the reaction solution, separating an organic layer containing the target compound, washing it with water, and then distilling off the solvent.

The compound obtained can be further purified by conventional methods such as recrystallization and silica gel chromatography, if necessary.

(Step C-5)

This step is a step of oxidizing the secondary hydroxyl group at the 3-position of the compound (8) produced in step C-4 in a solvent in the presence of a base, an oxidizing agent, an oxidation catalyst, and a co-catalyst, to produce a compound (9).

Examples of the solvent to be used include amides such as dimethylacetamide and dimethylformamide, hydrocarbons such as benzene and toluene, hydrocarbon halides such as methylene chloride, chloroform, and 1,2-dichloroethane, ethers such as tetrahydrofuran and dimethyl ether, and esters such as methyl acetate, ethyl acetate, and propyl acetate, preferably toluene.

Examples of the base to be used include inorganic bases such as sodium hydroxide, potassium hydroxide, sodium bicarbonate, and sodium carbonate, and organic bases such as triethylamine, pyridine, dimethylaminopyridine 1-methylimidazole, and 4-methylmorpholine, preferably sodium bicarbonate.

Examples of the oxidation catalyst to be used include 2,2,6,6-tetramethylpiperidine 1-oxyl, 2-azaadamantane-N-oxyl, and 9-azanoradamantane-N-oxyl, preferably 9-azanoradamantane-N-oxyl.

Examples of the co-catalyst to be used include potassium bromide and tetrabutylammonium bromide, preferably potassium bromide.

Examples of the oxidizing agent to be used include sodium hypochlorite and iodobenzene diacetate, preferably sodium hypochlorite.

The reaction temperature differs depending on the oxidation catalyst and the co-catalyst to be used but is generally 0° C. to 50° C., preferably 0 to 10° C.

The reaction time differs depending on the types and amounts of the oxidation catalyst and the co-catalyst to be used but is generally 10 minutes to 24 hours, preferably 1 hour to 3 hours.

After completion of the reaction, a toluene solution of the target compound (9) of this reaction is obtained, for example, by allowing the reaction solution to stand, then removing the aqueous layer, thereby separating an organic layer containing the target compound, and washing it with water. The resultant can be used for the following step, as it is.

The compound obtained can be further purified by conventional methods such as recrystallization and silica gel chromatography, if necessary.

(Step C-6)

This step is a step of stereoselectively hydroxymethylating the carbon at the 4-position of the compound (9) produced in step C-5 in a solvent in the presence of a base and an alkylating agent with epimerization, to produce a compound (10).

Examples of the solvent to be used include amides such as dimethylacetamide and dimethylformamide, hydrocarbons such as benzene and toluene, hydrocarbon halides such as methylene chloride, chloroform, and 1,2-dichloroethane, ethers such as tetrahydrofuran and dimethyl ether, and esters such as methyl acetate, ethyl acetate, and propyl acetate, preferably toluene.

Examples of the base to be used include inorganic bases such as sodium hydroxide, potassium hydroxide, sodium bicarbonate, and sodium carbonate, and organic bases such as triethylamine, pyridine, and 1,8-diazabicyclo[5.4.0]undec-7-ene, preferably 1,8-diazabicyclo[5.4.0]undec-7-ene.

Examples of the alkylating agent to be used include an aqueous paraformaldehyde or formaldehyde solution, preferably an aqueous formaldehyde solution.

The reaction temperature differs depending on the base to be used but is generally 0° C. to 50° C., preferably 20 to 30° C.

The reaction time differs depending on the type and the amount of the base to be used but is generally 10 minutes to 24 hours, preferably 1 hour to 3 hours.

After completion of the reaction, a toluene solution of the target compound (10) of this reaction is obtained, for example, by allowing the reaction solution to stand, then removing the aqueous layer, thereby separating an organic layer containing the target compound, and washing it with water. The resultant can be used for the following step, as it is. Further, a cyclized product

(11) partially generated at this time is converted into a compound (12) in the following step.

The compound obtained can be further purified by conventional methods such as recrystallization and silica gel chromatography, if necessary.

(Step C-7)

This step is a step of reacting a hydride reducing agent with the compound (10) produced in step C-6 in a solvent, to produce the compound (12) in which the hydroxyl group at the 3-position is sterically controlled.

Examples of the solvent to be used include hydrocarbon halides such as methylene chloride, chloroform, and 1,2-dichloroethane, hydrocarbons such as benzene and toluene, and ethers such as tetrahydrofuran and dimethyl ether, preferably toluene.

Examples of the hydride reducing agent to be used include sodium bis(2-methoxyethoxy)aluminum hydride, lithium aluminum hydride, diisobutylaluminum hydride, and sodium borohydride, preferably sodium borohydride.

The reaction temperature differs depending on the hydride reducing agent to be used but is generally 0° C. to 50° C., preferably 20 to 30° C.

The reaction time differs depending on the type and the amount of the hydride reducing agent to be used but is generally 10 minutes to 24 hours, preferably 1 hour to 3 hours.

After completion of the reaction, a toluene solution of the target compound (12) of this reaction is obtained, for example, by allowing the reaction solution to stand, then removing the aqueous layer, thereby separating an organic layer containing the target compound, and washing it with water. The resultant can be used for the following step, as it is.

The compound obtained can be further purified by conventional methods such as recrystallization and silica gel chromatography, if necessary.

(Step C-8)

This step is a step of reacting a protection reagent for a hydroxyl group in a solvent in the presence of a base and a catalyst and protecting two hydroxyl groups of the compound (12) produced in step C-7, to produce a compound (13).

Examples of the solvent to be used include hydrocarbon halides such as methylene chloride, chloroform, and 1,2-dichloroethane, hydrocarbons such as benzene and toluene, and ethers such as tetrahydrofuran and dimethyl ether, preferably toluene.

Examples of the protection reagent for a hydroxyl group to be used include trityl chloride, t-butyldiphenylsilyl chloride, t-butyldimethylsilyl chloride, acetic anhydride, and benzoyl chloride, preferably benzyl chloride or benzyl bromide, more preferably benzyl bromide.

Examples of the catalyst to be used include tetrabutylammonium iodide, potassium iodide, and sodium iodide, preferably tetrabutylammonium iodide.

Examples of the base to be used include inorganic bases such as sodium hydroxide, potassium hydroxide, sodium bicarbonate, and sodium carbonate, and organic bases such as triethylamine, pyridine, and 1,8-diazabicyclo[5.4.0]undec-7-ene, preferably potassium hydroxide.

The reaction temperature differs depending on the protection reagent for a hydroxyl group to be used but is generally 20° C. to 100° C., preferably 60 to 80° C.

The reaction time differs depending on the type and the amount of the protection reagent for a hydroxyl group to be used but is generally 1 hour to 48 hours, preferably 10 hours to 24 hours.

After completion of the reaction, a toluene solution of the target compound (13) of this reaction is obtained, for example, by allowing the reaction solution to stand, then removing the aqueous layer, thereby separating an organic layer containing the target compound, and washing it with water, and can be crystallized by solvent-substituting the toluene layer obtained with 1-propanol.

The compound obtained can be further purified by conventional methods such as recrystallization and silica gel chromatography, if necessary.

The compound (13A) (in the case of n=2 to 4) can be produced by method D described below.

(Method D)

[Formula 71]

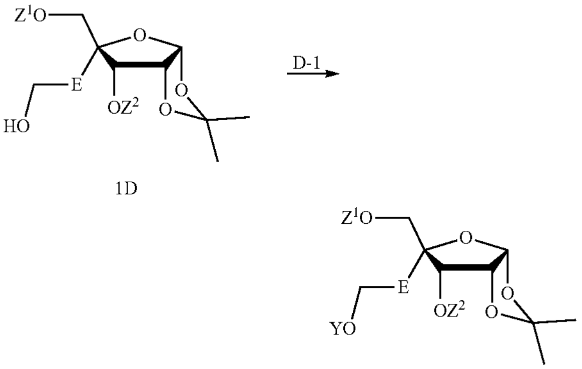

1D

13A'

In method D, E represents ethylene, trimethylene, or tetramethylene, and Y, $Z^1$, and $Z^2$ have the same meanings as above.

Hereinafter, each step of method D will be described in detail.

(Step D-1)

This step is a step of reacting a protection reagent for a hydroxyl group with a compound (1D) produced according to the method for producing a compound (3b) of International Publication No. WO 00/47599 in a solvent in the presence of a base, to produce a compound (13A').

Examples of the solvent to be used include amides such as dimethylacetamide and dimethylformamide, hydrocarbons such as benzene and toluene, hydrocarbon halides such as methylene chloride, chloroform, and 1,2-dichloroethane, ethers such as tetrahydrofuran and dimethyl ether, and esters such as methyl acetate, ethyl acetate, and propyl acetate, preferably toluene.

Examples of the base to be used include bases such as triethylamine, pyridine, dimethylaminopyridine 1-methylimidazole, and 4-methylmorpholine, preferably 4-methylmorpholine.

Examples of the protection reagent for a hydroxyl group to be used include trityl chloride and 4,4'-dimethoxytrityl chloride, preferably trityl chloride.

The reaction temperature differs depending on the protection reagent to be used but is generally 0° C. to 50° C., preferably 20 to 30° C.

The reaction time differs depending on the type and the amount of the protection reagent to be used but is generally 10 minutes to 24 hours, preferably 1 hour to 5 hours.

After completion of the reaction, the target compound (13A') of this reaction is obtained, for example, by adding water to the reaction solution, separating an organic layer containing the target compound, washing it with water, and then distilling off the solvent.

The compound obtained can be further purified by conventional methods such as recrystallization and silica gel chromatography, if necessary.

The compound (5E) of the present invention can be produced by method E described below.

(Method E)

[Formula 72]

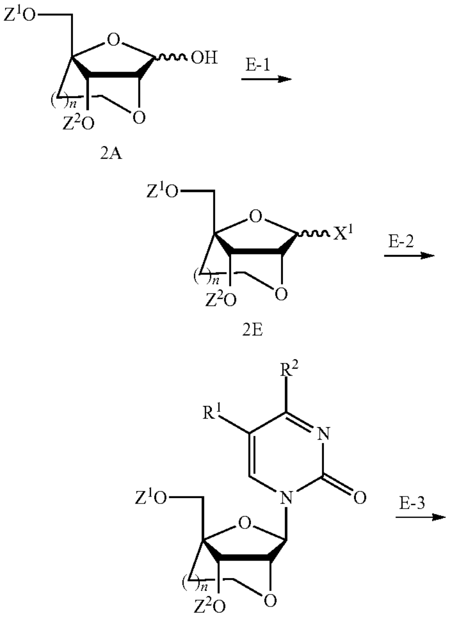

2A

2E

3E

-continued

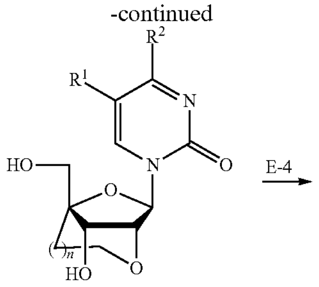

4E

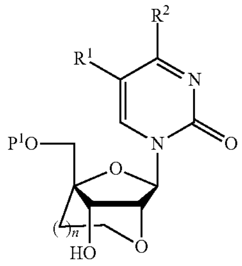

5E

In method E, $R^1$, $R^2$, $X^1$, $Z^1$, $Z^2$, and $P^1$ have the same meanings as above.

Hereinafter, each step of method E will be described in detail.

(Step E-1)

This step is a step of reacting an activator with the compound (2A) in a solvent in the presence of a base, to produce a compound (2E).

Examples of the solvent to be used include hydrocarbon halides such as methylene chloride, chloroform, and 1,2-dichloroethane, hydrocarbons such as benzene and toluene, ethers such as tetrahydrofuran and dimethyl ether, and acetonitrile, preferably toluene or acetonitrile.

Examples of the activator to be used include acetic anhydride, benzoic anhydride, trichloroacetonitrile, carbonyldiimidazole, and diphenyl chlorophosphate, preferably acetic anhydride or trichloroacetonitrile.

The base to be used differs depending on the activator, and examples thereof include organic bases such as triethylamine, pyridine, and 1,8-diazabicyclo[5.4.0]undec-7-ene, preferably pyridine or 1,8-diazabicyclo[5.4.0]undec-7-ene. After completion of the reaction, the target compound (2E) of this reaction, for example, can be directly used for glycosylation or obtained by neutralizing the reaction solution, concentrating the reaction mixture, and distilling off the solvent.

The reaction temperature differs depending on the activator to be used but is generally 0° C. to 50° C., preferably 0° C. to 30° C.

The reaction time differs depending on the type and the amount of the activator to be used but is generally 10 minutes to 24 hours, preferably 1 hour to 3 hours.

The compound obtained can be further purified by conventional methods such as recrystallization and silica gel chromatography, if necessary.

(Step E-2)

This step is a step of glycosylating the compound (2E) obtained in step E-1 with a pyrimidine base (such as cytosine protected by a thymine or acyl group) silylated by a silylation reaction in a solvent in the presence of a halogenating agent, to produce a compound (3E).

Examples of the solvent to be used for the silylation reaction and glycosylation reaction include hydrocarbon halides such as methylene chloride, chloroform, and 1,2-dichloroethane, hydrocarbons such as benzene and toluene, ethers such as tetrahydrofuran and dimethyl ether, and acetonitrile, preferably acetonitrile.

Examples of the silylating agent to be used include N,O-bistrimethylsilylacetamide and hexamethyldisilazane, preferably N,O-bistrimethylsilylacetamide.

The temperature for the silylating reaction of the pyrimidine base differs depending on the silylating agent but is generally 0° C. to 50° C., preferably 20° C. to 40° C.

The reaction time for the silylation reaction differs depending on the type and the amount of the silylating agent to be used but is generally 10 minutes to 24 hours, preferably 1 hour to 10 hours.

Examples of the halogenating agent to be used for the glycosylation reaction include chlorotrimethylsilane (TMSCl), bromotrimethylsilane (TMSBr), and iodotrimethylsilane (TMSI), preferably TMSI.

The reaction temperature for the glycosylation reaction differs depending on the structure of the compound (2E) and the halogenating agent to be used but is generally 0° C. to 50° C., preferably 20° C. to 40° C.

The reaction time for the glycosylation reaction differs depending on the type and the amount of the halogenating agent to be used but is generally 10 minutes to 24 hours, preferably 10 hours to 20 hours.

After completion of the reaction, the target compound (3E) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

(Step E-3)

This step is a step of reacting the compound (3E) with a deprotection reagent for a hydroxyl group in a solvent, to produce a compound (4E) by deprotection reaction.

(i) In the case where $R^2$ represents a hydroxyl group, and $Z^1$ and $Z^2$ each represent a benzyl group, the deprotection reagent is a metal catalyst supported on carbon and a reducing agent.

Examples of the solvent to be used include hydrocarbons such as benzene and toluene, ethers such as tetrahydrofuran and dimethyl ether, and alcohols such as methanol, ethanol, and propanol, preferably methanol.

Examples of the metal catalyst to be used include palladium, palladium hydroxide, and platinum, preferably palladium.

Examples of the reducing agent to be used include hydrogen, formic acid, and ammonium formate, preferably hydrogen.

The reaction temperature differs depending on the metal catalyst but is generally 0° C. to 70° C., preferably 40° C. to 60° C.

The reaction time differs depending on the types and the amounts of the metal catalyst and the reducing agent to be used but is generally 10 minutes to 24 hours, preferably 1 hour to 5 hours.

After completion of the reaction, the target compound (4E) of this reaction is obtained, for example, by filtering the reaction solution to remove the metal catalyst, concentrating the reaction mixture, and distilling off the solvent.

The compound obtained can be further purified by conventional methods such as recrystallization and silica gel chromatography, if necessary.

(ii) In the case where $R^2$ represents an amino group protected by an acyl group, and $Z^1$ and $Z^2$ each represent a benzyl group, deprotection reaction is carried out using a deprotection reagent.

Examples of the solvent to be used include hydrocarbon halides such as methylene chloride, chloroform, and 1,2-dichloroethane, and hydrocarbons such as benzene and toluene, preferably methylene chloride.

Examples of the deprotection reagent to be used include iron (III) chloride and boron trichloride, preferably boron trichloride.

The reaction temperature differs depending on the deprotection reagent but is generally −20° C. to 30° C., preferably −20° C. to 20° C.

The reaction time differs depending on the deprotection reagent but is generally 10 minutes to 10 hours, preferably 1 hour to 5 hours.

After completion of the reaction, the target compound (4E) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

(Step E-4)

This step is a step of reacting a protection reagent for a primary hydroxyl group with the compound (4E) in a solvent in the presence of a base, to produce a compound (5E).

Examples of the solvent to be used include hydrocarbon halides such as methylene chloride, chloroform, and 1,2-dichloroethane, hydrocarbons such as benzene and toluene, ethers such as tetrahydrofuran and dimethyl ether, esters such as ethyl acetate and propyl acetate, acetonitrile, preferably tetrahydrofuran or ethyl acetate.

Examples of the protection reagent for a primary hydroxyl group to be used include trityl chloride, 4-methoxytrityl chloride, and 4,4'-dimethoxytrityl chloride, preferably 4,4'-dimethoxytrityl chloride.

Examples of the base to be used include aliphatic amines such as triethylamine and N-methylmorpholine, and aromatic amines such as imidazole and pyridine, preferably pyridine.

The reaction temperature differs depending on the protection reagent but is generally 0° C. to 50° C., preferably 0° C. to 20° C.

The reaction time differs depending on the protection reagent but is generally 10 minutes to 10 hours, preferably 1 hour to 5 hours.

After completion of the reaction, the target compound (5E) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

The compound (4F) of the present invention can be produced by method F described below.

(Method F)

[Formula 73]

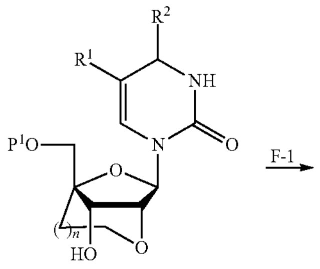

5E'

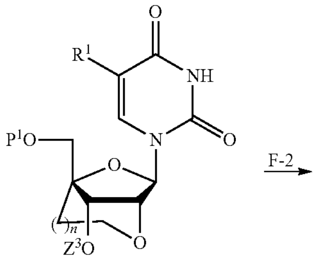

1F

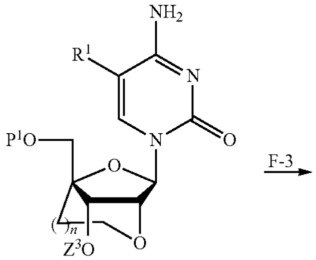

2F

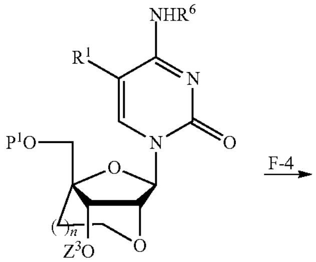

3F

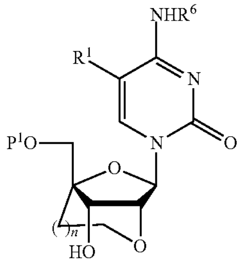

4F

In method F, $R^1$, $R^6$, $Z^3$, and $P^1$ have the same meanings as above.

Hereinafter, each step of method F will be described in detail.

(Step F-1)

This step is a step of reacting a compound (5E') with a protection reagent for a hydroxyl group in a solvent in the presence of a base and a catalyst, to produce a compound (1F).

Examples of the solvent to be used include hydrocarbon halides such as methylene chloride, chloroform, and 1,2-dichloroethane, hydrocarbons such as benzene and toluene, ethers such as tetrahydrofuran and dimethyl ether, and acetonitrile, preferably acetonitrile.

Examples of the protection reagent for a hydroxyl group to be used include acetic anhydride, acetyl chloride, benzoic anhydride, and benzoyl chloride, preferably acetic anhydride.

The base to be used differs depending on the protection reagent for a hydroxyl group, and examples thereof include organic bases such as triethylamine and pyridine, preferably triethylamine.

Examples of the catalyst to be used include N,N-dimethylaminopyridine and 1,8-diazabicyclo[5.4.0]undec-7-ene, preferably N,N-dimethylaminopyridine. The reaction temperature differs depending on the base to be used but is generally 0° C. to 50° C., preferably 0° C. to 30° C.

The reaction time differs depending on the type and the amount of the protection reagent to be used but is generally 10 minutes to 24 hours, preferably 1 hour to 3 hours.

After completion of the reaction, the target compound (1F) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

(Step F-2)

This step is a step of activating a hydroxyl group of the compound (1F) using an activator and then reacting it with an aminating agent in a solvent in the presence of a base and a catalyst, to produce a compound (2F).

Examples of the solvent to be used include hydrocarbon halides such as methylene chloride, chloroform, and 1,2-dichloroethane, hydrocarbons such as benzene and toluene, ethers such as tetrahydrofuran and dimethyl ether, and acetonitrile, preferably acetonitrile.

The base to be used differs depending on the activator, and examples thereof include organic bases such as triethylamine and pyridine, preferably triethylamine.

Examples of the catalyst to be used include N,N-dimethylaminopyridine and 1,8-diazabicyclo[5.4.0]undec-7-ene, preferably N,N-dimethylaminopyridine.

Examples of the activator to be used include p-toluenesulfonyl chloride and 2,4,6-triisopropylbenzenesulfonyl chloride, preferably 2,4,6-triisopropylbenzenesulfonyl chloride.

The reaction temperature differs depending on the activator to be used but is generally 0° C. to 50° C., preferably 0° C. to 30° C.

The reaction time differs depending on the type and the amount of the activator to be used but is generally 10 minutes to 8 hours, preferably 1 hour to 3 hours.

Examples of the aminating agent to be used include ammonia, an aqueous ammonia solution, or ammonia salts such as ammonium carbonate and ammonium acetate, preferably an aqueous ammonia solution.

The reaction temperature differs depending on the aminating agent to be used but is generally 0° C. to 50° C., preferably 0° C. to 30° C.

The reaction time differs depending on the type and the amount of the aminating agent to be used but is generally 10 minutes to 8 hours, preferably 1 hour to 3 hours.

After completion of the reaction, the target compound (2F) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

(Step F-3)

This step is a step of acylating the amino group of the compound (2F) with an acylating agent in a solvent in the presence of a base, to produce a compound (3F).

Examples of the solvent to be used include hydrocarbon halides such as methylene chloride, chloroform, and 1,2-dichloroethane, hydrocarbons such as benzene and toluene, ethers such as tetrahydrofuran and dimethyl ether, and acetonitrile, preferably acetonitrile.

Examples of the base to be used include inorganic bases such as sodium hydroxide, potassium hydroxide, sodium bicarbonate, and sodium carbonate, and organic bases such as triethylamine, pyridine, and 1,8-diazabicyclo[5.4.0]undec-7-ene, preferably sodium hydroxide.

Examples of the acylating agent to be used include benzoyl chloride and benzoic anhydride, preferably benzoic anhydride.

The reaction temperature differs depending on the acylating agent to be used but is generally 0° C. to 50° C., preferably 10° C. to 40° C.

The reaction time differs depending on the type and the amount of the acylating agent to be used but is generally 1 to 48 hours, preferably 2 hours to 20 hours.

After completion of the reaction, the target compound (3F) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

(Step F-4)

This step is a step of selectively hydrolyzing the acyl group at the 3-position of the compound (3F) with a base in a solvent, to produce a compound (4F).

Examples of the solvent to be used include alcohols such as methanol, ethanol, and propanol, water, and acetonitrile, preferably water or acetonitrile.

Examples of the base to be used include inorganic bases such as sodium hydroxide, potassium hydroxide, sodium bicarbonate, and sodium carbonate, preferably sodium hydroxide.

The reaction temperature differs depending on the base to be used but is generally 0° C. to 50° C., preferably 0° C. to 30° C.

The reaction time differs depending on the base to be used but is generally 10 minutes to 24 hours, preferably 1 hour to 3 hours.

After completion of the reaction, the target compound (4F) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

The compound (3G) of the present invention can be produced by method G described below.

(Method G)

[Formula 74]

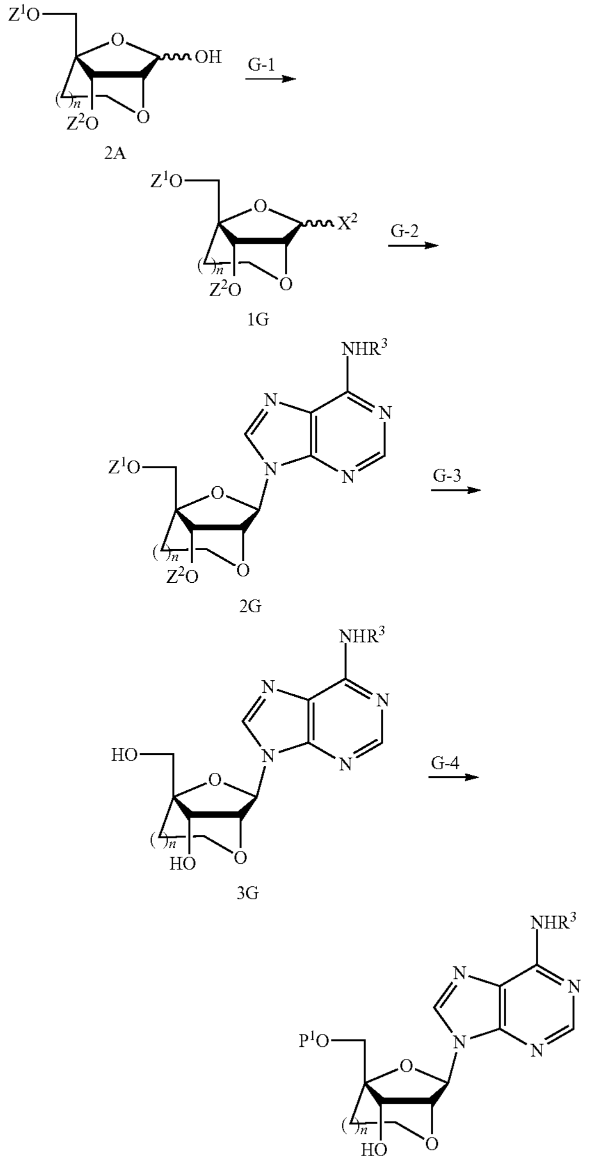

2A, 1G, 2G, 3G, 4G

In method G, $R^3$, $X^2$, $Z^1$, $Z^2$, and $P^1$ have the same meanings as above.

Hereinafter, each step of method G will be described in detail.

(Step G-1)

This step is a step of reacting an activator with the compound (2A) in a solvent in the presence of a base, to produce a compound (1G).

Examples of the solvent to be used include hydrocarbon halides such as methylene chloride, chloroform, and 1,2-dichloroethane, hydrocarbons such as benzene and toluene, ethers such as tetrahydrofuran and dimethyl ether, and acetonitrile, preferably toluene or acetonitrile.

The reaction temperature differs depending on the activator to be used but is generally 0° C. to 50° C., preferably 0° C. to 30° C.

Examples of the activator to be used include acetic anhydride, benzoic anhydride, trichloroacetonitrile, carbonyldiimidazole, and diphenyl chlorophosphate, preferably acetic anhydride or benzoic anhydride.

The base to be used differs depending on the activator, and examples thereof include organic bases such as triethylamine, pyridine, N,N-dimethylaminopyridine, and 1,8-diazabicyclo[5.4.0]undec-7-ene, preferably N,N-dimethylaminopyridine.

The reaction temperature differs depending on the activator to be used but is generally 0° C. to 50° C., preferably 0° C. to 30° C.

The reaction time differs depending on the type and the amount of the activator to be used but is generally 10 minutes to 8 hours, preferably 1 hour to 3 hours.

After completion of the reaction, the target compound (1G) of this reaction, for example, can be directly used for glycosylation or obtained by neutralizing the reaction solution, concentrating the reaction mixture, and distilling off the solvent.

The compound obtained can be further purified by conventional methods such as recrystallization and silica gel chromatography, if necessary.

(Step G-2)

This step is a step of glycosylating the compound (1G) with an amino group-protected 6-aminopurin-9-yl group in a solvent in the presence of an acid reagent, to produce a compound (2G) by subsequent isomerization.

Examples of the solvent to be used include hydrocarbon halides such as methylene chloride, chloroform, and 1,2-dichloroethane, hydrocarbons such as benzene and toluene, ethers such as tetrahydrofuran, and acetonitrile, preferably acetonitrile.

Examples of the acid reagent to be used include dichlorodimethylsilane with trifluoromethanesulfonic acid, and trimethylsilyl trifluoromethanesulfonate with trifluoromethanesulfonic acid, methanesulfonic acid, or trifluoroacetic acid, preferably trimethylsilyl trifluoromethanesulfonate with trifluoroacetic acid.

The reaction temperature for glycosylation and isomerization differs depending on the structure of the compound (1G) and the acid reagent to be used but is generally 30° C. to 70° C., preferably 40° C. to 60° C.

The reaction time differs depending on the type and the amount of the Lewis acid reagent to be used but is generally 10 minutes to 24 hours, preferably 1 hour to 5 hours.

After completion of the reaction, the target compound (2G) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

(Step G-3)

This step is a step of reacting the compound (2G) with a deprotection reagent in a solvent and deprotecting $Z^1$ and $Z^2$, to produce a compound (3G)

Examples of the solvent to be used include hydrocarbon halides such as methylene chloride, chloroform, and 1,2-dichloroethane, and hydrocarbons such as benzene and toluene, preferably methylene chloride.

In the case where $Z^1$ and $Z^2$ each represent a benzyl group, examples of the deprotection reagent include iron (III) chloride and boron trichloride, preferably boron trichloride.

The reaction temperature differs depending on the deprotection reagent but is generally −20° C. to 30° C., preferably −20° C. to 20° C.

The reaction time differs depending on the deprotection reagent but is generally 10 minutes to 10 hours, preferably 1 hour to 5 hours.

After completion of the reaction, the target compound (3G) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

(Step G-4)

The target compound (4G) of this step can be produced by protecting the primary hydroxyl group of the compound (3G) according to step E-4 of method E.

Further, the compound (5H) of the present invention can be produced by method H (glycosylation using dichloropurine) described below.

(Method H)

[Formula 75]

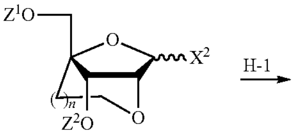

1G

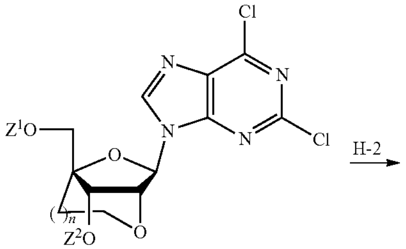

1H

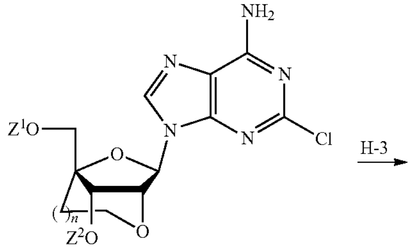

2H

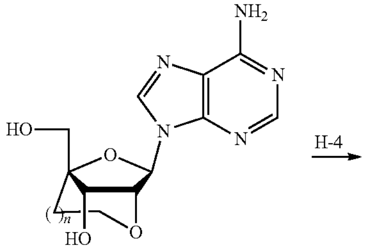

3H

-continued

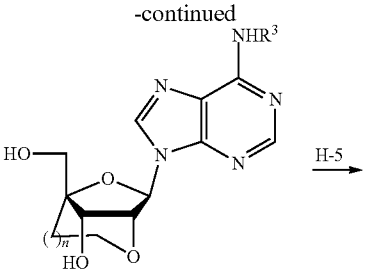

4H

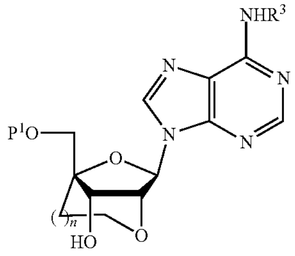

5H

In method H, $R^3$, $Z^1$, $Z^2$, and $P^1$ have the same meanings as above.

Hereinafter, each step of method H will be described in detail.

(Step H-1)

This step is a step of glycosylating the compound (1G) with dichloropurine silylated by a silylation reaction in a solvent in the presence of a halogenating agent, to produce a compound (1H).

Examples of the solvent to be used for the glycosylation reaction and silylation reaction include hydrocarbon halides such as methylene chloride, chloroform, and 1,2-dichloroethane, hydrocarbons such as benzene and toluene, ethers such as tetrahydrofuran, and acetonitrile, preferably acetonitrile.

Examples of the silylating agent to be used for the silylation reaction include N,O-bistrimethylsilylacetamide and hexamethyldisilazane, preferably N,O-bistrimethylsilylacetamide.

The reaction temperature for the silylation reaction of dichloropurine differs depending on the silylating agent but is generally 0° C. to 90° C., preferably 50° C. to 80° C.

The reaction time for the silylation reaction differs depending on the type and the amount of the silylating agent to be used but is generally 10 minutes to 24 hours, preferably 1 hour to 10 hours.

Examples of the halogenating agent to be used for the glycosylation reaction include chlorotrimethylsilane (TMSCl), bromotrimethylsilane (TMSBr), and iodotrimethylsilane (TMSI), preferably TMSI. The reaction temperature for the glycosylation reaction differs depending on the structure of the compound (2B) and the halogenating agent to be used but is generally 0° C. to 90° C., preferably 50° C. to 80° C.

The reaction time for the glycosylation reaction differs depending on the type and the amount of the halogenating agent to be used but is generally 10 minutes to 24 hours, preferably 10 hours to 5 hours.

After completion of the reaction, the target compound (1H) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

(Step H-2)

This step is a step of reacting the compound (1H) with an aminating agent in a solvent, to produce a compound (2H).

Examples of the solvent to be used include hydrocarbon halides such as methylene chloride, chloroform, and 1,2-dichloroethane, hydrocarbons such as benzene and toluene, ethers such as tetrahydrofuran and dimethyl ether, and acetonitrile, preferably tetrahydrofuran.

Examples of the aminating agent to be used include ammonia, an aqueous ammonia solution, and ammonia salts such as ammonium carbonate and ammonium acetate, preferably an aqueous ammonia solution.

The reaction temperature is generally 0° C. to 90° C., preferably 30° C. to 60° C.

The reaction time differs depending on the amounts of the solvent and the aminating agent to be used but is generally 10 minutes to 24 hours, preferably 1 hour to 10 hours.

After completion of the reaction, the target compound (2H) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

(Step H-3)

This step is a step of deprotecting $Z^1$ and $Z^2$ of the compound (2H) and hydrogenating the chlorine atom at the 2-position of the purine ring in a solvent, to produce a compound (3H).

Examples of the solvent to be used include water, alcohols such as methanol, ethanol, 1-propanol, and 2 -propanol, hydrocarbons such as benzene and toluene, ethers such as tetrahydrofuran and diethyl ether, and acetonitrile, preferably ethanol.

In the case where $Z^1$ and $Z^2$ each represent a benzyl group, the deprotection reaction of $Z^1$ and $Z^2$ and the hydrogenation reaction at the 2-position of the purine ring can be performed at the same time using a reducing agent in the presence of a metal catalyst.

Examples of the metal catalyst to be used include palladium, palladium hydroxide, and platinum (particularly, palladium supported on carbon, palladium hydroxide, or platinum), preferably palladium (particularly, palladium supported on carbon).

Examples of the reducing agent to be used include hydrogen, formic acid, and ammonium formate, preferably hydrogen.

The reaction temperature differs depending on the metal catalyst but is generally 0° C. to 70° C., preferably 40° C. to 60° C.

The reaction time differs depending on the types and the amounts of the metal catalyst and the reducing agent to be used but is generally 10 minutes to 24 hours, preferably 1 hour to 10 hours.

After completion of the reaction, the target compound (3H) of this reaction is obtained, for example, by filtering the reaction solution to remove the metal catalyst, concentrating the reaction mixture, and distilling off the solvent.

The compound obtained can be further purified by conventional methods such as recrystallization and silica gel chromatography, if necessary.

(Step H-4)

This step is a step of protecting a hydroxyl group of the compound (3H) with a protection reagent for a hydroxyl group in a solvent, then acylating the amino group on the purine ring with an acylating agent, and then removing the protective group on the hydroxyl group with ammonia, to produce a compound (4H).

Examples of the solvent to be used include pyridine and acetonitrile, preferably pyridine.

Examples of the protection reagent for a hydroxyl group to be used include chlorotrimethylsilane and trifluoromethanesulfonyltrimethylsilane, preferably chlorotrimethylsilane.

The reaction temperature is generally 0° C. to 90° C., preferably 0° C. to 30° C.

The reaction time differs depending on the type and the amount of the protection reagent for a hydroxyl group to be used but is generally 10 minutes to 2 hours, preferably 30 minutes to 1 hour.

Examples of the acylating agent to be used include acetic anhydride, acetyl chloride, benzoic anhydride, and benzoyl chloride, preferably benzoyl chloride.

The acylation reaction temperature is generally 0° C. to 90° C., preferably 0° C. to 30° C.

The reaction time differs depending on the type and the amount of the protection reagent for a hydroxyl group to be used but is generally 1 hour to 8 hours, preferably 1 hour to 3 hours.

The target compound (4H) of this reaction is obtained, for example, by adding ammonia water to the reaction solution, then concentrating the reaction mixture, and distilling off the solvent.

The compound obtained can be further purified by conventional methods such as recrystallization and silica gel chromatography, if necessary.

(Step H-5)

The target compound (5H) of this step can be produced by protecting the primary hydroxyl group of the compound (4H) according to step E-4 of method E.

The compound (4I) of the present invention can be produced by method I described below.

(Method I)

[Formula 76]

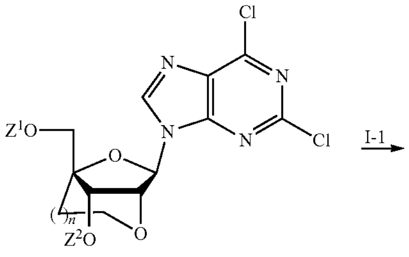

1H

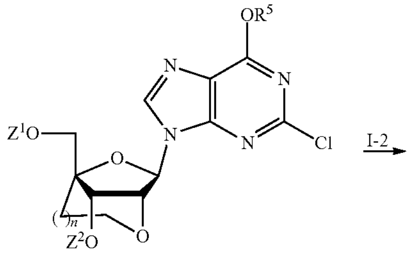

1I

-continued

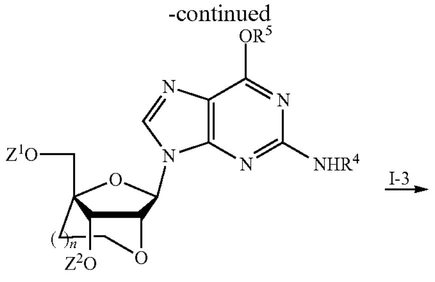

2I

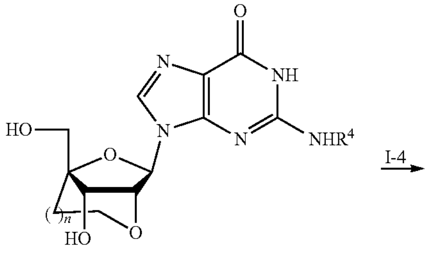

3I

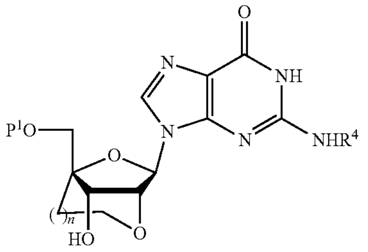

4I

In method I, $R^4$, $R^5$, $Z^1$, $Z^2$, and $P^1$ have the same meanings as above.

Hereinafter, each step of method I will be described in detail.

(Step I-1)

This step is a step of subjecting the compound (1H) to a substitution reaction with benzyl alcohol optionally having a substituent in a solvent in the presence of a base, to produce a compound (1I).

Examples of the benzyl alcohol optionally having a substituent include benzyl alcohol, 4-methylbenzyl alcohol, 2,4,6-trimethylbenzyl alcohol, 3,4,5-trimethylbenzyl alcohol, 4-methoxybenzyl alcohol, 4-chlorobenzyl alcohol, 4-bromobenzyl alcohol, and 4-cyanobenzyl alcohol, preferably benzyl alcohol.

Examples of the solvent to be used include hydrocarbon halides such as methylene chloride, chloroform, and 1,2-dichloroethane, hydrocarbons such as benzene and toluene, ethers such as tetrahydrofuran and dimethyl ether, and acetonitrile, preferably tetrahydrofuran.

Examples of the base to be used include inorganic bases such as sodium hydride and sodium carbonate, and organic bases such as triethylamine, pyridine, and 1,8-diazabicyclo[5.4.0]undec-7-ene, preferably sodium hydride.

The reaction temperature is generally 0° C. to 90° C., preferably 0° C. to 30° C.

The reaction time differs depending on the amounts of the solvent and the base to be used but is generally 10 minutes to 24 hours, preferably 1 hour to 10 hours.

After completion of the reaction, the target compound (1I) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

(Step I-2)

This step is a step of cross-coupling the compound (1I) with an amidating agent in a solvent in the presence of a base, a palladium catalyst, and a phosphine ligand, to produce a compound (2I).

Examples of the solvent to be used include hydrocarbon halides such as methylene chloride, chloroform, and 1,2-dichloroethane, hydrocarbons such as benzene and toluene, ethers such as tetrahydrofuran and dimethyl ether, and acetonitrile, preferably toluene.

Examples of the base to be used include inorganic bases such as sodium hydroxide, sodium carbonate, and cesium carbonate, and organic bases such as triethylamine, pyridine, and 1,8-diazabicyclo[5.4.0]undec-7-ene, preferably cesium carbonate.

Examples of the palladium catalyst to be used include tris(dibenzylideneacetone) (chloroform)dipalladium, palladium (II) acetate, and tris(dibenzylideneacetone)dipalladium (0), preferably tris(dibenzylideneacetone) (chloroform)dipalladium.

Examples of the phosphine ligand to be used include 4,5'-bis(diphenylphosphino)-9,9'-dimethylxanthene, 1,1'-bis (diphenylphosphino)ferrocene, 1,2-bis(diphenylphosphino) ethane, and 2-dicyclohexylphosphino-2'-(N,N-dimethylamino)biphenyl, preferably 4,5'-bis(diphenylphosphino)-9, 9'-dimethylxanthene.

Examples of the amidating agent to be used include acetyl amide, benzoyl amide, and isobutyl amide, preferably isobutyl amide.

The reaction temperature is generally 20° C. to 150° C., preferably 90° C. to 110° C.

The reaction time differs depending on the amounts of the solvent and the palladium catalyst to be used but is generally 10 minutes to 24 hours, preferably 5 hours to 15 hours.

After completion of the reaction, the target compound (21) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

(Step 1-3)

This step is a step of reacting the compound (21) with a deprotection reagent for a hydroxyl group in a solvent and deprotecting $Z^1$, $Z^2$, and $R^5$, to produce a compound (31).

In the case where $Z^1$ and $Z^2$ each represent a benzyl group, the deprotection reagent is a metal catalyst supported on carbon and a reducing agent.

Examples of the metal catalyst to be used include palladium, palladium hydroxide, and platinum, preferably palladium hydroxide.

Examples of the reducing agent to be used include hydrogen, formic acid, and ammonium formate, preferably hydrogen.

The reaction temperature differs depending on the metal catalyst but is generally 0° C. to 70° C., preferably 40° C. to 60° C.

The reaction time differs depending on the types and the amounts of the metal catalyst and the reducing agent to be used but is generally 10 minutes to 24 hours, preferably 1 hour to 10 hours.

After completion of the reaction, the target compound (31) of this reaction is obtained, for example, by filtering the reaction solution to remove the metal catalyst, concentrating the reaction mixture, and distilling off the solvent.

The compound obtained can be further purified by conventional methods such as recrystallization and silica gel chromatography, if necessary.

(Step 1-4)

The target compound (41) of this step can be produced by protecting the primary hydroxyl group of the compound (31) according to step E-4 of method E.

The compound (2J) can be produced by method J described below.

(Method J)

[Formula 77]

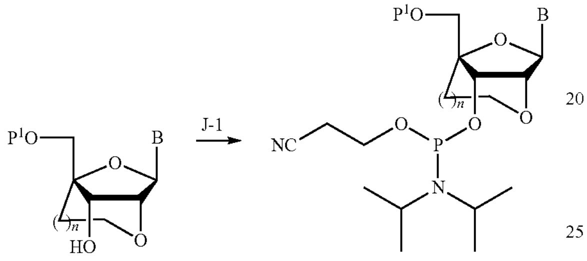

1J 2J

In method J, $P^1$ and B have the same meanings as above.

Hereinafter, each step of method J will be described in detail.

(Step J-1)

This step is a step of reacting the compound (1J) with an amidite-forming reagent in a solvent in the presence of a drying agent and an activator, to produce a compound (2J) by an amidite-forming reaction.

Examples of the solvent to be used include hydrocarbon halides such as methylene chloride, chloroform, and 1,2-dichloroethane, esters such as ethyl acetate, propyl acetate, and butyl acetate, hydrocarbons such as benzene and toluene, ethers such as tetrahydrofuran, and acetonitrile, preferably methylene chloride.

Examples of the drying agent to be used include molecular sieve 3A, molecular sieve 4A, and molecular sieve 5A, preferably molecular sieve 4A.

Examples of the activator to be used include 5-benzylthiotetrazole, 5-phenyltetrazole, dibromoimidazole, dicyanoimidazole, and N-alkylimidazole trifluoroacetate, preferably 4,5-dicyanoimidazole.

Examples of the amidite-forming reagent to be used include 2-cyanoethyl N,N,N',N'-tetraisopropyl phosphorodiamidite and 2-cyanoethyldiisopropyl chlorophosphoramidite, preferably 2-cyanoethyl N,N,N',N'-tetraisopropyl phosphorodiamidite.

The reaction temperature differs depending on the amidite-forming reagent to be used but is generally 0° C. to 50° C., preferably 0° C. to 30° C.

The reaction time differs depending on the amidite-forming reagent to be used but is generally 10 minutes to 24 hours, preferably 1 hour to 16 hours.

After completion of the reaction, the target compound (2J) of this reaction is obtained, for example, by neutralizing the reaction solution, concentrating the reaction mixture, and distilling off the solvent.

The compound obtained can be further purified by conventional methods such as recrystallization and silica gel chromatography, if necessary.

According to one aspect, the present invention provides a method for producing an oligonucleotide having a desired sequence/structure by linking a phosphoramidite compound of a nucleoside corresponding to each ENA monomer produced by the aforementioned method and a commercially available nucleic acid or a modified nucleic acid to a phosphoramidite compound of a ligand unit via a phosphodiester bond or a phosphorothioate bond, to extend the unit chain. Such an oligonucleotide can be produced by synthesis using a commercially available synthesizer (e.g., model 392 by the phosphoramidide method, available from PerkinElmer, Inc.) or the like according to the method described in the literature (Nucleic Acids Research, 12, 4539 (1984)). As the phosphoramidite compound of the nucleoside of each ENA used at that time (that is, 2'-0,4'-C-ethylene-bridged guanosine, 2'-0,4'-C-ethylene-bridged adenosine, 2'-0,4'-C-ethylene-bridged cytidine, or 2'-O,4'-C-ethylene-bridged thymidine), a compound produced by the aforementioned method can be used. Phosphoramidite compounds of a natural nucleoside and 2'-O-methyl nucleoside (that is, 2'-O-methylguanosine, 2'-O-methyladenosine, 2'-O-methylcytidine, or 2'-O-methyluridine) can be produced using commercially available reagents.

In the nucleotide sequences of the present invention, adenine can be described as (A) or (a), guanine can be described as (G) or (g), cytosine can be described as (C) or (c), thymine can be described as (T) or (t), and uracil can be described as (U) or (u). Instead of cytosine, 5-methylcytosine can be used. Of the nucleobases, uracil (U) or (u) and thymine (T) or (t) are compatible. Both uracil (U) or (u) and thymine (T) or (t) can be used for base pairing with complementary strand adenine (A) or (a).

After coupling the phosphoramidite compounds, an oligonucleotide having a phosphorothioate bond can be synthesized by reacting a reagent such as sulfur, tetraethylthiuram disulfide (TETD, Applied Biosystems), Beaucage reagent (Glen Research), or xanthane hydride (Tetrahedron Letters, 32, 3005 (1991), J. Am. Chem. Soc. 112, 1253 (1990), PCT/WO98/54198).

As the controlled pore glass (CPG) to be used in the synthesizer, commercially available products can be used for those bound to 2'-O-methyl nucleoside. 2'-0,4'-C-methylene guanosine, adenosine, 5-methylcytidine, and thymidine can be bound to CPG according to the method described in International Publication No. WO 99/14226, and 2'-O, 4'-C-ethylene guanosine, adenosine, 5-methylcytidine, and thymidine produced by the aforementioned method can be bound to CPG according to the literature (Oligonucleotide Synthesis, Edited by M. J. Gait, Oxford UniversityPress, 1984). An oligonucleotide in which a 2-hydroxyethyl phosphate group is bound to the 3' end can be synthesized using a modified CPG (described in Example 12b of Japanese Patent Laid-Open No. 7-87982). Further, an oligonucleotide in which a hydroxyalkyl phosphate group or an aminoalkyl phosphate group is bound to the 3' end can be synthesized using 3'-amino-ModifierC3 CPG, 3'-amino-Modifier C7

CPG, Glyceryl CPG (Glen Research), 3'-specer C3SynBase CPG 1000, or 3'-specer C9 SynBase CPG 1000 (linktechnologies).

An oligonucleotide to be produced by the present invention may contain a ligand unit suitable for transporting nucleic acids to tissues. The ligand unit can be bound to the 5' end of the oligonucleotide by synthesizing an amidite compound in which the ligand moiety contains a phosphate moiety via a linker, according to the same method as for extension of the nucleotide. An oligonucleotide in which GalNAc is bound to the phosphate moiety via a linker is used for transportation to the liver, and a phosphoramidite compound corresponding to $X^{18}$ or $X^{20}$ below or the like is used for producing the oligonucleotide. As the phosphoramidite compound corresponding to $X^{18}$, which is the GalNAc unit, the compound 39D of Reference Example 39 of International Publication No. WO 2019/172286 ([(2R, 3R, 4R, 5R, 6R)-5-acetoamido-6-[3-[[2-[[3-[[2-[3-[(2R, 3R, 4R, 5R, 6R)-3-acetoamido-4,5-diacetoxy-6-[[bis(4-methoxyphenyl)-phenyl-methoxy]methyl]tetrahydropyran-2-yl]oxypropylamino]-2-oxo-ethyl]carbamoyloxy]-2-[2-cyanoethoxy-(diisopropylamino)phosphanyl]oxy-propoxy]carbonylamino]acetyl]amino]propoxy]-4-acetoxy-2-[[bis(4-methoxyphenyl)-phenyl-methoxy]methyl]tetrahydropyran-3-yl]acetate):

[Formula 78]

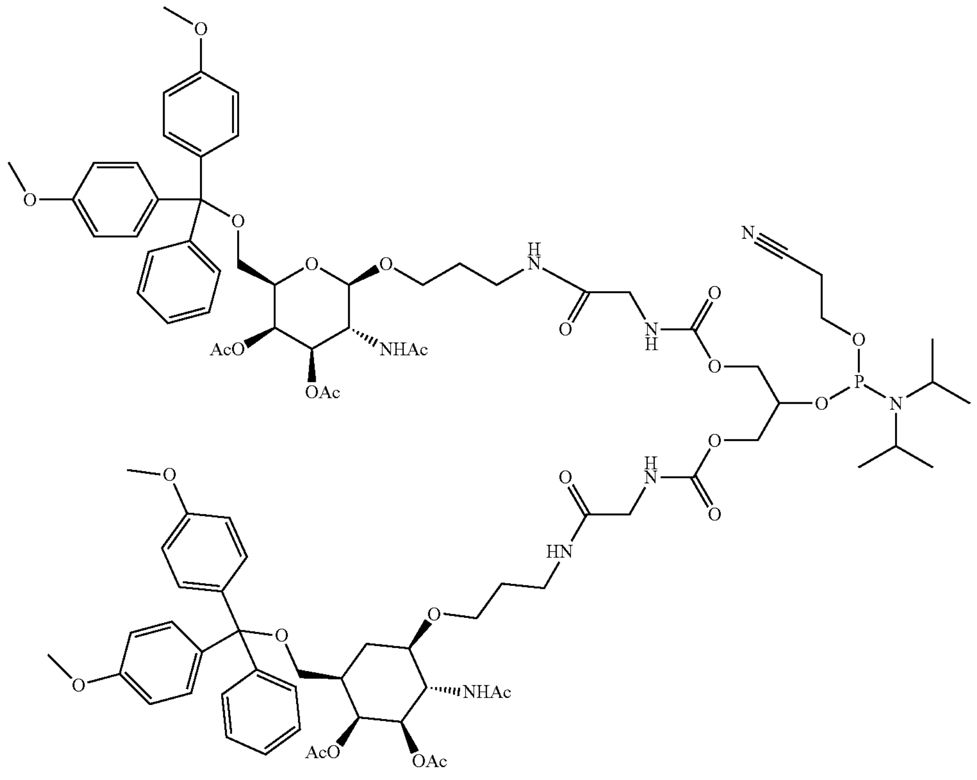

can be used, and as the phosphoramidite compound corresponding to $X^{20}$, the compound 41D of Reference Example 41 of International Publication No. WO 2019/172286 ([(2R,3R, 4R,5R,6R)-5-acetoamido-6-[3-[3-[[3-[[3-[3-[(2R, 3R, 4R, 5R, 6R)-3-acetoamido-4,5-diacetoxy-6-[[bis(4-methoxyphenyl)-phenyl-methoxy]methyl]tetrahydropyran-2-yl]oxypropylamino]-3-oxo-propyl]carbamoyloxy]-2-[2-cyanoethoxy-(diisopropylamino) phosphanyl 1]oxy-propoxy]carbonylamino] propanoylamino]propoxy]-4-acetoxy-2-[[bis(4-methoxyphenyl)-phenyl-methoxy]methyl] tetrahydropyran-3-yl]acetate):

[Formula 79]

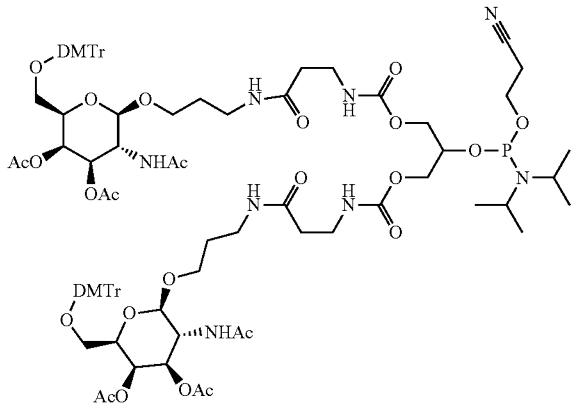

can be used, respectively.

As one aspect of the oligonucleotide to be produced by the method of the present invention, oligonucleotides, having the sequences and the structures represented by the following formulas, useful for treatment of Duchenne-type muscular dystrophy (see International Publication No. WO 2004/048570) are mentioned, for example.

(SEQ ID NO: 1)
(DMD AO01) HO-C$^{e2s}$-A$^{m1s}$-G$^{m1s}$-T$^{e2s}$_T$^{e2s}$-U$^{m1s}$-
G$^{m1s}$-C$^{e2s}$-C$^{e2s}$-G$^{m1s}$-C$^{e2s}$-T$^{e2s}$-G$^{m1s}$-C$^{e2s}$-C$^{e2s}$
-C$^{e2s}$-A$^{m1s}$-A$^{m1s}$-CH$_2$CH$_2$OH;

(SEQ ID NO: 2)
(DMD AO02) HO-T$^{e2s}$-G$^{m1s}$-T$^{e2s}$-T$^{e2s}$-C$^{e2s}$-T$^{e2s}$-
G$^{m1s}$-A$^{m1s}$-C$^{e2s}$-A$^{m1s}$-A$^{m1s}$-C$^{e2s}$-A$^{m1s}$-G$^{m1s}$-T$^{e2s}$
-T$^{e2s}$-T$^{e2s}$-G$^{m1s}$-CH$_2$CH$_2$OH;

(SEQ ID NO: 3)
(DMD AO03) HO-C$^{e2s}$-G$^{m1s}$-Ce25-T$^{e2s}$-G$^{m1s}$-C$^{m1s}$-
C$^{e2s}$-C$^{e2s}$-A$^{m1s}$-A$^{m1s}$-T$^{e2s}$-G$^{m1s}$-C$^{e2s}$-C$^{e2s}$-A$^{m1s}$
-U$^{m1s}$-C$^{e2s}$-C$^{e2s}$-CH$_2$CH$_2$OH;

(SEQ ID NO: 4)
(DMD AO04) HO-C$^{e2s}$-A$^{m1s}$-T$^{e2s}$-A$^{m1s}$-A$^{m1s}$-T$^{e2s}$-
G$^{m1s}$-A$^{m1s}$-A$^{e2s}$-A$^{m1s}$-A$^{m1s}$-C$^{e2s}$-G$^{m1s}$-C$^{m1s}$-C$^{e2s}$
-G$^{m1s}$-C$^{e2s}$-C$^{e2s}$-CH$_2$CH$_2$OH;

(SEQ ID NO: 5)
(DMD AO05) HO-T$^{e2s}$-U$^{m1s}$C$^{e2s}$-C$^{m1s}$-C$^{e2s}$-Ande-A
$^{m1s}$-T$^{e2s}$-U$^{m1s}$-C$^{m1s}$-T$^{e2s}$-C$^{e2s}$-A$^{m1s}$-G$^{m1s}$-G$^{m1s}$-
A$^{e2s}$-A$^{m1s}$-T$^{e2s}$-CH$_2$CH$_2$OH;

(SEQ ID NO: 6)
(DMD AO06) HO-C$^{e2s}$-C$^{e2s}$-A$^{m1s}$-T$^{m1s}$-T$^{e2s}$-U$^{m1s}$-
G$^{m1s}$-T$^{e2s}$-A$^{m1s}$-U$^{m1s}$-T$^{e2s}$-T$^{e2s}$-A$^{m1s}$-G$^{m1s}$-C$^{e2s}$-
A$^{m1s}$-T$^{e2s}$-G$^{m1s}$-CH$_2$CH$_2$OH;

(SEQ ID NO: 7)
(DMD AO07) HO-G$^{m1s}$-G$^{m1s}$-C$^{e2s}$-T$^{e2s}$-G$^{m1s}$-C$^{m1s}$-
T$^{e2s}$-T$^{e2s}$-U$^{m1s}$-G$^{m1s}$-C$^{e2s}$-C$^{m1s}$-C$^{m1s}$-T$^{e2s}$-C$^{e2s}$
-A$^{m1s}$-G$^{m1s}$-C$^{e2s}$-CH$_2$CH$_2$OH;

(SEQ ID NO: 8)
(DMD AO08) HO-G$^{m1s}$-C$^{e2s}$-T$^{e2s}$-A$^{m1s}$-G$^{m1s}$-G$^{m1s}$-
T$^{e2s}$-C$^{e2s}$-A$^{m1s}$-G$^{m1s}$-G$^{m1s}$-T$^{e2s}$-G$^{m1s}$-C$^{m1s}$-T$^{e2s}$
-T$^{e2s}$-U$^{m1s}$-CH$_2$CH$_2$OH;

(SEQ ID NO: 9)
(DMD AO09) HO-A$^{m1s}$-C$^{e2s}$-C$^{e2s}$-G$^{m1s}$-C$^{m1s}$-C$^{e2s}$-
T$^{e2s}$-U$^{m1s}$-C$^{m1s}$-C$^{e2s}$-A$^{m1s}$-C$^{m1s}$-T$^{e2s}$-C$^{e2s}$-A$^{m1s}$
-G$^{m1s}$-A$^{e2s}$-G$^{m1s}$-CH$_2$CH$_2$OH;

(SEQ ID NO: 10)
(DMD AO10) HO-G$^{e2s}$-G$^{e2s}$-C$^{e2s}$-A$^{e2s}$-T$^{e2s}$-U$^{m1s}$-
U$^{m1s}$-C$^{m1s}$-U$^{m1s}$-A$^{m1s}$-G$^{m1s}$-U$^{m1s}$-t$^{m1s}$-Te25-G$^{e2s}$
-G$^{e2s}$-A$^{e2s}$-G$^{e2s}$-CH$_2$CH$_2$OH;

(SEQ ID NO: 11)
(DMD AO11) HO-G$^{m1s}$-G$^{m1s}$-C$^{e2s}$-A$^{m1s}$-T$^{e2s}$-T$^{e2s}$-
U$^{m1s}$-C$^{e2s}$-T$^{e2s}$-A$^{m1s}$-G$^{m1s}$-U$^{m1s}$-T$^{e2s}$-T$^{e2s}$-G$^{m1s}$
-G$^{m1s}$-A$^{e2s}$-G$^{m1s}$-CH$_2$CH$_2$OH;

-continued (SEQ ID NO: 12)
(DMD AO12) HO-A$^{e2s}$-G$^{m1s}$-T$^{e2s}$-U$^{m1s}$-T$^{e2s}$-G$^{m1s}$-
G$^{m1s}$-A$^{e2s}$-G$^{m1s}$-A$^{m1s}$-Tes-G$^{m1s}$-G$^{m1s}$-C$^{e2s}$-A$^{e2s}$-
G$^{m1s}$-T$^{e2s}$-T$^{e2s}$-CH$_2$CH$_2$OH;

(SEQ ID NO: 13)
(DMD AO13) HO-C$^{e2s}$-T$^{e2s}$-c$^{m1s}$-C$^{e2s}$-T$^{e2s}$-U$^{m1s}$-
C$^{e2s}$-Ce23-A$^{m1s}$-T$^{e2s}$-G$^{m1s}$-A$^{m1s}$-C$^{e2s}$-T$^{e2s}$-C$^{e2s}$-
A$^{m1s}$-A$^{m1s}$-G$^{m1s}$-CH$_2$CH$_2$OH;

(SEQ ID NO: 14)
(DMD AO14) HO-C$^{e2s}$-T$^{e2s}$-G$^{m1s}$-A$^{m1s}$-A$^{m1s}$-G$^{m1s}$-
G$^{m1s}$-T$^{e2s}$-G$^{m1s}$-T$^{e2s}$-T$^{e2s}$-C$^{e2s}$-T$^{e2s}$-T$^{e2s}$-G$^{m1s}$-
T$^{e2s}$-A$^{m1s}$-C$^{e2s}$-CH$_2$CH$_2$OH;

and (SEQ ID NO: 15)
(DMD AO15) HO-T$^{e2s}$-T$^{e2s}$-C$^{m1s}$-C$^{e2s}$-A$^{m1s}$-G$^{m1s}$-
C$^{e2s}$-C$^{e2s}$-A$^{m1s}$-T$^{e2s}$-T$^{e2s}$-G$^{m1s}$-T$^{e2s}$-G$^{m1s}$-T$^{e2s}$-
T$^{e2s}$-G$^{m1s}$-A$^{m1s}$-CH$_2$CH$_2$OH, wherein the left side represents the 5' end, and the right side represents the 3' end, A, G, C, U, and T respectively represent adenosine, guanosine, cytidine, uridine, and thymidine in which D-ribofuranose is modified and the carbon atom at the 5'-position is phosphorothioate-bound to the structural unit displayed on the left side, the e2s attached to each nucleotide or nucleoside indicates that D-ribofuranose is 2'-0,4'-C-ethylene-bridged, and the 3'-position binds to the carbon atom at the 5'-position of the nucleotide or nucleoside adjacent to the right side via —OP(═S)(—OH)—O—, the e2t attached thereto indicates that D-ribofuranose is 2'-O,4'-C-ethylene-bridged, and the 3'-position binds to the hydrogen atom at the 3' end via —O—, the mis attached thereto indicates that D-ribofuranose is 2'-O-methylated, and the 3'-position binds to the carbon atom at the 5'-position of the nucleotide or nucleoside adjacent to the right side via —OP(═S)(—OH)—O—, and the m1t attached thereto indicates that D-ribofuranose is 2'-O-methylated, and the 3'-position binds to the hydrogen atom at the 3' end via —O—.

As one aspect of the oligonucleotide to be produced by the method of the present invention, oligonucleotides, having the sequences and the structures represented by the following formulas, useful for treatment of glycogen storage disease type 1a (see International Publication No. WO 2019/172286) are mentioned, for example.

(SEQ ID NO: 16)
(GSDA001) X$^{18}$-A$^{m1s}$-A$^{e2s}$-g$^{m1s}$-C$^{m1s}$-C$^{e2s}$-G$^{m1s}$-
A$^{m1s}$-T$^{e2s}$-G$^{m1s}$-G$^{m1s}$-C$^{e2s}$-G$^{m1s}$-A$^{m1s}$-A$^{e2s}$-G$^{m1t}$
-H;

(SEQ ID NO: 17)
(GSDA002) X$^{18}$-A$^{e2s}$-U$^{m1s}$-C$^{m1s}$-C$^{e2s}$-G$^{m1s}$-A$^{m1s}$-
T$^{e2s}$-G$^{m1s}$-G$^{m1s}$-C$^{e2s}$-G$^{m1s}$-A$^{m1s}$-A$^{e2s}$-G$^{m1s}$-C$^{e2t}$
-H;

-continued (SEQ ID NO: 18)
(GSDA003) $X^{18}$-$U^{m1s}$-$C^{m1s}$-$C^{e2s}$-$G^{m1s}$-$A^{m1s}$-$T^{e2s}$-
$G^{m1s}$-$G^{m1s}$-$C^{e2s}$-$G^{m1s}$-$A^{m1s}$-$A^{s2s}$-$G^{m1s}$-$C^{e2s}$-$U^{m1t}$-
H;

(SEQ ID NO: 19)
(GSDA004) $X^{18}$-$A^{m1s}$-$A^{m1s}$-$A^{e2s}$-$U^{m1s}$-$C^{m1s}$-$C^{e2s}$-
$G^{m1s}$-$A^{m1s}$-$T^{e2s}$-$G^{m1s}$-$G^{m1s}$-$C^{e2s}$-$G^{m1s}$-$A^{m1s}$-$A^{e2s}$
-$G^{m1t}$-H;

(SEQ ID NO: 20)
(GSDA005) $X^{18}$-$A^{m1s}$-$A^{e2s}$-$U^{m1s}$-$C^{m1s}$-$C^{e2s}$-$G^{m1s}$-
$A^{m1s}$-$T^{e2s}$-$G^{m1s}$-$G^{m1s}$-$C^{e2s}$-$G^{m1s}$-$A^{m1s}$-$A^{e2s}$-$G^{m1s}$
-$C^{e2t}$-H;

(SEQ ID NO: 21)
(GSDA006) $X^{18}$-$A^{e2s}$-$U^{m1s}$-$C^{m1s}$-$C^{e2s}$-$G^{m1s}$-$A^{m1s}$-
$T^{e2s}$-$G^{m1s}$-$G^{m1s}$-$C^{e2s}$-$G^{m1s}$-$A^{m1s}$-$A^{e2s}$-$G^{m1s}$-$C^{e2s}$
-$U^{m1t}$-H;

(SEQ ID NO: 22)
(GSDA007) $X^{18}$-$A^{m1s}$-$A^{e2s}$-$U^{m1s}$-$C^{m1s}$-$C^{e2s}$-$G^{m1s}$-
$A^{m1s}$-$U^{m1s}$-$G^{m1s}$-$G^{m1s}$-$C^{e2s}$-$G^{m1s}$-$A^{m1s}$-$A^{e2s}$-$G^{m1t}$
-H;

(SEQ ID NO: 23)
(GSDA008) $X^{18}$-$A^{e2s}$-$U^{m1s}$-$C^{m1s}$-$C^{e2s}$-$G^{m1s}$-$A^{e2s}$-
$U^{m1s}$-$G^{m1s}$-$G^{m1s}$-$C^{e2s}$-$G^{m1s}$-$A^{m1s}$-$A^{e2s}$-$G^{m1s}$-$C^{e2t}$
-H;

(SEQ ID NO: 24)
(GSDA009) $X^{18}$-$U^{m1s}$-$C^{m1s}$-$C^{e2s}$-$G^{m1s}$-$A^{e2s}$-$U^{m1s}$-
$G^{m1s}$-$G^{m1s}$-$C^{e2s}$-$G^{m1s}$-$A^{m1s}$-Ae25-$G^{m1s}$-$C^{e2s}$-$U^{m1t}$-
H;

(SEQ ID NO: 25)
(GSDA010) $X^{18}$-$A^{m1s}$-$A^{m1s}$-$A^{e2s}$-$U^{m1s}$-$c^{m1s}$-$C^{e2s}$-
$G^{m1s}$-$A^{e2s}$-$U^{m1s}$-$G^{m1s}$-$G^{m1s}$-$C^{e2s}$-$G^{m1s}$-$A^{m1s}$-$A^{e2s}$
-Gmt-H;

(SEQ ID NO: 26)
(GSDA011) $X^{18}$-$A^{m1s}$-$A^{e2s}$-$U^{m1s}$-$C^{m1s}$-$C^{e2s}$-$G^{m1s}$-
$A^{e2s}$-$U^{m1s}$-$G^{m1s}$-$G^{m1s}$-$C^{e2s}$-$G^{m1s}$-$A^{m1s}$-Ae23-$G^{m1s}$-
$C^{e2t}$-H1;

(SEQ ID NO: 27)
(GSDA012) $X^{18}$-$A^{e2s}$-$U^{m1s}$-$C^{m1s}$-$C^{e2s}$-$G^{m1s}$-$A^{e2s}$-
$U^{m1s}$-$G^{m1s}$-$G^{m1s}$-$C^{e2s}$-$G^{m1s}$-$A^{m1s}$-$A^{e2s}$-$G^{m1s}$-$C^{e2s}$
-$U^{m1t}$-H;

(SEQ ID NO: 28)
(GSDA013) $X^{20}$-$A^{m1s}$-$A^{e2s}$-$U^{m1s}$-$c^{m1s}$-$C^{e2s}$-$G^{m1s}$-
$A^{e2s}$-$U^{m1s}$-$G^{m1s}$-$G^{m1s}$-$C^{e2s}$-$G^{m1s}$-$A^{m1s}$-$A^{e2s}$-$G^{m1t}$
-H;

-continued (SEQ ID NO: 29)
(GSDA014) $X^{20}$-$A^{e2s}$-$U^{m1s}$-$C^{m1s}$-$C^{e2s}$-$G^{m1s}$-$A^{e2s}$-
$U^{m1s}$-$G^{m1s}$-$c^{m1s}$-$C^{e2s}$-$G^{m1s}$-$A^{m1s}$-$A^{e2s}$-$G^{m1s}$-$C^{e2t}$-
H;

(SEQ ID NO: 30)
(GSDA015) $X^{20}$-$A^{m1s}$-$A^{m1s}$-$A^{e2s}$-$U^{m1s}$-$C^{m1s}$-$C^{e2s}$-
$G^{m1s}$-$A^{e2s}$-$U^{m1s}$-$G^{m1s}$-$G^{m1s}$-$C^{e2s}$-$G^{m1s}$-$A^{m1s}$-$A^{e2s}$
-$G^{m1t}$-H;

and (SEQ ID NO: 31)
(GSDA016) $X^{20}$-$A^{m1s}$-$A^{e2s}$-$U^{m1s}$-$C^{m1s}$-$C^{e2s}$-$G^{m1s}$-
$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-
$C^{e2t}$-H, wherein the left side represents the 5' end, and the right side represents the 3' end, A, G, C, U, and T respectively represent adenosine, guanosine, cytidine, uridine, and thymidine in which D-ribofuranose is modified and the carbon atom at the 5'-position is phosphorothioate-bound to the structural unit displayed on the left side, the e2s attached to each nucleotide or nucleoside indicates that D-ribofuranose is 2'-0,4'-C-ethylene-bridged, and the 3'-position binds to the carbon atom at the 5'-position of the nucleotide or nucleoside adjacent to the right side via —OP(═S)(—OH)—O—, the e2t attached thereto indicates that D-ribofuranose is 2'-O,4'-C-ethylene-bridged, and the 3'-position binds to the hydrogen atom at the 3' end via —O—, the mis attached thereto indicates that D-ribofuranose is 2'-O-methylated, and the 3'-position binds to the carbon atom at the 5'-position of the nucleotide or nucleoside adjacent to the right side via —OP(═S)(—OH)—O—, the m1t attached thereto indicates that D-ribofuranose is 2'-O-methylated, and the 3'-position binds to the hydrogen atom at the 3' end via —O—, and $X^{18}$ and $X^{20}$ respectively represent GalNAc units represented by the following formulas, wherein the bond bound to the phosphate group indicates its bonding to the carbon atom at the 5' end of the oligonucleotide to form a phosphodiester bond:

[Formula 80]

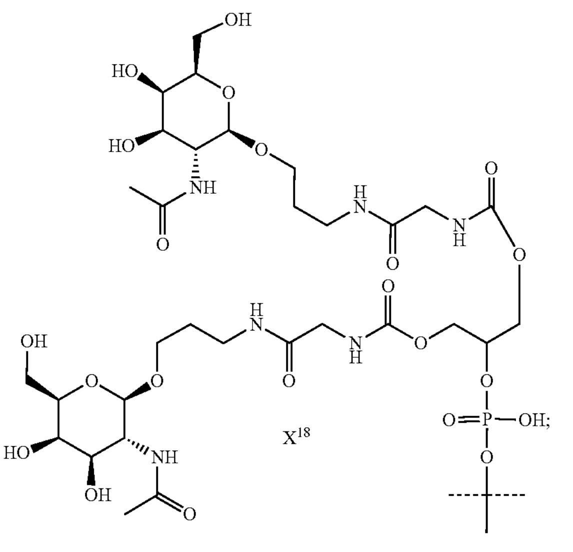

$X^{18}$

-continued

[Formula 81]

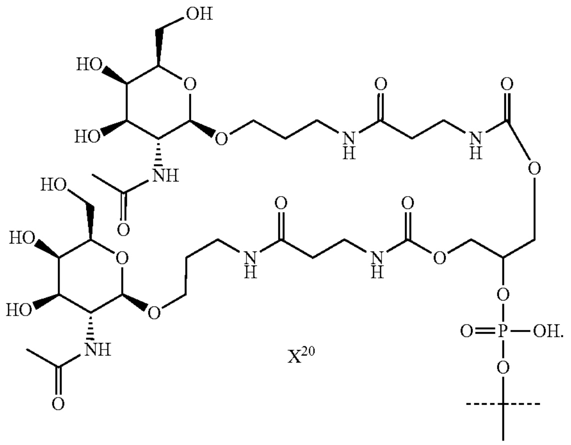

EXAMPLES

Hereinafter, the present invention will be described further specifically by way of Examples, but the scope of the present invention is not limited to these Examples.

(Example 1) Production of 2,6-anhydro-3-O-benzyl-4-[(benzyloxy)methyl]-5-deoxy-α-L-lyxo-hexofuranose (Compound 2)

(Example 1-1) Production of dimethylacetamide Solution of (3aR, 3bR, 6S, 6aS, 7aR)-6-hydroxy-2,2-dimethyltetrahydro-2H-furo[ 2',3':4,5] furo[2,3-d][1,3]dioxole-5(3bH)-one (Compound 5)

[Formula 82]

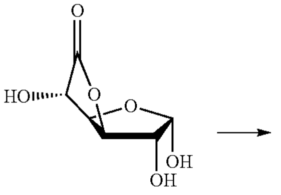

4

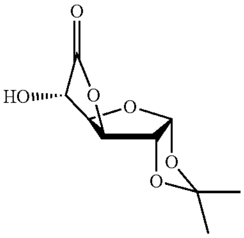

5

To acetone (11.9 kg) were added a commercially available (2R)-2-[(2S,3R,4S)-3,4-dihydroxy-5-oxo-tetrahydrofuran-2-yl]-2-hydroxy-acetaldehyde (Compound 4) (1.00 kg, 5.678 mol) and concentrated sulfuric acid (114 g, 1.162 mol) in this order, followed by stirring at 40 to 50° C. for 17 hours. The reaction solution was cooled to 20 to 30° C., and sodium bicarbonate (0.19 kg, 2.271 mol) was added thereto, followed by stirring for 2 hours. Then, the white solid generated was filtered out and washed with acetone (2.37 kg), and the washing solution was added to the filtrate. The operation of adding dimethylacetamide (7.50 kg) and toluene (4.34 kg) to the solution thus obtained, followed by concentration under reduced pressure, and further adding toluene (4.34 kg) thereto, followed by concentration under reduced pressure, was repeated twice, to obtain a dimethylacetamide solution of a compound 5.

The structure was partially subjected to silica gel column purification (hexane/ethyl acetate) and confirmed by NMR.

$^1$H NMR ($CDCl_3$) δ=1.36 (3H, s), 1.53 (3H, s), 2.72 (1H, d, J=9.5 Hz), 4.50 (1H, dd, J=4.5, 9.5 Hz), 4.84 (2H, d, J=2.5 Hz), 4.95 (1H, dd, J=2.5, 4.5 Hz), 5.99 (1H, d, J=3.5 Hz).

(Example 1-2) Production of (3aR,3bR,6S,6aR,7aR)-2,2-dimethyl-5-oxohexahydro-2H-furo[2',3':4,5] furo[2,3-d][1,3]dioxole-6-yl=4-methylbenzene-1-sulfonate (compound 6)

[Formula 83]

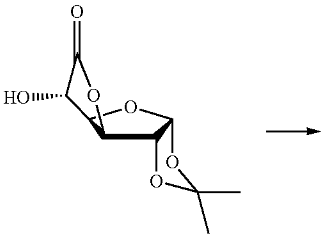

5

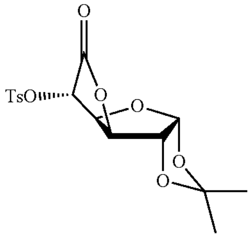

6

To the dimethylacetamide solution of the compound 5 obtained in Example 1-1 were added 1-methylimidazole (0.56 kg, 6.814 mol) and p-toluenesulfonyl chloride (1.24 kg, 6.530 mol) in this order, followed by stirring at 20 to 30° C. for 3 hours. Water (5 kg) was added to the reaction solution, followed by stirring for 3 hours, then cooling to 0 to 5° C., and further stirring for 2 hours. The white solid generated in the reaction solution was collected by filtration and washed with water/dimethylacetamide (1/1, 4 kg) and water (8 kg) in this order. The solid obtained was dried under reduced pressure (40° C.), to obtain a compound 6 (1.66 kg, yield 79.4%).

$^1$H NMR ($CDCl_3$): δ=1.33 (3H, s), 1.49 (3H, s), 2.45 (3H, s), 4.78 (1H, d, J=3.5 Hz), 4.83 (1H, d, J=3.0 Hz), 4.97 (1H, dd, J=3.0, 4.5 Hz), 5.22 (1H, d, J=4.5 Hz), 5.97 (1H, d, J=3.5 Hz), 7.37 (2H, d, J=8.0 Hz), 7.89 (2H, m).

(Example 1-3) Production of toluene Solution of 5-deoxy-1,2-O-(1-methylethylidene)-O-D-xylo-hexofuranose (Compound 7)

[Formula 84]

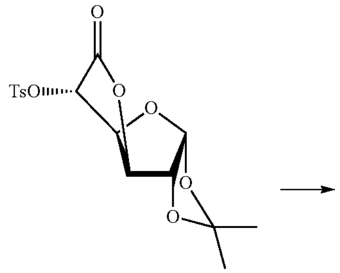

6

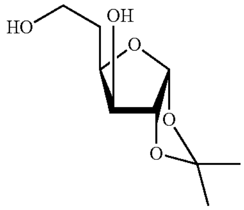

7

To tetrahydrofuran (22.1 kg, 15.0 v/w) adjusted to 0 to 10° C. were added sodium bis(2-methoxyethoxy)aluminum hydride (4.53 kg, 15.69 mol) and the compound 6 (1.66 kg, 4.48 mol) obtained in Example 1-2 in this order, followed by stirring for 30 minutes and then further stirring at 20 to 30° C. for 1.5 hours. After the reaction, the reaction solution was cooled to 0 to 10° C., acetone (1.05 kg, 0.8 v/w) and a 50% aqueous L-potassium sodium tartrate solution (17.0 kg, 8.0 v/w) were added dropwise thereto, and the reaction solution was heated to 40 to 50° C., followed by stirring for 14 hours and then liquid separation at 40 to 50° C. To the organic layer obtained was added 20% saline (3.81 kg, 2.0 v/w) at 40 to 50° C., to obtain a tetrahydrofuran layer by liquid separation. To the solution obtained by repeating the same liquid separation twice was added toluene (7.20 kg, 5.0 v/w), followed by concentration under reduced pressure to a volume of 3.3 L. To the solution obtained by repeating the same concentration under reduced pressure 3 times was added toluene (20.0 kg, 13.6 w/w), to obtain a toluene solution of a compound 7.

The structure was partially subjected to silica gel column purification (hexane/ethyl acetate) and confirmed by NMR.

$^1$H NMR ($CDCl_3$) δ=1.32 (3H, s), 1.51 (3H, s), 1.94-2.06 (2H, m), 2.46 (1H, br), 3.26 (1H, br), 3.75 (1H, td, J=3.5, 9.5 Hz), 3.87-3.91 (1H, m), 4.11 (1H, d, J=7.5 Hz), 4.26 (1H, td, J=3.0, 6.0 Hz), 4.55 (1H, d, J=4.0 Hz), 5.91 (1H, d, J=4.0 Hz).

(Example 1-4) Production of toluene Solution of 5-deoxy-1,2-O-(1-methylethylidene)-6-O-(triphenylmethyl)-α-D-xylo-hexofuranose (Compound 8)

[Formula 85]

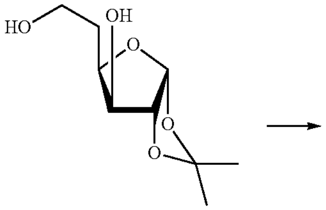

7

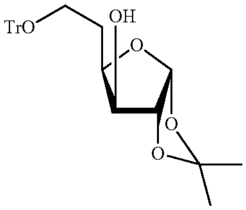

8

To the toluene solution of the compound 7 obtained in Example 1-3 were added trityl chloride (0.87 kg, 3.14 mol) and 4-methylmorpholine (0.54 kg, 5.38 mol) in this order, followed by stirring at 50 to 60° C. for 3.5 hours. After the reaction, the reaction solution was cooled to 20 to 30° C., and 8% aqueous sodium bicarbonate (3.42 kg, 2.0 v/w) was added thereto for liquid separation, to obtain a toluene layer. To the toluene layer obtained was added 5% saline (10.26 kg, 6.0 v/w) for liquid separation. The toluene layer obtained was subjected to the same liquid separation 3 times, to obtain a toluene solution of a compound 8.

The structure was partially subjected to silica gel column purification (hexane/ethyl acetate) and confirmed by NMR.

$^1$H NMR ($CDCl_3$): δ=1.31 (3H, s), 1.48 (3H, s), 1.99-2.02 (2H, m), 2.77 (1H, d, J=4.0 Hz), 3.15-3.19 (1H, m), 3.40 (1H, ddd, J=4.5, 5.0, 10.0 Hz), 4.08 (1H, t, J=2.5 Hz), 4.25 (1H, ddd, J=2.5, 7.0, 7.5 Hz), 4.53 (1H, d, J=3.5 Hz), 5.88 (1H, d, J=3.5 Hz), 7.23-7.26 (3H, m), 7.29-7.32 (6H, m), 7.39-7.41 (6H, m).

(Example 1-5a) Production of toluene Solution of 5-deoxy-1,2-O-(1-methylethylidene)-6-O-(triphenylmethyl)-α-D-erythro-hexofuranos-3-ulose (Compound 9)

[Formula 86]

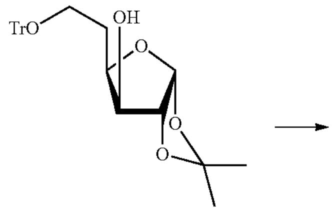

8

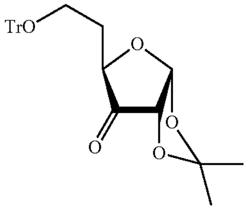

9

To the toluene solution of the compound 8 obtained in Example 1-4 were added 8% aqueous sodium bicarbonate (5.13 kg, 3.0 v/w), potassium bromide (53.0 g, 0.45 mol), and 9-azanoradamantane-N-oxyl (6.2 g, 44.82 mmol) at room temperature. The temperature of the resultant solution was adjusted to 0 to 10° C., and then sodium hypochlorite/pentahydrate (2.21 kg, 13.45 mol) was added thereto, followed by stirring for 1.5 hours. After the reaction, the reaction solution was subjected to liquid separation, to obtain a toluene layer. The operation of washing the toluene layer obtained with a 5% aqueous sodium sulfite solution (5.22 kg, 3.0 v/w) and 20% saline (3.80 kg, 2.0 v/w) in this order was repeated twice, to obtain a toluene solution of a compound 9.

The structure was partially subjected to silica gel column purification (hexane/ethyl acetate) and confirmed by NMR.

$^1$H NMR ($CDCl_3$): δ=1.36 (3H, s), 1.44 (3H, s), 1.96-2.01 (1H, m), 2.21-2.28 (1H, m), 3.06(1H, ddd, J=3.0, 4.5, 10.0 Hz), 3.30 (1H, ddd, J=4.0, 4.5, 9.0 Hz), 4.33 (1H, dd, J=1.0, 4.5 Hz), 4.49 (1H, dd, J=3.5, 5.5 Hz), 5.60 (1H, d, J=4.5), 7.21-7.25 (3H, m), 7.29-7.32 (6H, m), 7.35-7.37 (6H, m).

High-Performance Liquid Chromatography (HPLC) Analysis Conditions

Column: Xbridge C18 3.5 μm, 4.6×150 mm

Column temperature: 40° C.

Mobile phase A: 10 mM aqueous ammonium acetate solution

Mobile phase B: Acetonitrile

Gradient conditions: B (%) 30% (0 to 3 min), 30 to 95% (3 to 20 min), 95% (20 to 23 min)

Flow rate: 1.0 mL/min

Detection wavelength: 210 nm

Retention time of compound 9: 13.9 min and 17.5 min (Example 1-5b) Production of toluene Solution of 5-deoxy-1,2-O-(1-methylethylidene)-6-O-(triphenylmethyl)-α-D-erythro-hexofuranos-3-ulose (Compound 9)

To the toluene solution (30 mL) of the compound 8 obtained in Example 1-4 were added 8% aqueous sodium bicarbonate (6.0 mL, 3.0 v/w), potassium bromide (60.0 mg, 0.54 mmol), and 9-azanoradamantane-N-oxyl (3.7 mg, 0.03 mmol) at room temperature. The temperature of the resultant solution was adjusted to 0 to 10° C., and then an aqueous sodium hypochlorite solution (6.48 g, 10.80 mmol) was added thereto at 10° C. or less, followed by stirring at 0° C. for 2 hours. After completion of the reaction, a 15% aqueous sodium sulfite solution (12.0 mL, 6.0 v/w) was added thereto, followed by stirring at room temperature for 1 hour. The reaction solution was subjected to liquid separation, to obtain a toluene layer. The toluene layer obtained was washed with 20% saline (4.0 mL, 2.0 v/w), to obtain a toluene solution of a compound 9. The retention time in HPLC analysis of the compound obtained herein was consistent with the retention time in HPLC analysis of the compound obtained in (Example 1-5a).

(Example 1-6) Production of Mixed toluene Solution of 5-deoxy-4-(hydroxymethyl)-1,2-O-(1-methylethylidene)-6-O-(triphenylmethyl)-β-L-threo-hexofuranos-3-ulose (Compound 10) and (3aS,3bR,7aR,8aR)-2,2-dimethyl-7a-[2 -(triphenyl methoxy)ethyl] tetrahydro-2H,3bH,5H-[1,3]dioxolo[4,5] furo[3,2-d][1,3]dioxin-3b-ol (compound 11)

[Formula 87]

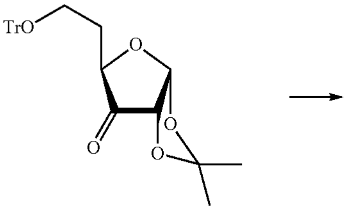

9

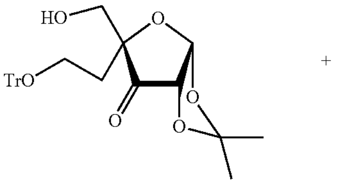

10

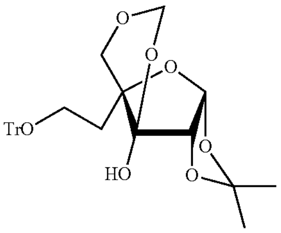

11

To the toluene solution of the compound 9 obtained in Example 1-5 were added a 37% aqueous formaldehyde solution (1.81 kg, 1.0 v/w) and 1,8-diazabicyclo[5.4.0]undec-7-ene (2.05 kg, 13.45 mol), followed by stirring at 20 to 30° C. for 1.5 hours. After the reaction, the reaction solution was subjected to liquid separation, to obtain a toluene layer. To the toluene layer obtained was added a 20% aqueous citric acid solution (3.59 kg, 2.0 v/w) for liquid separation, to obtain a toluene layer. To the toluene layer obtained was added 8% aqueous sodium bicarbonate (1.71 kg, 1.0 v/w) for liquid separation, to obtain a toluene solution of compounds 10 and 11.

(Example 1-7) Production of toluene Solution of 5-deoxy-4-(hydroxymethyl)-1,2-O-(1-methylethylidene)-6-O-(triphenylmethyl)-β-L-lyxo-hexofuranose (Compound 12)

[Formula 88]

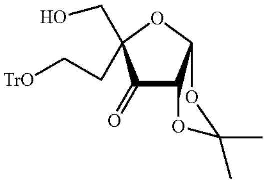

+

10

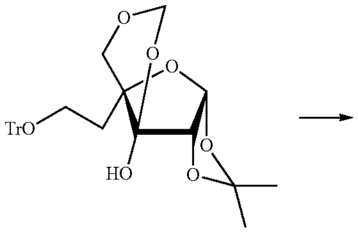

11

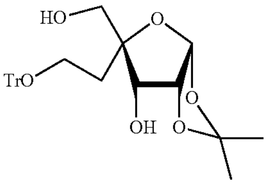

12

To the toluene solution of the compounds 10 and 11 obtained in Example 1-6 were added water (4.98 kg, 3.0 v/w) and sodium borohydride (0.34 kg, 8.96 mol) at 20 to 30° C., followed by stirring for 2 hours. After the reaction, the reaction solution was cooled to 0 to 10° C., and a 20% aqueous citric acid solution (5.37 kg, 3.0 v/w) was added thereto at the same temperature for liquid separation, to obtain a toluene layer. To the toluene layer obtained was added 8% aqueous sodium bicarbonate (3.42 kg, 2.0 v/w) for liquid separation, to obtain a toluene solution of a compound 12.

The structure was partially subjected to silica gel column purification (hexane/ethyl acetate) and confirmed by NMR.

$^1$H NMR ($CDCl_3$) δ=1.33 (3H, s), 1.55 (3H, s), 1.99 (1H, ddd, J=6.5, 8.0, 14.0 Hz), 2.20(1H, dt, J=6.0, 14.5 Hz), 2.85 (1H, br), 3.20-3.25 (1H, m), 3.35-3.42 (2H, m), 3.51 (1H, d, J=12.0 Hz), 4.21 (1H, d, J=6.0 Hz), 4.63 (1H, dd, J=4.0, 6.0 Hz), 5.73 (1H, d, J=4.0), 7.21-7.25 (3H, m), 7.27-7.30 (6H, m), 7.41-7.44 (6H, m).

(Example 1-8) Production of 3-O-benzyl-4-[(benzyloxy)methyl]-5-deoxy-1,2-O-(1-methylethylidene)-6-O-(triphenylmethyl)-f-L-lyxo-hexofuranose (Compound 13)

[Formula 89]

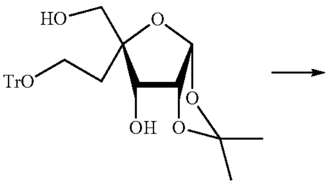

12

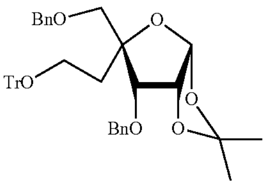

13

To the toluene solution obtained in Example 1-7 were added a 48% aqueous potassium hydroxide solution (7.27 kg, 3.0 v/w), tetrabutylammonium iodide (0.20 kg, 0.54 mol), and benzyl bromide (1.53 kg, 8.96 mol), followed by stirring at 65 to 75° C. for 23 hours. After the reaction, water (6.64 kg, 4.0 v/w) and N-acetyl-L-cysteine (0.50 kg, 0.3 w/w) were added to the reaction solution at 45 to 55° C., followed by stirring for 2 hours. The reaction solution was cooled to 20 to 30° C., and then water (4.98 kg, 3.0 v/w) was added thereto for liquid separation, to obtain a toluene layer. To the toluene layer obtained was added 8% aqueous sodium bicarbonate (3.42 kg, 2.0 v/w) for liquid separation, to obtain a toluene layer. To the toluene solution obtained was added 10% saline (3.55 kg, 2.0 v/w) for liquid separation, to obtain a toluene layer. The toluene layer obtained was concentrated to 3.3 L, 1-propanol (5.34 kg, 4.0 v/w) was added, and the insoluble matter was filtered. The mixture was further concentrated to 3.0 L under reduced pressure, and 1-propanol (0.60 kg) was further added thereto, followed by stirring at 45 to 55° C. for 0.5 hours, to confirm precipitation of crystals. After stirring at 20 to 30° C. for 12.5 hours and stirring at 0 to 10° C. for 2 hours, the precipitated crystals were collected by filtration. The crystals obtained were washed with 1-propanol (4.00 kg, 3.0 v/w) cooled to 0° C. in advance and dried under reduced pressure (40° C.), to obtain a compound 13 (1.25 kg, 1.90 mol, yield 42.5%).

$^1$H NMR ($CDCl_3$): δ=1.29 (3H, s), 1.51 (3H, s), 1.90-1.96 (1H, m), 2.43-2.49 (1H, m), 3.21-3.32 (3H, m), 3.47 (1H, d, J=10.5 Hz), 4.10 (1H, d, J=5.5 Hz), 4.30(1H, d, J=12.0 Hz), 4.42 (1H, d, J=11.5 Hz), 4.47 (1H, d, J=12.0 Hz), 4.57 (1H, dd, J=5.5, 4.0 Hz), 4.69 (1H, d, J=12.0 Hz), 5.69 (1H, d, J=4.0 Hz), 7.15-7.34 (19H, m), 7.39-7.41 (6H, m).

(Example 1-9) Production of toluene Solution of methyl=3-O-benzyl-4-[(benzyloxy)methyl]-5-deoxy-α-L-lyxo-hexofuranoside (Compound 14)

[Formula 90]

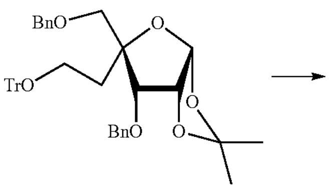

13

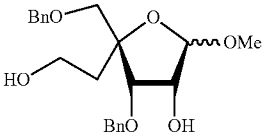

14

To a methanol (1250 mL) solution of the compound 13 (250.0 g, 380.6 mmol) obtained in Example 1-8 was added concentrated sulfuric acid (3.73 g, 0.0380 mmol), and the reaction solution was stirred at 40 to 50° C. for 20 hours. The reaction solution was cooled to 20 to 30° C., methoxytriphenyl methane (25 mg) and triethylamine (13.56 g, 134.0 mmol) were added thereto, followed by stirring for 2 hours, and then water (250 mL) was added dropwise over 1.5 hours. The reaction solution was stirred for 50 minutes, and then the white solid generated was filtered out and washed with methanol/water (5/1,500 mL). To the solution obtained was added n-heptane (1250 mL) for liquid separation, and to the lower layer (aqueous layer) was added n-heptane (500 mL) for liquid separation. To the lower layer were added 20% saline (1250 mL) and toluene (1250 mL) for liquid separation, to obtain a toluene layer and an aqueous layer. Thereafter, toluene (1250 mL) was added to the aqueous layer for liquid separation, and the toluene layers obtained were combined therewith, followed by concentration under reduced pressure, to obtain a toluene solution (625 mL) of a compound 14.

The structure was partially subjected to silica gel column purification (hexane/ethyl acetate) and confirmed by NMR.

$^1$H NMR (β-form,$CDCl_3$): δ=2.00-2.05 (1H, m), 2.10-2.16 (1H, m), 3.29 (3H, s), 3.35 (1H, d, J=9.0 Hz), 3.55 (1H, d, J=9.0 Hz), 3.76-381 (1H, m), 3.85-3.90 (1H, m), 4.08 (2H, dd, J=5.0, 15.0 Hz), 4.54 (2H, s), 4.63 (2H, s), 4.87 (1H, s), 7.26-7.36 (10H, m).

(Example 1-10) Production of toluene Solution of methyl=2,6-anhydro-3-O-benzyl-4-[(benzyloxy)methyl]-5-deoxy-α-L-lyxo-hexofuranoside (Compound 15)

[Formula 91]

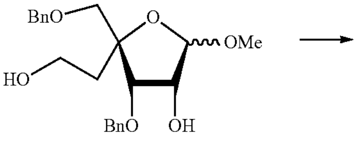

14

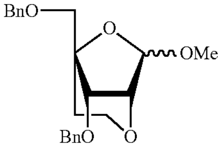

15

To the toluene solution of the compound 14 obtained in Example 1-9 was added triphenylphosphine (89.85 g, 342.6 mmol), followed by cooling to 0 to 5° C. Thereafter, a toluene (180.3 mL) solution of diisopropyl azodicarboxylate (69.27 g, 342.6 mmol) was added dropwise thereto over 20 minutes, and the reaction solution was stirred at 20 to 30° C. for 3 hours. To the reaction solution was added magnesium chloride (90.60 g, 951.6 mmol), followed by stirring for 6 hours, and n-heptane (1500 mL) was added thereto, followed by stirring for 23 hours, cooling to 0 to 5° C., and stirring for 2 hours. The white solid generated was filtered out and washed with toluene/n-heptane (1/2,750 mL), and then methanol/water (3/2,750 mL) was added to the solution obtained for liquid separation. To the organic layer obtained was added methanol/water (3/2,750 mL) for liquid separation, and the organic layer was then concentrated under reduced pressure, to prepare a toluene solution (625 mL) of a compound 15.

The structure was partially subjected to silica gel column purification (hexane/ethyl acetate) and confirmed by NMR.

$^1$H NMR (β-form,$CDCl_3$): δ=1.51 (1H, dd, J=3.5, 13.0 Hz), 2.19 (1H, ddd, J=7.5, 11.0, 13.5 Hz), 3.41 (3H, s), 3.53 (2H, dd, J=10.5, 30.5 Hz), 3.86-3.95 (3H, m), 4.08 (1H, d, J=3.0 Hz), 4.53 (1H, d, J=11.5 Hz), 4.61 (2H, dd, J=12.0, 27.5 Hz), 4.71 (1H, d, J=6.5 Hz), 5.10 (1H, s), 7.26-7.35 (10H, m).

(Example 1-11) Production of Compound 2

[Formula 92]

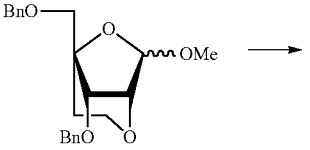

15

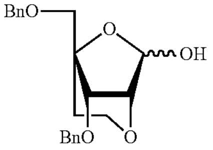

2

To the toluene solution (625 mL) of the compound 15 obtained in Example 1-10 was added water (625 mL), followed by concentration under reduced pressure, to obtain a water mixture (625 mL) of the compound 15. To the mixture were added acetic acid (750 mL) and concentrated hydrochloric acid (125 mL) in this order, followed by stirring at 20 to 30° C. for 3 hours, and then a compound 2 (25 mg) was added thereto, followed by cooling to 0 to 5° C. and stirring for 17 hours. To the mixture was added water (750 mL), followed by stirring at 0 to 5° C. for 17 hours, and then the crystals precipitated were collected by filtration and washed with acetic acid/water (1/2,500 mL) cooled to 0 to 5° C. in advance and water (500 mL) sequentially, to obtain a wet product of a crude compound 2. The crude compound 2 obtained was dissolved in toluene (1250 mL) at 35 to 45° C., and the aqueous layer generated was removed by liquid separation. The organic layer obtained was concentrated under reduced pressure to give a toluene solution (750 mL) of the compound 2, and n-heptane (375 mL) was added thereto, followed by cooling to 20 to 30° C. To this solution were added seed crystals (25 mg) of the compound 2, followed by stirring at 20 to 30° C. for 2 hours, and n-heptane (1125 mL) was added thereto, followed by stirring at 0 to 5° C. for 19 hours. The crystals precipitated were collected by filtration and washed with toluene/n-heptane (1/2,750 mL) and then with n-heptane (750 mL). The crystals obtained were dried under reduced pressure (40° C.) to obtain the compound 2 (76.84 g, 215.6 mmol, yield 56.6%).

The seed crystals of the compound 2 to be used in Example 1-11 were obtained by the following method. The crude compound 2 was obtained as crystals by the same method as the first half step of Example 1-11. Using the crude compound 2 obtained, the compound 2 was obtained as crystals by the same method as the second step of Example 1-11. As the seed crystals of the compound 2, the crystals of the crude compound 2 previously obtained were used. The crystals of the compound 2 obtained by the aforementioned method were used as the seed crystals of the compound 2 in Example 1-11.

$^1$H NMR ($CDCl_3$): δ=1.30 (0.39H, d, J=10.8 Hz), 1.45 (0.59H, dd, J=10.6, 3.2 Hz),1.97-2.07 (0.39H, m), 2.13-2.22 (0.64H, m), 2.60 (0.34H, d, J=1.2 Hz), 2.80(0.49H, brs), 3.22 (0.36H, d, J=7.2 Hz), 3.45-3.59 (1.41H, m), 3.71 (0.37H,d, J=7.2 Hz), 3.78 (0.37H, brs), 3.82 (0.37H, ddd, J=9.2, 4.0, 1.6 Hz),3.85-3.95 (1.23H, m), 4.01-4.13 (1.30H, m), 4.16-4.27 (0.83H, m), 4.44-4.75(4.24H, m), 5.36 (0.07H, dd, J=7.0, 1.6 Hz), 5.57 (0.57H, s), 7.24-7.39 (10H, m), 9.89 (0.36H, s).

(Example 1-12) Purification of Compound 2

The crude compound 2 (50 g) obtained in Example 1-11 was dissolved in toluene (300 mL), and n-heptane (300 mL) was added thereto, followed by stirring at 20 to 30° C. for 3 hours. Further, n-heptane (300 mL) was added thereto, followed by stirring for 16 hours. The crystals precipitated were collected by filtration and washed with toluene/n-heptane (1/2,250 mL) and further with n-heptane (250 mL). The crystals obtained were dried under reduced pressure (40° C.), to obtain the compound 2 (40.06 g, yield 80.1%).

(Example 2) Production of 1-(2,6-anhydro-4-{[bis (4-methoxyphenyl) (phenyl)methoxy]methyl}-3-O-{ (2-cyanoethoxy) [di(propane-2-yl)amino]phosphanyl}-5-deoxy-a-L-lyxo-hexofuranosyl)-5-methylpyrimidine-2,4(1H,3H)-dione (Compound 1t)

(Example 2-1) Production of methanol Solution of 1-{2,6-anhydro-3-O-benzyl-4-[(benzyloxy)methyl]-5-deoxy-α-L-lyxo-hexofuranosyl}-5-methylpyrimidine-2,4(1H,3H)-dione (Compound 3t)

[Formula 93]

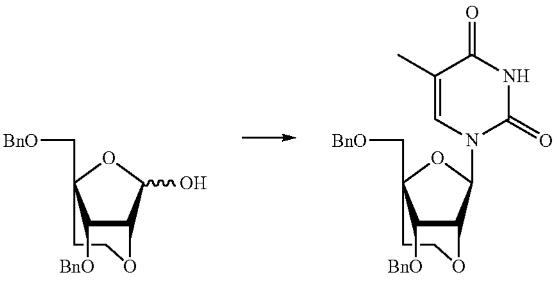

2

3t

To acetonitrile (50 mL) were added thymine (8.85 g, 70.18 mmol) and N,O-bistrimethylsilylacetamide (28.6 g, 140.6 mmol), followed by stirring at 20 to 30° C. for 1 hour, to give a solution A. To acetonitrile (100 mL) in another reaction container were added the compound 2 (20.00 g, 56.12 mmol) obtained in Example 1 and trichloroacetonitrile (15.20 g, 105.27 mmol), and 1,8-diazabicyclo[5.4.0]undec-7-ene (1.07 g, 7.02 mmol) was further added thereto, followed by stirring at 20 to 30° C. for 1 hour, to give a solution B. The solution A was added to the solution B, and then iodotrimethylsilane (17.55 g, 87.73 mmol) was added thereto, followed by stirring at 20 to 30° C. for 2 hours. To the reaction solution was added an aqueous solution obtained by dissolving sodium sulfite (17.68 g, 175.45 mmol) in a 5% aqueous sodium bicarbonate solution (160 mL) dropwise, and toluene (200 mL) and methanol (80 mL) were added thereto, followed by stirring at 35 to 45° C. and liquid separation. To the organic layer obtained was added 40% methanol water (200 mL), followed by stirring at 35 to 45° C. and liquid separation. The organic layer obtained after another liquid separation with 40% methanol water (200 mL) was concentrated under reduced pressure, to give a methanol solution (50 mL), then methanol (200 mL) was added thereto, followed by concentration under reduced pressure again, to give a methanol solution (50 mL) of a compound 3t.

The NMR spectrum of the compound obtained was consistent with the NMR spectrum of the compound according to Example 6 of International Publication No. WO 00/47599.

(Example 2-2) Production of 1-[2,6-anhydro-5-deoxy-4-(hydroxymethyl)-α-L-lyxo-hexofuranosyl]-5-methylpyrimidine-2,4 (1H,3H)-dione (Compound 16)

[Formula 94]

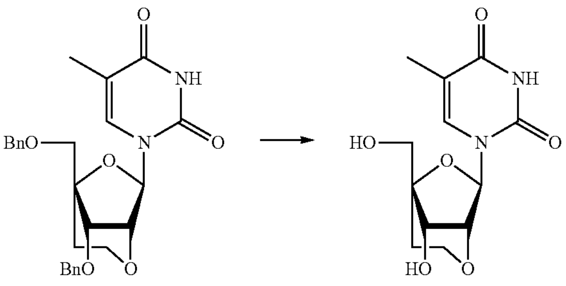

3t 16

To the methanol solution (50 mL) of the compound 3t obtained in Example 2-1 were further added methanol (50 mL) and palladium hydroxide (1.0 g), followed by stirring at 55 to 65° C. for 2 hours under a hydrogen atmosphere. Thereafter, the catalyst was filtered at the same temperature, and the filtrate obtained was concentrated under reduced pressure, to give a methanol solution (50 mL). Then, acetone (200 mL) was added thereto, followed by concentration to 50 mL under reduced pressure. Acetone (100 mL) was further added thereto, followed by cooling to 0 to 5° C. and stirring for 2 hours. The crystals generated were collected by filtration and washed with acetone (50 mL). The crystals obtained were dried under reduced pressure (40° C.), to obtain a compound 16 (9.95 g, yield 62.4% (from the compound 2)).

The NMR spectrum of the compound obtained was consistent with the NMR spectrum of the compound according to Example 7 of International Publication No. WO 00/47599.

(Example 2-3) Production of 1-(2,6-anhydro-4-{[bis (4-methoxyphenyl) (phenyl)methoxy]methyl}-5-deoxy-α-L-lyxo-hexofuranosyl)-5-methylpyrimidine-2,4(1H,3H)-dione (Compound 17)

[Formula 95]

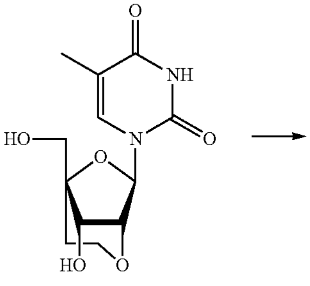

16

-continued

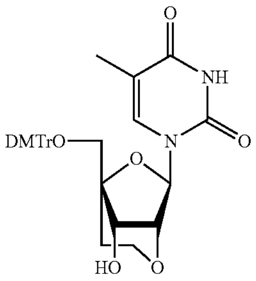

17

To tetrahydrofuran (47.5 mL) were added the compound 16 (9.50 g, 33.42 mmol) obtained in Example 2-2 and pyridine (10.57 g, 133.68 mmol), then 4,4'-dimethoxytrityl chloride (13.59 g, 40.10 mmol) was added thereto, and the reaction solution was stirred at 20 to 30° C. for 2 hours. To the reaction solution was added methanol (1.62 mL, 40.10 mmol), and a 15% aqueous sodium carbonate solution (28.5 mL), ethyl acetate (133 mL), and water (67 mL) were added thereto in this order, followed by washing for liquid separation. Thereafter, the organic layer obtained was washed with a 20% aqueous citric acid solution (47.5 mL) twice and further washed with a 15% aqueous sodium carbonate solution (47.5 mL) and water (47.5 mL) sequentially, followed by concentration under reduced pressure to 47.5 mL. To the concentrate obtained was added ethyl acetate (100 mL), followed by concentration under reduced pressure to 100 mL. The concentrate obtained was stirred at 55 to 65° C. for 16 hours and further stirred at 20 to 30° C. for 5 hours, and n-heptane (50 mL) was added thereto, followed by further stirring for 16 hours, to collect the precipitated solid by filtration. The solid obtained was washed with ethyl acetate/n-heptane (2/1,47.5 mL) and then dried under reduced pressure (40° C.), to obtain a compound 17 (17.35 g, 88.5%).

The NMR spectrum of the compound obtained was consistent with the NMR spectrum of the compound according to Example 8 of International Publication No. WO 00/47599.

(Example 2-4) Production of Compound 1t

[Formula 96]

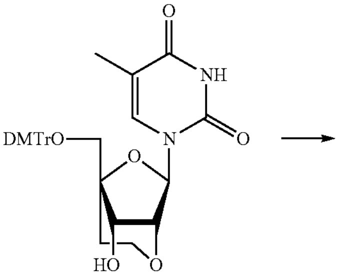

17

-continued

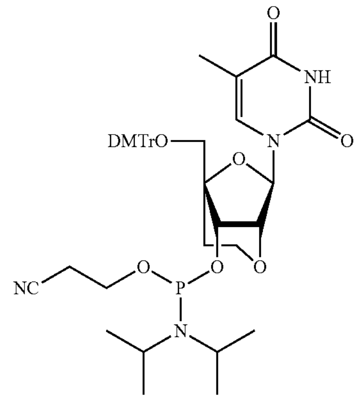

1t

To the ethyl acetate (40 mL) solution of the compound 17 (5.00 g, 8.17 mmol) obtained in Example 2-3 were added 2-cyanoethyl N,N,N',N'-tetraisopropyl phosphorodiamidite (2.96 g, 9.82 mmol) and trifluoroacetic acid/pyridine salt (1.74 g, 9.01 mmol), followed by stirring at 20 to 30° C. for 24 hours. To the solution obtained was added 20% saline (17.5 mL) for liquid separation, and then to the organic layer obtained were added a 5% aqueous sodium bicarbonate solution (12.5 mL) and 20% saline (10 mL) for liquid separation. The organic layer obtained was cooled to 0 to 5° C., and a 10% aqueous potassium dihydrogen phosphate solution (20 mL) was added thereto for liquid separation. To the organic layer obtained were added a 5% aqueous sodium bicarbonate solution (12.5 mL) and 20% saline (10 mL) for liquid separation, and to the organic layer obtained was added 20% saline (17.5 mL) for liquid separation. The organic layer obtained was concentrated under reduced pressure and dissolved in ethyl acetate (15 mL). To this solution were added ethyl acetate (25 mL) and basic alumina (10.00 g), followed by stirring at 20 to 30° C. for 2 hours. Alumina was filtered out from the reaction mixture and washed with ethyl acetate (25 mL). Thereafter, the solution obtained by mixing the filtrate and the washing solution was concentrated under reduced pressure, the concentrate was dissolved in ethyl acetate (15 mL), and the ethyl acetate solution obtained was added dropwise to a mixed solution of n-heptane (45 mL) and diisopropyl ether (80 mL) at 20 to 30° C. over 35 minutes. Thereafter, n-heptane (90 mL) was added thereto, followed by stirring for 30 minutes at the same temperature. The solid precipitated was collected by filtration, and the solid obtained was washed with n-heptane (25 mL) and dried under reduced pressure (at 40° C. for 12 hours and then at 50° C. for 8 hours), to obtain a title compound 1t (5.18 g, 6.58 mmol, 80.6%).

The NMR spectrum of the compound obtained was consistent with the NMR spectrum of the compound according to Example 9 of International Publication No. WO 00/47599.

(Example 3) Production of 1-(2,6-anhydro-4-{[bis (4-methoxyphenyl) (phenyl)methoxy]methyl}-3-O-{ (2-cyanoethoxy) [di(propane-2-yl)amino]phosphanyl}-5-deoxy-a-L-lyxo-hexofuranosyl)-4-benzamide-5-methylpyrimidin-2 (1H)-one (Compound 1c)

(Example 3-1) Production of 1-{2,6-anhydro-3-O-benzyl-4-[(benzyloxy)methyl]-5-deoxy-a-L-lyxo-hexofuranosyl}-4-benzamide-5-methylpyrimidin-2 (1H)-one (Compound 3c)

[Formula 97]

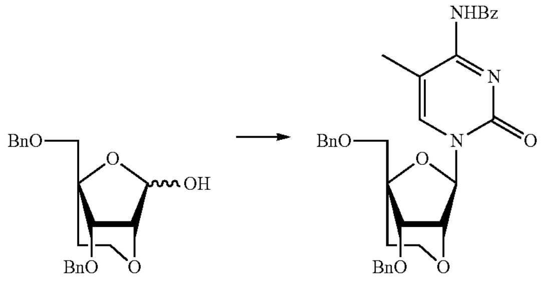

2 3c

To acetonitrile (25 mL) were added $N^4$-benzoyl-5-methylcytosine (8.04 g, 35.08 mmol) and N,O-bistrimethylsilylacetamide (14.27 g, 70.16 mmol), followed by stirring at 20 to 30° C. for 1 hour, to give a solution A. To acetonitrile (50 mL) in another reaction container were added the compound 2 (10.00 g, 28.06 mmol) obtained in Example 1 and trichloroacetonitrile (6.08 g, 42.09 mmol), and 1,8-diazabicyclo [5.4.0]undec-7-ene (0.41 g, 2.81 mmol) was added thereto, followed by stirring at 20 to 30° C. for 1 hour, to give a solution B. The solution A was added to the solution B, and then iodotrimethylsilane (7.02 g, 35.08 mmol) was added thereto, followed by stirring at 5 to 15° C. for 16 hours. To the reaction solution was added an aqueous solution obtained by dissolving sodium sulfite (8.84 g, 87.73 mmol) in a 5% aqueous sodium bicarbonate solution (80 mL) dropwise thereto, then toluene (100 mL) was added thereto for liquid separation, and a small amount of solid was filtered out. The organic layer obtained was washed with 50% methanol water (50 mL) twice. The organic layer obtained was concentrated under reduced pressure, to give a methanol solution (50 mL), followed by stirring at 20 to 30° C. for 16 hours, and then the solid precipitated was filtered and washed with methanol (50 mL). The solid obtained was dried under reduced pressure (40° C.), to obtain a compound 3c (9.35 g, 58.7%).

The NMR spectrum of the compound obtained was consistent with the NMR spectrum of the compound according to Example 19 of International Publication No. WO 00/47599.

(Example 3-2) Production of 1-[2,6-anhydro-5-deoxy-4-(hydroxymethyl)-α-L-lyxo-hexofuranosyl]-4-benzamide-5-methylpyrimidin-2 (1H)-one (Compound 18)

[Formula 98]

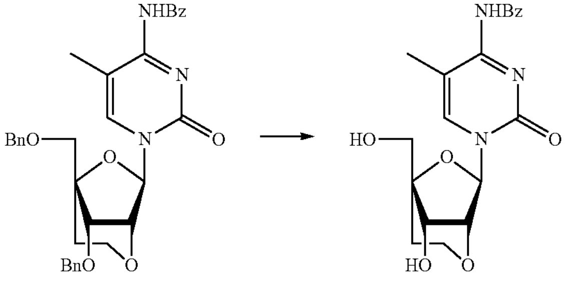

3c 18

To methylene chloride (20 mL) was added the compound 3c (5.00 g, 8.81 mmol) obtained in Example 3-1, and a 1M boron trichloride/methylene chloride solution (40.0 mL, 39.65 mmol) was added dropwise thereto at −20 to −10° C., followed by stirring for 16 hours. To the reaction solution was added a 50% Rochelle salt solution (20.0 mL) dropwise, and ethyl acetate (20 mL) and water (20 mL) were added thereto, followed by stirring at 20 to 30° C. for 16 hours. Thereafter, the solid precipitated was filtered and washed with water (20 mL) and ethyl acetate (20 mL). The solid obtained was dried under reduced pressure (40° C.), to obtain a compound 18 (1.59 g, 46.6%).

The NMR spectrum of the compound obtained was consistent with the NMR spectrum of the compound according to Example 11 of International Publication No. WO 00/47599.

(Example 3-3) Production of 1-(2,6-anhydro-4-{[bis (4-methoxyphenyl) (phenyl)methoxy]methyl}-5-deoxy-α-L-lyxo-hexofuranosyl)-4-benzamide-5-methylpyrimidin-2 (1H)-one (Compound 19)

[Formula 99]

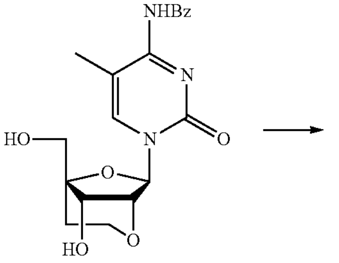

18

-continued

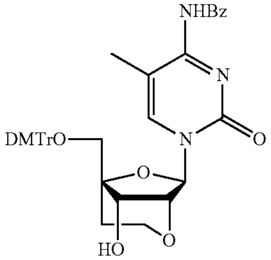

19

To ethyl acetate (40 mL) was added the compound 18 (1.00 g, 2.581 mmol) obtained in Example 3-2, followed by concentration under reduced pressure to 10 mL.

Thereafter, pyridine (0.815 g, 10.324 mmol) was added thereto, and 4,4'-dimethoxytrityl chloride (1.05 g, 3.098 mmol) was added thereto, followed by stirring at 20 to 30° C. for 16 hours. To the reaction solution, methanol (1.0 mL) was added, and then water (10 mL) and methanol (10 mL) were added thereto, followed by stirring at 20 to 30° C. for 16 hours. Thereafter, the solid precipitated was filtered and washed with water (5 mL) and ethyl acetate (5 mL). The solid obtained was dried under reduced pressure (40° C.), to obtain hydrated crystals of a compound 19 (1.53 g, 86.0%).

The NMR spectrum of the compound obtained was consistent with the NMR spectrum of the compound according to Example 21 of International Publication No. WO 00/47599.

(Example 3-4) Production of Compound 1c

[Formula 100]

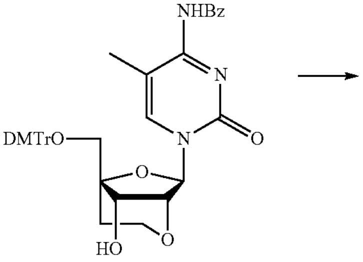

19

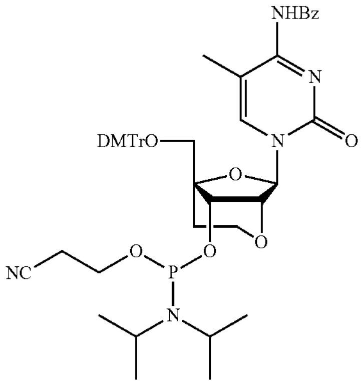

1c

To the hydrate (3.00 g, 4.24 mmol) of the compound 19 obtained in Example 3-3 was added dichloromethane (30 mL), followed by concentration under reduced pressure, to give a dichloromethane solution (9 mL). The operation of adding dichloromethane (30 mL) to the solution obtained, followed by concentration under reduced pressure, to give dichloromethane solution (9 mL) was repeated twice. To the solution obtained were added dichloromethane (15 mL), N,N,N',N'-tetraisopropyl phosphorodiamidite (1.54 g, 5.11 mmol), and trifluoroacetic acid/pyridine salt (0.902 g, 4.67 mmol), followed by stirring at 20 to 30° C. for 7 hours. The solution obtained was washed with a 5% aqueous sodium bicarbonate solution (10.5 mL) twice and then with 5% saline (12 mL) twice, followed by concentration under reduced pressure, to obtain a dichloromethane solution (9 mL). To the solution obtained were added dichloromethane (15 mL) and basic alumina (6.00 g), followed by stirring at 20 to 30° C. for 30 minutes. Alumina was filtered out and washed with dichloromethane (15 mL), and then the solution obtained was concentrated under reduced pressure, to obtain a dichloromethane solution (9 mL) of the compound 1c. The solution obtained was added dropwise to a mixed solution of n-heptane (66 mL) and diisopropyl ether (15.6 mL) at 20 to 30° C. over 35 minutes. After stirring at the same temperature for 2 hours, the solid precipitated was filtered and washed with n-heptane (15 mL). The solid obtained was dried under reduced pressure (40° C.), to obtain a compound 1c (3.33 g, 3.74 mmol, 88.3%).

The NMR spectrum of the compound obtained was consistent with the NMR spectrum of the compound according to Example 6 of International Publication No. WO 00/47599.

(Example 4) Production of 9-(2,6-anhydro-4-{[bis (4-methoxyphenyl) (phenyl)methoxy]methyl}-3-O-{(2-cyanoethoxy) [di(propane-2-yl)amino]phosphanyl}-5-deoxy-a-L-lyxo-hexofuranosyl)-N-benzoyl-9H-purin-6-amine (Compound 1a)

(Example 4-1-1) Production of 9-{2,6-anhydro-3-O-benzyl-4-[(benzyloxy)methyl]-5-deoxy-α-L-lyxo-hexofuranosyl}-N-benzoyl-9H-purin-6-amine (Compound 3a)

[Formula 101]

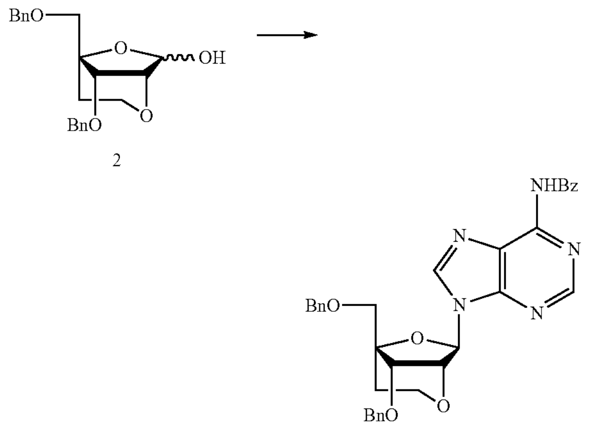

2

3a

To trifluoromethanesulfonic acid (7.44 mL, 84.18 mmol) was added dichlorodimethylsilane (5.44 g, 42.09 mmol), followed by stirring at 20 to 30° C. for 0.5 hours, and then acetonitrile (80 mL) and N-benzoyl adenine (10.06 g, 42.09 mmol) were added thereto, followed by stirring at 20 to 30° C. for 3 hours, to give a solution A. To acetonitrile (40 mL) in another reaction container were added the compound 2 (10.00 g, 28.06 mmol) obtained in Example 1 and trichloroacetonitrile (4.2 mL, 42.09 mmol), and 1,8-diazabicyclo [5.4.0]undec-7-ene (0.22 g, 1.40 mmol) was added thereto, followed by stirring at 20 to 30° C. for 1 hour, to give a solution B. To the solution A was added the solution B, followed by stirring at 45 to 55° C. for 2 hours. The temperature was adjusted to 0 to 10° C., and then to the reaction solution were added toluene (100 mL) and a 20% aqueous potassium bicarbonate solution (70 mL) for liquid separation, to obtain a toluene layer. To the toluene layer obtained was added a 20% aqueous citric acid solution (50 mL) for liquid separation, to obtain a toluene layer. To the toluene layer obtained by repeating the same operation of liquid separation twice were added water (30 mL) and a 20% aqueous potassium bicarbonate solution (25 mL) for liquid separation, to obtain a toluene layer. To the toluene layer obtained was added a 50% aqueous methanol solution (100 mL) for liquid separation, to obtain a toluene layer. The toluene layer obtained was concentrated under reduced pressure, to give a toluene solution (80 mL). To the solution obtained was added isobutyl alcohol (100 mL), followed by concentration under reduced pressure, to obtain a toluene-isobutyl alcohol solution (100 mL). To the solution obtained was added isobutyl alcohol (50 mL), followed by concentration under reduced pressure, to obtain a toluene-isobutyl alcohol solution (50 mL). To the solution obtained was added isobutyl alcohol (50 mL), followed by stirring at 20 to 30° C. for 2 hours, to confirm precipitation of crystals. The temperature was adjusted to 0 to 10° C. over 0.5 hours, followed by stirring for 1 hour, and then the crystals precipitated were filtered, washed with isobutyl alcohol (50 mL) cooled to 0° C. in advance, and dried under reduced pressure (40° C.), to obtain a compound 3a (7.82 g, 13.54 mmol, yield 48.3%).

The NMR spectrum of the compound obtained was consistent with the NMR spectrum of the compound according to Example 6 of International Publication No. WO 00/47599.

(Example 4-1-2) Production of 1-O-acetyl-2,6-anhydro-3-O-benzyl-4-[(benzyloxy)methyl]-5-deoxy-a-L-glycero-hexofuranose (Compound 22)

[Formula 102]

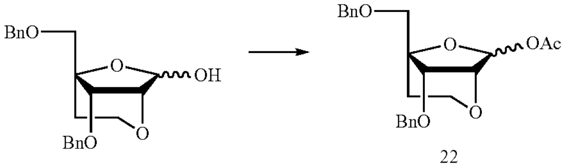

2

22

Toluene (1497 mL), the compound 2 (149.73 g, 375.78 mmol) obtained in Example 1, acetic anhydride (64.33 g, 563.67 mmol), pyridine (49.85 g, 563.67 mmol), and 4-dimethylaminopyridine (2.57 g, 18.79 mmol) were added, followed by stirring at 20 to 30° C. for 2 hours, and then to the reaction solution was added water (749 mL) for liquid separation, to obtain a toluene layer. To the toluene layer obtained was added a 20% aqueous citric acid solution (749 mL) for liquid separation, to obtain a toluene layer. To the toluene layer obtained by repeating the same liquid separation again was added an 8% aqueous potassium bicarbonate solution (449 mL) for liquid separation, to obtain a toluene layer. To the toluene layer obtained was added 5% saline (449 mL) for liquid separation, to obtain a toluene layer. The toluene layer obtained was concentrated under reduced pressure, to give a toluene solution (449 mL). To the solution obtained was added acetonitrile (1497 mL), followed by concentration under reduced pressure, to obtain a toluene-acetonitrile solution (449 mL). To the solution obtained was added acetonitrile (1497 mL), followed by concentration under reduced pressure, to obtain a toluene-acetonitrile solution (449 mL) of a compound 22.

(Example 4-1-3a) Production of 9-{2,6-anhydro-3-O-benzyl-4-[(benzyloxy)methyl]-5-deoxy-α-L-lyxo-hexofuranosyl}-N-benzoyl-9H-purin-6-amine (Compound 3a)

[Formula 103]

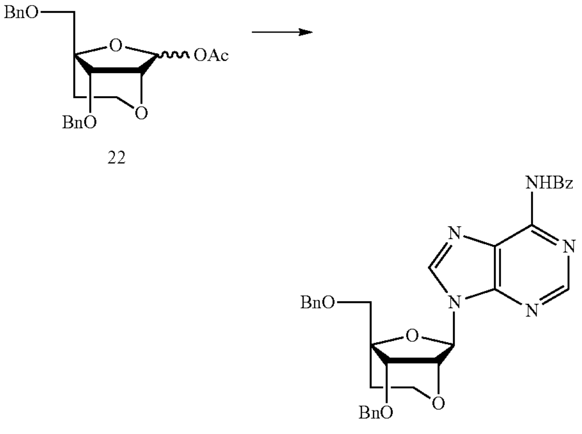

22

3a

Acetonitrile (51 mL), N-benzoyl adenine (5.09 g, 21.30 mmol), and trimethylsilyl trifluoromethanesulfonate (9.78 g, 44.01 mmol) were added, followed by stirring at 20 to 30° C. for 40 minutes. A toluene-acetonitrile solution (11.65 g, 14.20 mmol) containing the compound 22 obtained in Example 4-1-2 was added thereto, followed by stirring at 20 to 30° C. for 16 hours. Subsequently, trifluoroacetic acid (2.43 g, 21.30 mmol) was added, followed by stirring at 20 to 30° C. for 1 hour, and then the temperature was raised to 45 to 55° C., followed by stirring for 3 hours. The temperature was adjusted to 20 to 30° C., and then to the reaction solution were added toluene (51 mL), 25% sodium hydroxide (10 mL), and an 8% aqueous sodium bicarbonate solution (10 mL), followed by stirring at 20 to 30° C. for 1 hour. Subsequently, a 10% aqueous trifluoroacetic acid solution (25 mL) was added thereto for liquid separation, to obtain a toluene layer. To the toluene layer obtained by repeating the same liquid separation 3 times was added an 8% aqueous sodium bicarbonate solution (51 mL) for liquid separation, to obtain a toluene layer. To the toluene layer obtained were added a 50% aqueous methanol solution (20 mL) and 20% saline (5 mL) for liquid separation, to obtain a toluene layer. The toluene layer obtained by repeating the same liquid separation once was concentrated under reduced pressure, to give a toluene solution (15 mL). To the solution obtained was added isobutyl alcohol (40 mL), followed by concentration under reduced pressure, to obtain a toluene-isobutyl alcohol solution (40 mL). To the solution obtained was added isobutyl alcohol (15 mL), and crystals of the compound 3a (0.1 wt %) were added, followed by stirring at 35 to 45° C. for 30 minutes, to confirm precipitation of crystals. Subsequently, a toluene-isobutyl alcohol solution (40 mL) was obtained by concentration under reduced pressure, then isobutyl alcohol (5 mL) was added thereto, and the temperature was adjusted to 0 to 10° C. over 2 hours, followed by stirring for 17.5 hours. The crystals precipitated were filtered, washed with isobutyl alcohol (25 mL) cooled to 0° C. in advance, and dried under reduced pressure (40° C.), to obtain the compound 3a (6.37 g, 11.03 mmol, yield 77.7%).

(Example 4-1-3b) Production of 9-{2,6-anhydro-3-O-benzyl-4-[(benzyloxy)methyl]-5-deoxy-α-L-lyxo-hexofuranosyl}-N-benzoyl-9H-purin-6-amine (Compound 3a)

To acetonitrile (30 mL) were added N-benzoyl adenine (3.02 g, 12.63 mmol) and trimethylsilyl trifluoromethanesulfonate (5.61 g, 25.25 mmol), and the reaction mixture was stirred at 20 to 30° C. for 30 minutes. To the reaction mixture obtained were added an acetonitrile solution (6 mL) containing the compound 22 obtained in Example 4-1-2 and acetonitrile (3 mL), and the reaction mixture was stirred at 20 to 30° C. for 2 hours. Subsequently, trifluoroacetic acid (1.44 g, 12.63 mmol) was added thereto, and the reaction mixture was stirred at 35 to 45° C. for 6 hours. The reaction mixture obtained was cooled to 0° C., and then the pH of the reaction solution was adjusted to 6.5 to 7.5 using 25% sodium hydroxide (3 mL). Thereafter, to the reaction mixture was added water (9 mL) at 20 to 30° C., crystals of the compound 3a (0.1 wt %) were added, and the reaction mixture was stirred at 20 to 30° C. for 19 hours. Thereafter, water (27 mL) was further added thereto, followed by stirring at 20 to 30° C. for 4 hours. The crystals precipitated were filtered, washed with 50% acetonitrile water (15 mL), and dried under reduced pressure (40° C.), to obtain the compound 3a (3.59 g, 6.21 mmol, yield 73.8%).

The NMR spectrum of the compound obtained was consistent with the NMR spectrum of the compound according to Example 6 of International Publication No. WO 00/47599.

(Example 4-2) Production of 9-[2,6-anhydro-5-deoxy-4-(hydroxymethyl)-α-L-lyxo-hexofuranosyl]-N-benzoyl-9H-purin-6-amine (Compound 20)

[Formula 104]

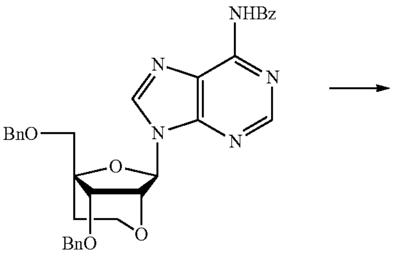

3a

-continued

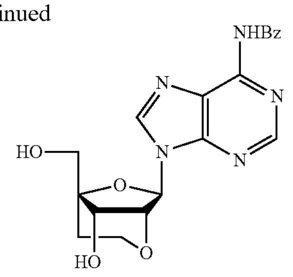

20

-continued

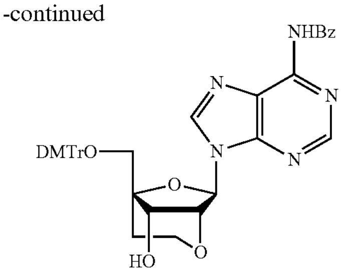

21

To a 1M boron trichloride/methylene chloride solution (50.0 mL, 51.94 mmol) was added the compound 3a (2.00 g, 3.46 mmol) obtained in Example 4-1-3 at −20 to −10° C., followed by stirring for 0.5 hours. Completion of the reaction was confirmed, and a methylene chloride solution (20 mL) was obtained by concentration under reduced pressure.

To the solution obtained was added a 50% aqueous potassium hydroxide solution (6.0 mL) dropwise, and n-heptane (6 mL) was added thereto, followed by stirring at 20 to 30° C. for 15 minutes. Thereafter, the solid precipitated was filtered and washed with methylene chloride/n-heptane (5/1.4 mL). To the solid obtained were added acetonitrile (30 mL) and water (4 mL). After stirring for 0.5 hours, the solid was filtered and washed with acetonitrile (4 mL). To the solid obtained was added methanol (30 mL), and then the solid was filtered out and washed with methanol (10 mL), to obtain a methanol solution. The solution obtained was adjusted by concentrating under reduced pressure to a methanol solution (10 mL). To the solution obtained was added acetonitrile (20 mL), followed by concentration under reduced pressure, to obtain an acetonitrile-methanol mixed solution (10 mL). To the acetonitrile-methanol mixed solution (10 mL) obtained by repeating the same concentration under reduced pressure twice was added acetonitrile (10 mL), followed by stirring for 16 hours, and the solid was filtered and washed with acetonitrile (6 mL). The solid obtained was dried under reduced pressure (40° C.), to obtain a compound 20 (0.61 g, 44.3%).

The NMR spectrum of the compound obtained was consistent with the NMR spectrum of the compound according to Example 11 of International Publication No. WO 00/47599.

(Example 4-3) Production of 9-(2,6-anhydro-4-{[bis(4-methoxyphenyl) (phenyl)methoxy]methyl}-5-deoxy-α-L-lyxo-hexofuranosyl)-N-benzoyl-9H-purin-6-amine (Compound 21)

[Formula 105]

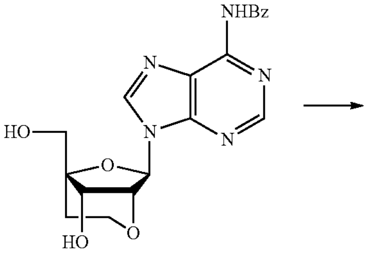

20

To tetrahydrofuran (7.5 mL) were added the compound 20 (0.50 g, 1.26 mmol) obtained in Example 4-2 and 4,4'-dimethoxytrityl chloride (0.64 g, 1.89 mmol), and pyridine (0.60 g, 7.55 mmol) was added thereto, followed by stirring at 50° C. for 2 hours. To the reaction solution were added toluene (5.0 mL) and water (2.5 mL) for liquid separation, to obtain a toluene layer. The toluene layer obtained was subjected to liquid separation with a 20% aqueous citric acid solution (2.5 mL) three times, and a 20% potassium carbonate aqueous solution (1.0 mL) was added thereto for liquid separation, to obtain a toluene layer. To the toluene layer obtained was added water (2.5 mL), followed by washing for liquid separation, to obtain a toluene solution (2.5 mL) by concentration under reduced pressure. To the solution obtained was added toluene (5.0 mL), followed by concentration under reduced pressure, to obtain a toluene solution (2.5 mL). A toluene solution (2.5 mL) was obtained by repeating the same operation twice. To the solution obtained were added toluene (2.5 mL) and water (50 μL), followed by stirring at 20 to 30° C. for 3 hours, and then the solid precipitated was filtered and washed with toluene (2.5 mL). The solid obtained was dried under reduced pressure (40° C.), to obtain a crude compound 21 (0.51 g, 58.0%).

To 2-propanol (1.8 mL) were added the crude compound 21 (0.36 g, 0.51 mmol) and water (1.8 mL), followed by stirring at 20 to 30° C. for 0.5 hours. Water (1.8 mL) was further added thereto, followed by stirring for 15 minutes, and then the solid was filtered and washed with 2-propanol-water (1/3, 1.8 mL). The solid obtained was dried under reduced pressure (40° C.), to obtain a hydrate of a compound 21 (0.31 g, 86.1%).

The NMR spectrum of the compound obtained was consistent with the NMR spectrum of the compound according to Example 13 of International Publication No. WO 00/47599.

(Example 4-4) Production of Compound 1a

[Formula 106]

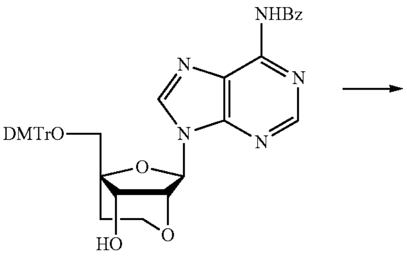

21

-continued

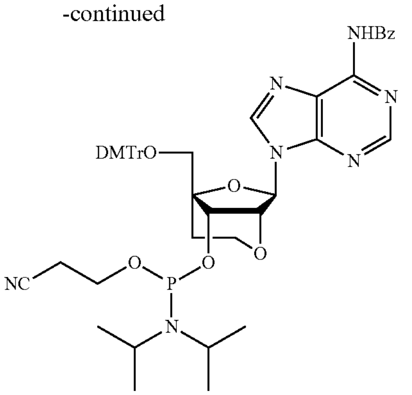

1a

To the hydrate (150 mg, 0.209 mmol) of the compound 21 obtained in Example 4-3 was added dichloromethane (1.5 mL), followed by concentration under reduced pressure and evaporation to dryness. To the foam obtained was added dichloromethane (1.5 mL), followed by concentration under reduced pressure and evaporation to dryness, and dichloromethane (1.2 mL), N,N,N',N'-tetraisopropyl phosphorodiamidite (77.9 mg, 0.258 mmol), and trifluoroacetic acid/pyridine salt (44.4 mg, 0.230 mmol) were added thereto, followed by stirring at 20 to 30° C. for 4 hours. The solution obtained was washed with a 5% aqueous sodium bicarbonate solution (0.525 mL) twice and then with 5% saline (0.600 mL) twice, followed by concentration under reduced pressure and evaporation to dryness. To the foam obtained were added ethyl acetate (1.2 mL) and neutral silica gel (300 mg), followed by stirring at 20 to 30° C. for 1 hour. The silica gel was filtered out and washed with ethyl acetate (6 mL), and then the solution obtained was concentrated under reduced pressure and evaporated to dryness. An ethyl acetate (0.600 mL) solution of the foam obtained was added dropwise to a mixed solution of n-heptane (1.35 mL) and diisopropyl ether (2.4 mL) at 20 to 30° C. over 20 minutes. Further, n-heptane (3.15 mL) was added thereto, followed by stirring at the same temperature for 1 hour, and then the solid precipitated was filtered and washed with n-heptane (6 mL). The solid obtained was dried under reduced pressure (40° C.), to obtain a compound 1a (132.5 mg, 0.147 mmol, 70.4%).

The NMR spectrum of the compound obtained was consistent with the NMR spectrum of the compound according to Example 14 of International Publication No. WO 00/47599.

(Example 5) Production of Compound 20

(Example 5-1) Purification of Compound 22

A crude mixture (6.57 g) of the compound 22 obtained by concentrating and drying the solution obtained in Example 4-1-2 was purified by silica-gel column chromatography (hexane:ethyl acetate=94:6 to 50:50), to obtain a β-product (4.68 g) of the compound 22.

$^1$H NMR (β-form, $CDCl_3$): δ=1.43 (1H, dd, J=3.5, 13.5 Hz), 2.01 (3H, s), 2.17-2.24 (1H, m), 3.57 (2H, dd, J=11.5, 22.0 Hz),3.94-3.97 (2H, m), 4.07 (1H, d, J=3.0 Hz), 4.14 (1H, d, J=3.0 Hz), 4.54 (1H, d, J=12.5 Hz), 4.61 (2H, dd, J=12.5, 18.0 Hz), 4.74 (1H, d, J=11.5 Hz), 6.33 (1H, s), 7.26-7.37 (10H, m).

(Example 5-2) Production of 9-{2,6-anhydro-3-O-benzyl-4-[(benzyloxy)methyl]-5-deoxy-a-L-lyxo-hexofuranosyl}-2,6-dichloro-9H-purine (Compound 23)

[Formula 107]

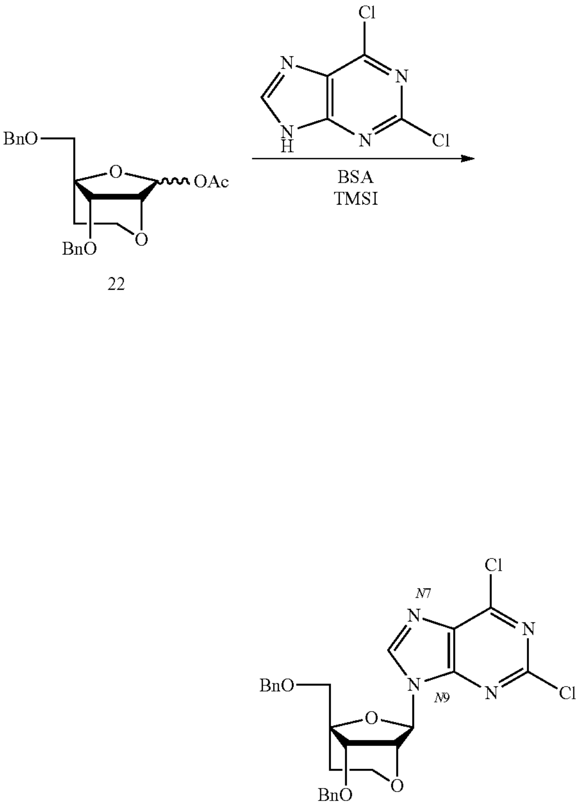

22

23

To the toluene solution (0.6 mL) of the compound 22 (60.0 mg, 150.58 μmol) obtained in Example 5-1-2 were added N,O-bistrimethylsilylacetamide (40.5 μL, 165.64 μmol) and 2,6-dichloropurine (31.3 mg, 165.64 μmol), followed by stirring at 75° C. for 1 hour, and iodotrimethylsilane (22.5 μL, 165.64 μmol) was added thereto, followed by stirring for 3 hours. Completion of the reaction was confirmed, followed by cooling to room temperature, and ethyl acetate (18.0 mL) and 5% aqueous sodium bicarbonate (3.0 mL) were added thereto for liquid separation. The organic layer obtained was concentrated and dried, and then the residue was purified by silica gel chromatography (hexane:ethyl acetate=2:1), followed by concentration under reduced pressure, to obtain a compound 23 as a colorless oily compound (52.0 mg, 65.4%).

$^1$H-NMR ($CDCl_3$): δ=8.79 (1H, s), 7.23-7.39 (10H, m), 6.43 (1H, s), 4.57-4.65 (2H, m), 4.42-4.45 (1H, m), 4.15 (1H, d, J=3.0 Hz), 4.06-4.09 (2H, m), 3.71 (1H, d, J=10.5 Hz), 3.56 (1H, d, J=10.5 Hz), 2.27-2.36 (2H, m), 1.41-1.44 (2H, m)

(Example 5-3) Production of 9-{2,6-anhydro-3-O-benzyl-4-[(benzyloxy)methyl]-5-deoxy-a-L-lyxo-hexofuranosyl}-2-chloro-9H-purin-6-amine (Compound 24)

[Formula 108]

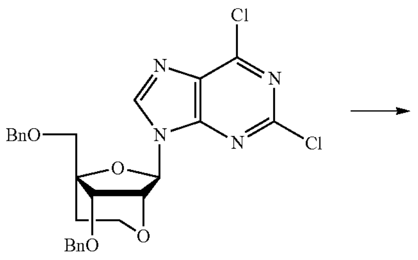

23

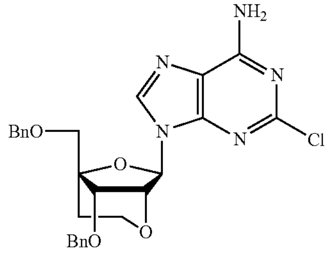

24

To a tetrahydrofuran solution (0.75 mL) of the compound 23 (52.0 mg, 98.60 μmol) obtained in Example 5-2 was added a 28% aqueous ammonia solution (0.5 mL), followed by stirring at 50° C. for 7 hours. Completion of the reaction was confirmed, followed by cooling to room temperature, and ethyl acetate (2.0 mL) was added thereto for liquid separation. The organic layer obtained was washed with 20% saline (1.0 mL), then concentrated, and dried. The residue was purified by silica gel chromatography (hexane: ethyl acetate=4:6), followed by concentration under reduced pressure, to obtain the compound 24 as white crystals (44.7 mg, 89.2%).

$^1$H-NMR ($CDCl_3$): δ=8.36 (1H, s), 7.27-7.38 (10H, m), 6.39 (1H, s), 5.69 (2H, brs), 4.56-4.68 (2H, m), 4.44-4.48 (1H, m), 4.20 (1H, d, J=2.5 Hz), 4.05-4.14 (2H, m), 3.70 (1H, d, J=10.8 Hz), 3.57 (1H, d, J=10.8 Hz), 2.28-2.36 (1H, m), 1.53 (1H, m), 1.42-1.44 (1H, m), 1.25-1.27 (1H, m)

(Example 5-4) Production of 9-{2,6-anhydro-3-O-benzyl-4-[(benzyloxy)methyl]-5-deoxy-a-L-lyxo-hexofuranosyl}-9H-purin-6-amine (Compound 25)

[Formula 109]

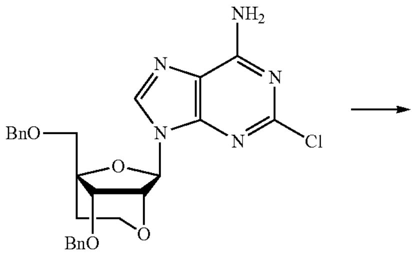

24

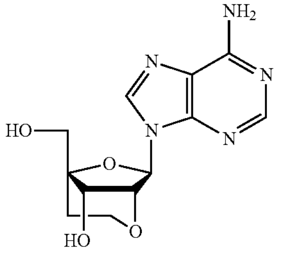

25

To an ethanol solution (2.0 mL) of the compound 24 (26.2 mg, 51.58 μmol) obtained in Example 5-3 were added 20% palladium hydroxide on carbon (20.0 mg), and a 1 N aqueous sodium hydroxide solution (103.2 μL, 103.16 μmol), followed by stirring at 50° C. for 5 hours under a hydrogen pressure of 3.5 bar. After the reaction, the mixture was cooled to room temperature, and a 1 N aqueous hydrochloric acid solution (51.6 μL, 51.58 μmol) was added thereto, followed by filtration. To the filtrate was added ethanol (10 mL), followed by concentration and drying, to obtain a compound 25 as white crystals (9.7 mg, 64.1%).

$^1$H-NMR ($CD_3OD$): =8.72 (1H, s), 8.35 (1H, s), 6.48 (1H, s), 4.37 (1H, d, J=3.5 Hz), 4.32 (1H, d, J=3.0 Hz), 4.01-4.13 (2H, m), 3.78 (1H, d, J=12.5 Hz), 3.72 (1H, d, J=12.0 Hz), 2.17-2.24 (1H, m), 1.44(1H, dd, J=13.0 Hz, 4.0 Hz)

(Example 5-5) Production of Compound 20

[Formula 110]

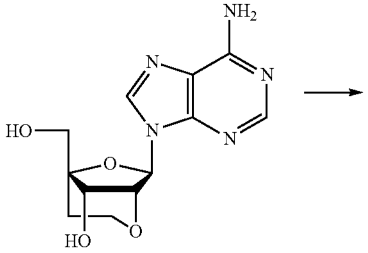

25

-continued

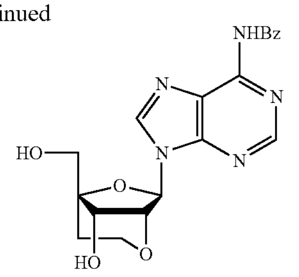

20

To a pyridine solution (30 v/w) of the compound 25 obtained in Example 5-4 was added chlorotrimethylsilane (5 equivalent), followed by stirring for 30 minutes, and benzoyl chloride (5 equivalent) was added thereto, to allow the reaction to proceed at room temperature for 2 hours. After the reaction, the resultant was cooled to 0° C., and ammonia water was added, to give a 2 M ammonia solution. After 30 minutes, the solution was concentrated under reduced pressure, acetonitrile (30 v/w) was added thereto for concentration to (3 v/w), and the crystals precipitated were collected by filtration, to obtain the compound 20.

(Example 6) Production of 9-(2,6-anhydro-4-{[bis (4-methoxyphenyl) (phenyl)methoxy]methyl}-3-O-{(2-cyanoethoxy) [di(propane-2-yl)amino]phosphanyl}-5-deoxy-a-L-lyxo-hexofuranosyl)-2-(2-methylpropane amide)-1,9-dihydro-6H-purin-6-one (Compound 1g)

(Example 6-1) Production of 9-{2,6-anhydro-3-O-benzyl-4-[(benzyloxy)methyl]-5-deoxy-a-L-lyxo-hexofuranosyl}-6-(benzyloxy)-2-chloro-9H-purine (Compound 26)

[Formula 111]

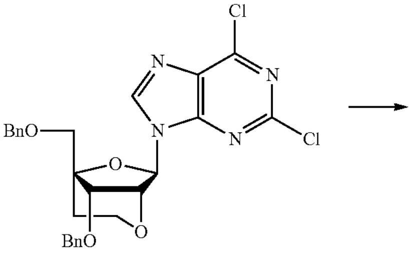

23

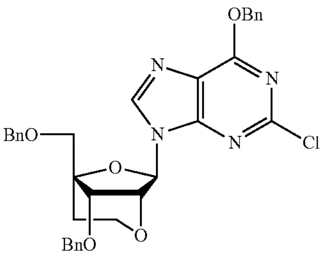

26

To tetrahydrofuran (0.5 mL) were added benzyl alcohol (4.63 μL, 66.84 μmol) and sodium hydride (2.5 mg, 57.93 μmol), followed by stirring at 0° C. for 30 minutes, and the compound 23 (23.5 mg, 44.56 μmol) obtained in Example 5-2 was added thereto, followed by stirring for 3 hours. Completion of the reaction was confirmed, and then acetic acid (3.6 μL, 62.38 μmol), 20% saline (0.5 mL), and ethyl acetate (2.0 mL) were added thereto for liquid separation. The organic layer obtained was concentrated and dried, and then the residue was purified by silica gel chromatography (hexane:ethyl acetate=2:1), followed by concentration under reduced pressure, to obtain a compound 26 as a colorless oily compound (20.9 mg, 78.3%).

$^1$H-NMR ($CD_3Cl$): 6=8.50 (1H, s), 7.55-7.60 (2H, m), 7.24-7.40 (13H, m), 6.42 (1H, s), 5.68 (1H, d, J=12.0 Hz), 5.63 (1H, d, J=11.5 Hz), 4.55-4.64 (3H, m), 4.43-4.44 (2H, m), 4.17 (1H, d, J=2.5 Hz), 4.06-4.08 (2H, m), 3.69 (1H, d, J=10.0 Hz), 3.55 (1H, d, J=10.5 Hz), 2.26-2.32 (1H, m), 1.41-1.44 (1H, m)

(Example 6-2) Production of 9-{2,6-anhydro-3-O-benzyl-4-[(benzyloxy)methyl]-5-deoxy-a-L-lyxo-hexofuranosyl}-6-(benzyloxy)-N-(2-methylpropanoyl)-9H-purin-2-amine (Compound 27)

[Formula 112]

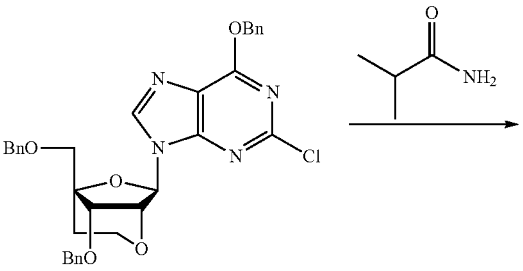

26

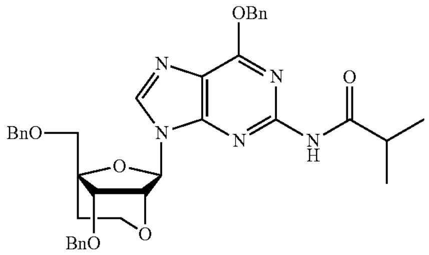

27

The compound 26 (34.9 mg, 58.26 μmol) obtained in Example 6-1, isobutyl amide (7.6 mg, 87.39 μmol), tris (dibenzylideneacetone) (chloroform)dipalladium (3.0 mg, 2.91 μmol), 4,5'-bis(diphenylphosphino)-9,9'-dimethylxanthene (3.4 mg, 5.83 μmol), and cesium carbonate (36.1 mg, 110.69 μmol) were added to the reaction container, and then toluene (0.7 mL), degassed under a nitrogen atmosphere, was added thereto. The reaction solution was heated to 110° C., followed by stirring for 12 hours, and then tap water (1.0 mL) and ethyl acetate (4.0 mL) were added thereto for liquid separation. The organic layer obtained was concentrated and dried, and then the residue was purified by silica gel chromatography (hexane:ethyl acetate=1:1), followed by concentration under reduced pressure, to obtain a compound 27 as a colorless oily compound (18.1 mg, 47.8%).

$^1$H-NMR ($CD_3Cl$): =8.37 (1H, s), 7.83 (1H, brs), 7.53-7.55 (2H, m), 7.24-7.39 (13H, m), 6.35 (1H, s), 5.67 (1H, d, J=12.0 Hz), 5.62 (1H, d, J=12.0 Hz), 4.56-4.64 (3H, m), 4.43-4.45 (2H, m), 4.18 (1H, d, J=2.5 Hz), 4.07-4.12 (2H, m), 3.70 (1H, d, J=11.0 Hz), 3.56 (1H, d, J=10.5 Hz), 3.22 (1H, brs), 2.27-2.23 (1H, m), 1.43-1.46 (1H, m), 1.28 (6H, dd, J=6.8 Hz, 2.3 Hz)

(Example 6-3) Production of 9-[2,6-anhydro-5-deoxy-4-(hydroxymethyl)-α-L-lyxo-hexofuranosyl]-2-(2-methylpropane amide)-1,9-dihydro-6H-purin-6-one (compound 28)

[Formula 113]

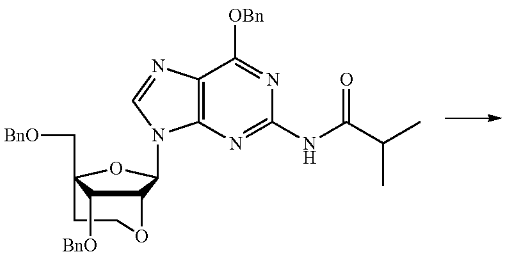

27

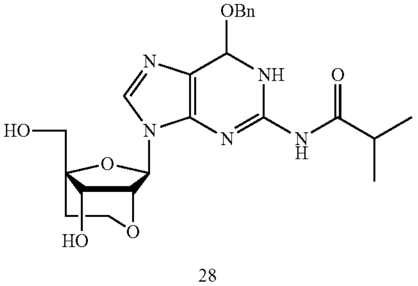

28

To an ethanol solution (2.0 mL) of the compound 27 (17.7 mg, 27.24 μmol) obtained in Example 6-2 were added 20% palladium hydroxide on carbon (18.0 mg), followed by stirring at 45° C. for 3 hours under a hydrogen pressure of 3.5 bar. Completion of the reaction was confirmed, followed by cooling to room temperature and filtration. The filtrate was concentrated and dried, to obtain a compound 28 as white crystals (11.7 mg, 101.0%).

$^1$H-NMR (DMSO-$d_6$): δ=12.10 (1H, s), 11.79 (1H, s), 8.31 (1H, s), 6.21 (1H, s), 5.39 (1H, brs), 5.25 (1H, brs), 4.14 (1H, d, J=3.5 Hz), 4.10 (1H, d, J=3.0 Hz), 3.88-3.90 (2H, m), 3.61 (1H, d, J=12.5 Hz), 2.75-2.81 (1H, m), 2.00-2.07 (1H, m), 1.12 (6H, d, J=6.5 Hz)

(Example 6-4) Production of 9-(2,6-anhydro-4-{[bis(4-methoxyphenyl) (phenyl)methoxy]methyl}-5-deoxy-α-L-lyxo-hexofuranosyl)-2-(2-methylpropane amide)-1,9-dihydro-6H-purin-6-one (Compound 29)

[Formula 114]

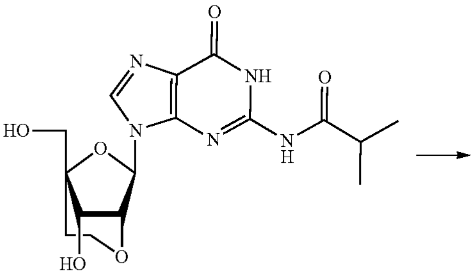

28

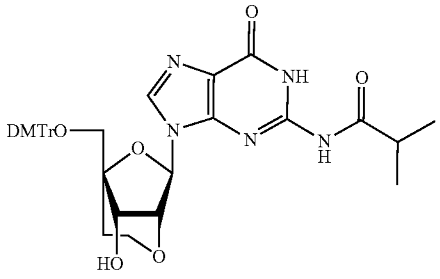

29

A tetrahydrofuran solution (5 v/w) of the compound 28 obtained in Example 6-3 was reacted with dimethoxytriphenylmethyl chloride (1.5 equivalent). To the reaction solution were added toluene (10 v/w) and water (5 v/w) for liquid separation, followed by concentration and purification by silica-gel column chromatography, to obtain a compound 29.

(Example 6-5) Production of Compound 1g

[Formula 115]

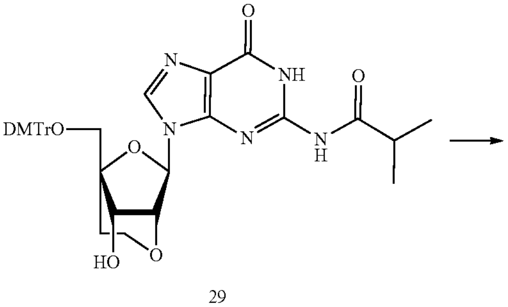

29

-continued

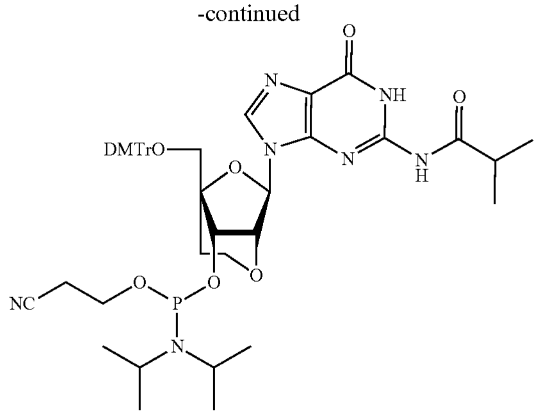

1g

To the compound 29 obtained in Example 6-4 were added dichloromethane (10 v/w), molecular sieve 4A (0.5 w/w), 2-cyanoethyl N,N,N',N'-tetraisopropyl phosphorodiamidite (1.5 equivalent), and 4,5-dicyanoimidazole (0.5 equivalent), followed by stirring at room temperature for 24 hours. To the reaction solution were added ethyl acetate (900 mL) and water (5 v/w) for liquid separation, followed by concentration and purification by silica-gel column chromatography, to obtain a compound 1g.

(Example 7) Production of Compound 17 (glycosylation via Compound 22)

(Example 7-1) Production of acetonitrile Solution of Compound 22

[Formula 116]

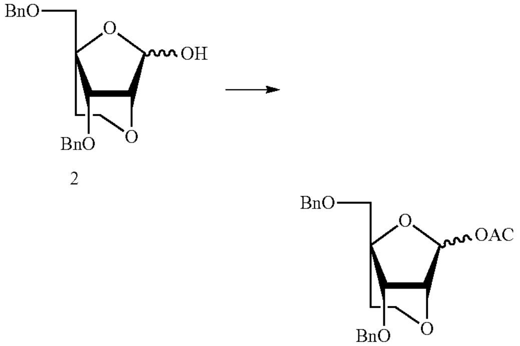

2

22

To a toluene (30 mL) solution of the compound 2 (3.00 g, 8.42 mmol) were added N,N-dimethylaminopyridine (0.05 g, 0.42 mmol), pyridine (1.02 mL, 12.63 mmol), and acetic anhydride (1.20 mL, 12.63 mmol), followed by stirring at 20 to 30° C. for 1 hour, and then water (15 mL) was added for liquid separation. The organic layer obtained was washed with a 20% aqueous citric acid solution (15 mL) twice and with 8% aqueous sodium bicarbonate solution (9 mL) and water (9 mL) once for liquid separation. The organic layer obtained was concentrated under reduced pressure to 6 mL, and then the solvent was substituted with acetonitrile (30 mL) by concentration under reduced pressure twice, to obtain an acetonitrile solution (6 mL) of the compound 22.

(Example 7-2) Production of 1-propanol Solution of Compound 3t

[Formula 117]

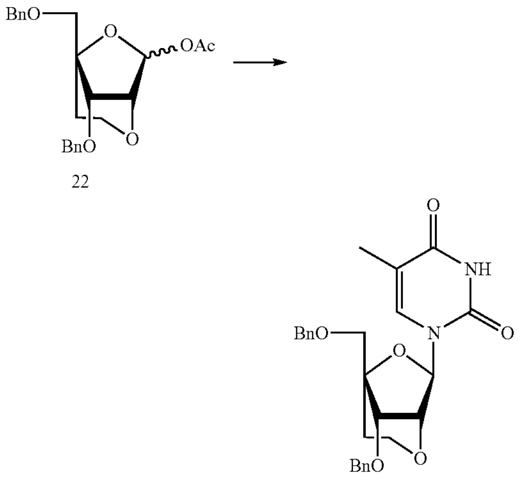

22

3t

To acetonitrile (7.5 mL) were added thymine (1.33 g, 10.52 mmol) and N,O-bistrimethylsilylacetamide (5.15 mL, 21.04 mmol), followed by stirring at 20 to 30° C. for 1 hour, and then to the solution obtained were added an acetonitrile solution (6 mL) of the compound 22 obtained in Example 7-1, acetonitrile (9 mL), and iodotrimethylsilane (1.50 mL, 10.52 mmol), followed by stirring at 45 to 55° C. for 4 hours. To the reaction solution were added an 8% aqueous sodium bicarbonate solution (24 mL) and sodium sulfite (1.20 g), and then toluene (30 mL) was added thereto, followed by stirring at 20 to 30° C. for 30 minutes and then liquid separation. The organic layer obtained was washed with 20% methanol water (18 mL) for liquid separation 3 times and then concentrated under reduced pressure to 9 mL. To the concentrated solution obtained was added 1-propanol (30 mL), followed by concentration under reduced pressure again, to obtain a 1-propanol solution (9 mL) of the compound 3t.

The NMR spectrum of the compound obtained was consistent with the NMR spectrum of the compound according to Example 6 of International Publication No. WO 00/47599.

(Example 7-3) Production of Compound 16

[Formula 118]

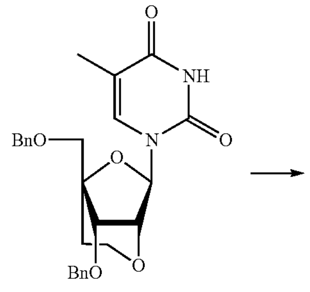

3t

-continued

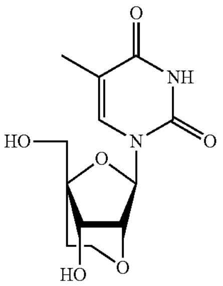

16

-continued

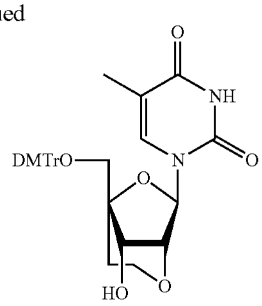

17

To the 1-propanol solution (9 mL) of the compound 3t were further added 1-propanol (15 mL), water (6 mL), and 5% palladium carbon (0.67 g), followed by stirring at 55 to 65° C. for 2 hours under a hydrogen atmosphere, and then the catalyst was filtered at the same temperature and washed with 80% 1-propanol water (6 mL). The filtrate obtained was concentrated under reduced pressure, to give a 1-propanol solution (9 mL), and then acetonitrile (30 mL) was added thereto, followed by concentration under reduced pressure, to give 9 mL of an acetonitrile solution (A). Acetonitrile (6 mL) was further added thereto, followed by stirring at 20 to 30° C. for 2 hours. The crystals generated were collected by filtration and washed with acetonitrile (9 mL). The solid obtained was dried under reduced pressure (40° C.), to obtain the compound 16 (1.57 g, yield 65.6% (from the compound 2)). In the case where the water content of the acetonitrile solution (A) was over 4% in the aforementioned procedure, the reproducibility of recovery by crystallization could be maintained by repeating the operation of adding acetonitrile for concentration to 9 mL so as to control the water content to 4% or less. The water content was confirmed by the Karl Fischer method.

The NMR spectrum of the compound obtained was consistent with the NMR spectrum of the compound according to Example 7 of International Publication No. WO 00/47599.

(Example 7-4a) Production of Compound 17

[Formula 119]

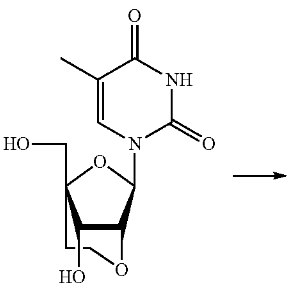

16

To a tetrahydrofuran solution (150 mL) of the compound 16 (30 g) were added pyridine (33.39 g) and 4,4'-dimethoxytrityl chloride (42.91 g), followed by stirring at 20 to 30° C. for 3 hours, and then methanol (6 mL) was added thereto, followed by further stirring at 20 to 30° C. for 30 minutes. To the solution obtained were added a 15% aqueous sodium carbonate solution (150 mL), ethyl acetate (300 mL), and water (210 mL) for liquid separation. The organic layer obtained was washed with a 20% aqueous citric acid solution (150 mL) twice and with a 5% aqueous sodium bicarbonate solution (150 mL) and water (150 mL) once for liquid separation. The organic layer obtained was concentrated under reduced pressure to 150 mL, then the solvent was substituted with ethyl acetate (300 mL) by concentration under reduced pressure twice, and ethyl acetate (90 mL) was added thereto, to obtain an ethyl acetate solution (240 mL) of the compound 17. To the solution obtained was added n-heptane (90 mL), followed by heating to 50° C., and then seed crystals (30 mg) were added, followed by stirring at the same temperature for 2 hours. The slurry solution obtained was cooled to 20 to 30° C., followed by stirring at the same temperature for 15 hours. To the slurry solution obtained was added n-heptane (120 mL), followed by further stirring at the same temperature for 1 hour. The crystals precipitated were collected by filtration and washed with a 1:1 mixed solution (100 mL) of ethyl acetate and n-heptane. The crystals obtained were dried under reduced pressure (50° C.), to obtain the compound 17 (60.7 g, yield 98%).

The NMR spectrum of the compound obtained was consistent with the NMR spectrum of the compound according to Example 8 of International Publication No. WO 00/47599.

The seed crystals of the compound 17 used were those precipitated by allowing the ethyl acetate solution of the compound 17 obtained in Example 2-3 to stand.

(Example 8a) Production of Compound 1a

[Formula 120]

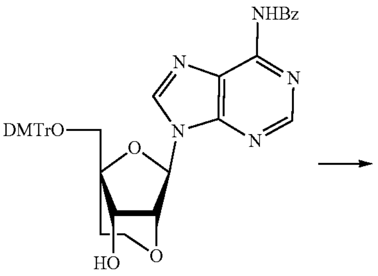

21

-continued

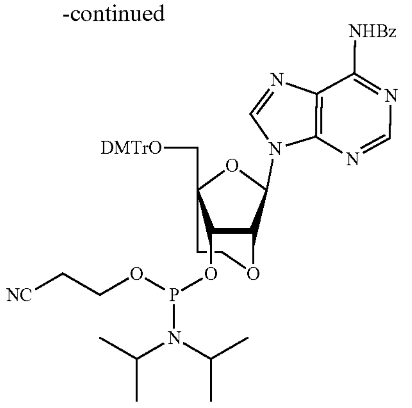

1a

To dichloromethane (675 mL) was added the hydrate (45.00 g, 64.31 mmol) of the compound 21 obtained in Example 4-3, followed by concentration under reduced pressure, to obtain a dichloromethane solution (225 mL). To the dichloromethane solution obtained was added dichloromethane (450 mL), followed by concentration under reduced pressure, to obtain a dichloromethane solution (225 mL). The same operation was repeated again, and to the dichloromethane solution (225 mL) obtained were added dichloromethane (225 mL), molecular sieve 4A (22.50 g), dibutylhydroxytoluene (1.42 g, 6.44 mmol), 2-cyanoethyl N,N,N',N'-tetraisopropyl phosphorodiamidite (21.32 g, 70.73 mmol), and 4,5-dicyanoimidazole (0.91 g, 7.71 mmol), followed by stirring at 20 to 30° C. for 16.5 hours. Completion of the reaction was confirmed, ethyl acetate (900 mL) was added to the reaction solution, and neutral silica gel (67.50 g) was added thereto at −5 to 5° C., followed by stirring for 15 minutes. Thereafter, the neutral silica gel was filtered out and washed with dichloromethane-ethyl acetate (1/2, 225 mL), to obtain a dichloromethane-ethyl acetate solution. The dichloromethane-ethyl acetate solution obtained was concentrated under reduced pressure, to give an ethyl acetate solution (225 mL). To the solution obtained was added methyl tert-butyl ether (135 mL), to obtain the solution A (360 mL). To another reaction container were added methyl tert-butyl ether (315 mL) and n-heptane (1350 mL), and the solution A (360 mL) was added thereto at −5 to 5° C., to confirm precipitation of a solid. After washing with ethyl acetate (23 mL) and stirring for 0.5 hours, the solid precipitated was filtered and washed with methyl tert-butyl ether-n-heptane (1/3, 225 mL) cooled to 0° C. in advance and n-heptane (225 mL). The solid obtained was dried under reduced pressure (40° C.), to obtain a compound 1a (48.69 g, 84.1%).

The NMR spectrum of the compound obtained was consistent with the NMR spectrum of the compound according to Example 14 of International Publication No. WO 00/47599.

(Example 8b) Production of Compound 1a

To dichloromethane (45 mL) was added the hydrate (3.57 g) of the compound 21 obtained in Example 4-3, followed by concentration under reduced pressure, to obtain a dichloromethane solution (15 mL). To the dichloromethane solution obtained were added dichloromethane (15 mL), molecular sieve 4A (22.50 g), 2-cyanoethyl N,N,N',N'-tetraisopropyl phosphorodiamidite (1.42 g), and 4,5-dicyanoimidazole (100 mg), and then the reaction mixture was stirred at 20 to 30° C. for 24 hours. Completion of the reaction was confirmed, and then to the reaction solution was added ethyl acetate (60 mL). The solution obtained was cooled to −5 to 5° C., then passed through a column filled with neutral silica gel (4.5 g), and washed with dichloromethane-ethyl acetate (1/2, 30 mL), to obtain a dichloromethane-ethyl acetate solution. The dichloromethane-ethyl acetate solution obtained was concentrated under reduced pressure, to give an ethyl acetate solution (15 mL), and then toluene (60 mL) was added thereto, followed by concentration again, to obtain a toluene solution (15 mL). To the solution obtained was added methyl tert-butyl ether (9 mL), to obtain the solution A (24 mL). To another reaction container were added methyl tert-butyl ether (6 mL) and n-heptane (90 mL), and then the solution A (24 mL) was added dropwise thereto at −5 to 5° C., to confirm precipitation of a solid. The instrument used for the dropwise addition was washed with toluene (1.5 mL), followed by stirring for 2 hours, and then the solid precipitated was filtered and washed with n-heptane (24 mL). The solid obtained was dried under reduced pressure (40° C.), to obtain a compound 1a (3.97 g, 86.5%).

The NMR spectrum of the compound obtained was consistent with the NMR spectrum of the compound according to Example 14 of International Publication No. WO 00/47599.

(Example 9) Production of Compound 1t

[Formula 121]

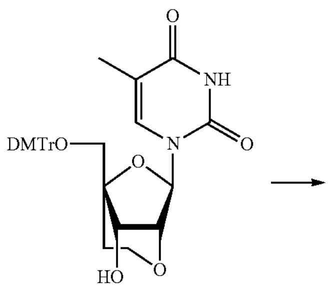

17

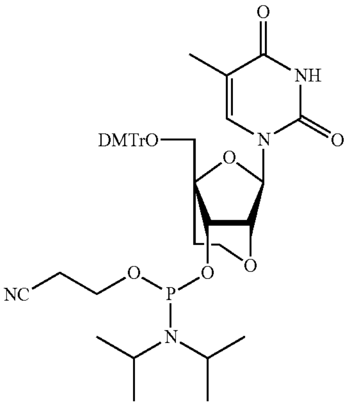

1t

To ethyl acetate (40 mL) was added the compound 17 (5.00 g, 8.52 mmol) obtained in Example 2-3, and then molecular sieve 4A (2.5 g), 2-cyanoethyl N, N,N', N'-tetraisopropyl phosphorodiamidite (2.83 g, 9.38 mmol), and 4,5-dicyanoimidazole (0.20 g, 1.70 mmol) were added thereto, followed by stirring at 20 to 30° C. for 24 hours. Completion of the reaction was confirmed, and then to the reaction solution was added neutral silica gel (10.00 g), followed by stirring for 30 minutes. Thereafter, the neutral silica gel was filtered out and washed with ethyl acetate (100 mL), to obtain an ethyl acetate solution. The ethyl acetate solution obtained was concentrated under reduced pressure, to give an ethyl acetate solution (35 mL). To the ethyl acetate solution obtained was added tert-butyl ether (100 mL), followed by concentration under reduced pressure, to obtain a methyl tert-butyl ether solution (35 mL). To the methyl tert-butyl ether solution obtained were added the seed crystals (2.5 mg) of the compound 1t, followed by stirring for 2 hours, and then n-heptane (100 mL) was added thereto, followed by cooling to 0 to 5° C. and further stirring for 2 hours. The solid precipitated was filtered and washed with n-heptane (100 mL) cooled to 0° C. in advance. The solid obtained was dried under reduced pressure (40° C.), to obtain the compound 1t (6.12 g, 91.3%).

The NMR spectrum of the compound obtained was consistent with the NMR spectrum of the compound according to Example 9 of International Publication No. WO 00/47599.

The seed crystals of the compound 1t used were those precipitated by allowing the mixed solution of ethyl acetate, diisopropyl ether, and n-heptane of the compound 1t obtained in Example 2-4 to stand.

(Example 10) Production of Compound 1c (Example 10-1) Production of 1-(3-O-acetyl-2,6-anhydro-4-{[bis(4-methoxyphenyl) (phenyl) methoxy]methyl}-5-deoxy-a-L-lyxo-hexofuranosyl)-5-methylpyrimidine-2,4(1H,3H)-dione (Compound 30)

[Formula 122]

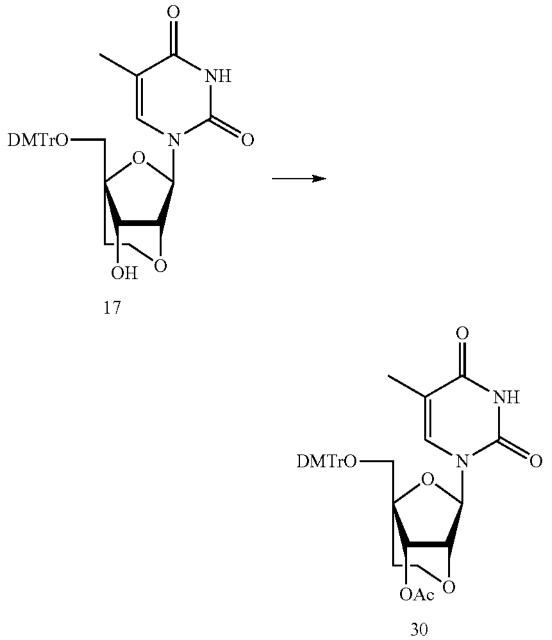

17

30

To ethyl acetate (320 mL) were added the compound 17 (80.00 g, 136.37 mmol) obtained in Example 2-3, N,N-dimethylaminopyridine (1.67 g, 13.64 mmol), and triethylamine (27.60 g, 272.74 mmol), followed by cooling to 0 to 5° C., and then acetic anhydride (16.71 g, 163.64 mmol) was added thereto at the same temperature. After stirring at 0 to 5° C. for 1 hour, water (160 mL) was added for liquid separation, and the organic layer obtained was washed with a 10% aqueous citric acid solution (160 mL), a 5% aqueous sodium bicarbonate solution (160 mL), and 10% saline (160 mL) for liquid separation. The organic layer obtained was concentrated under reduced pressure to 240 mL, and then the solvent was substituted with acetonitrile (400 mL) by concentration under reduced pressure twice, to obtain an acetonitrile solution (240 mL) of a compound 30.

(Example 10-2) Production of 1-(3-O-acetyl-2,6-anhydro-4-{[bis(4-methoxyphenyl) (phenyl) methoxy]methyl}-5-deoxy-a-L-lyxo-hexofuranosyl)-4-amino-5-methylpyrimidin-2(1H)-one (Compound 31)

[Formula 123]

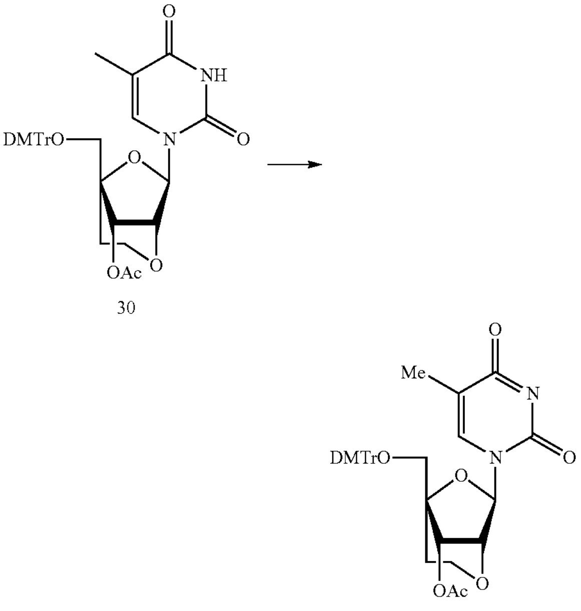

30

31

To the solution of the compound 30 obtained in Example 10-1 were added acetonitrile (160 mL), N,N-dimethylaminopyridine (3.33 g, 27.27 mmol), and triethylamine (55.20 g, 545.51 mmol), followed by cooling to 5 to 15° C., and then 2,4,6-triisopropylbenzenesulfonyl chloride (47.50 g, 156.83 mmol) was added thereto at the same temperature. After stirring at 10° C. for 2 hours, 25% ammonia water (100 kg, 156.83 mmol) was added thereto, followed by stirring at 20° C. for 2 hours. The solution obtained was concentrated under reduced pressure to about 320 mL, and then ethyl acetate (400 mL) and water (120 mL) were added thereto for liquid separation. The organic layer obtained was washed with 10% saline (160 mL) for liquid separation twice, and then acetonitrile (400 mL) was added thereto, followed by concentration under reduced pressure to about 320 mL. To the concentrated solution obtained was added acetonitrile (400 mL), followed by concentration under reduced pressure, to obtain an acetonitrile solution (B) (240 mL) of a compound 31. In the case where the water content in the acetonitrile solution (B) was over 0.4% in the aforementioned procedure, the step of concentration and dehydration by adding acetonitrile to the acetonitrile solution (B) was repeated until the water content in the acetonitrile solution (B) was 0.4% or less, so that the following reaction could rapidly proceed.

The water content was confirmed by the Karl Fischer method.

(Example 10-3a) Production of Compound 19

[Formula 124]

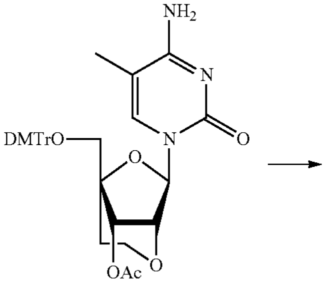

31

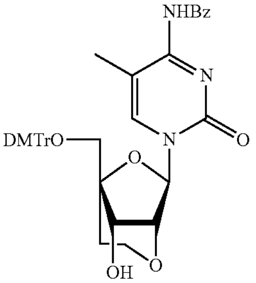

19

To an acetonitrile solution of the compound 31 obtained in Example 10-2 were added THF (80 mL) and benzoic anhydride (67.87 g, 300.01 mmol), followed by stirring at 40° C. for 5 hours, then cooling to 25° C., and further stirring for 15 hours. The slurry solution obtained was added dropwise to a mixed solution of water (80 mL), a 25% aqueous sodium hydroxide solution (176 g), and THF (80 mL) at 5 to 15° C. over 1 hour or more. To the mixed solution obtained was added THF (160 mL), followed by stirring at 20° C. for 2 hours, and then the pH of the solution was adjusted to 6.8 using acetic acid. To the solution obtained were added the hydrated crystals (80 mg) of the compound 19 obtained in Example 3-3 as seed crystals, followed by stirring for 10 hours, and then water (400 mL) was added dropwise thereto at 15 to 25° C. over 2 hours or more. The slurry solution obtained was stirred at 20° C. for 1 hour, and then the crystals precipitated were filtered and washed with 40% THF water (400 mL). The crystals obtained were dried at 50° C. under reduced pressure, to obtain the compound 19 (78.35 g, 83.3% G/G (from the compound 17)).

The NMR spectrum of the compound obtained was consistent with the NMR spectrum of the compound according to Example 21 of International Publication No. WO 00/47599.

(Example 10-3b) Production of Compound 19

To an acetonitrile solution (90 mL) of the compound 31 obtained in Example 10-2 were added THF (80 mL) and benzoic anhydride (23.14 g, 102.3 mmol), followed by stirring at 40° C. for 5 hours, cooling to 25° C., and further stirring for 20 hours. To the slurry solution obtained were added THF (30 mL) and potassium acetate (23.09 g, 235.3 mmol), followed by stirring for 1 hour, and then 8% saline (135 mL) was added thereto for liquid separation. To the organic layer obtained were added THF (15 mL), water (15 mL), and a 25% aqueous sodium hydroxide solution (33 g), followed by cooling to 0 to 10° C., and then a 25% aqueous sodium hydroxide solution (15 g) and water (6 mL) were further added thereto, followed by stirring at 0 to 10° C. for 4 hours. Completion of the reaction was confirmed, and the pH of the solution obtained was adjusted to 6.5 using acetic acid. To the solution obtained were added sodium chloride (6.0 g) and THF (60 mL) for liquid separation, and to the organic layer obtained were added THF (30 mL), water (45 mL), and the hydrated crystals (30 mg) of the compound 19 obtained in Example 3-3 as seed crystals, followed by stirring for 16 hours. Thereafter, water (180 mL) was added dropwise thereto at 20 to 30° C. over 2 hours or more. The slurry solution obtained was stirred at 20 to 30° C. for 3 hours, and then the crystals precipitated were filtered and washed with 40% THF water (150 mL). The crystals obtained were dried at 50° C. under reduced pressure, to obtain the compound 19 (28.48 g, 80.7% G/G (from the compound 17)).

In the aforementioned procedure, the amount of acetic acid used for adjusting the pH during crystallization could be controlled to an amount smaller than in the procedure of Example 10-3a by using potassium acetate, thereby enabling the time required for crystallization to be further shortened.

The NMR spectrum of the compound obtained was consistent with the NMR spectrum of the compound according to Example 21 of International Publication No. WO 00/47599.

(Example 11) Production of Compound 1c

[Formula 125]

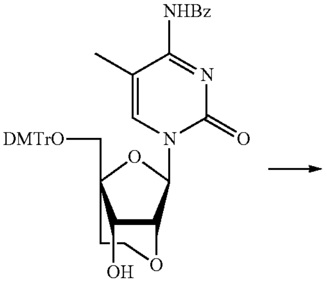

19

-continued

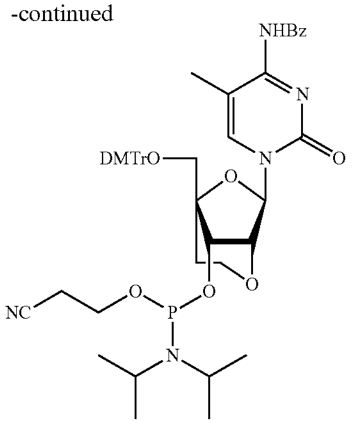

1c

To dichloromethane (400 mL) was added the compound 19 (20.00 g, 29.00 mmol) obtained in Example 10-3, followed by concentration under reduced pressure, to obtain a dichloromethane solution (200 mL). To the dichloromethane solution obtained was added dichloromethane (200 mL), followed by concentration under reduced pressure, to obtain a dichloromethane solution (200 mL). The same operation was repeated again, and to the dichloromethane solution obtained (200 mL) were added molecular sieve 4A (10.00 g), dibutylhydroxytoluene (0.64 g, 2.90 mmol), 2-cyanoethyl N,N,N',N'-tetraisopropyl phosphorodiamidite (9.61 g, 31.89 mmol), and 4,5-dicyanoimidazole (1.03 g, 8.70 mmol), followed by stirring at 20 to 30° C. for 4 hours. Completion of the reaction was confirmed, ethyl acetate (100 mL) was added to the reaction solution, and neutral silica gel (40.00 g) was added thereto at −5 to 5° C., followed by stirring for 30 minutes. Then, the neutral silica gel was filtered out and washed with dichloromethane-ethyl acetate (2/1, 100 mL), to obtain a dichloromethane-ethyl acetate solution. The dichloromethane-ethyl acetate solution obtained was concentrated under reduced pressure, to give a dichloromethane-ethyl acetate solution (100 mL). To the dichloromethane-ethyl acetate solution obtained was added ethyl acetate (100 mL), followed by concentration under reduced pressure, to obtain an ethyl acetate solution (100 mL). The same operation was repeated again, and to the solution obtained was added methyl tert-butyl ether (100 mL), followed by concentration under reduced pressure, to give an ethyl acetate-methyl tert-butyl ether solution (100 mL). To the ethyl acetate-methyl tert-butyl ether solution obtained was added methyl tert-butyl ether (100 mL), followed by concentration under reduced pressure, to obtain a methyl tert-butyl ether solution (100 mL). The same operation was repeated again, and to the solution obtained was added n-heptane (200 mL), followed by stirring for 1.5 hours. Thereafter, n-heptane (100 mL) was further added thereto, followed by stirring for 1 hour, and n-heptane (200 mL) was added thereto again, followed by stirring for 1.5 hours, to confirm precipitation of a solid. The solid precipitated was filtered and washed with n-heptane (200 mL) cooled to 0° C. in advance. The solid obtained was dried under reduced pressure (40° C.), to obtain a compound 1c (22.40 g, 86.8%).

The NMR spectrum of the compound obtained was consistent with the NMR spectrum of the compound according to Example 6 of International Publication No. WO 00/47599.

(Example 12) Stereoselective glycosylation of the Compound 22

[Formula 126]

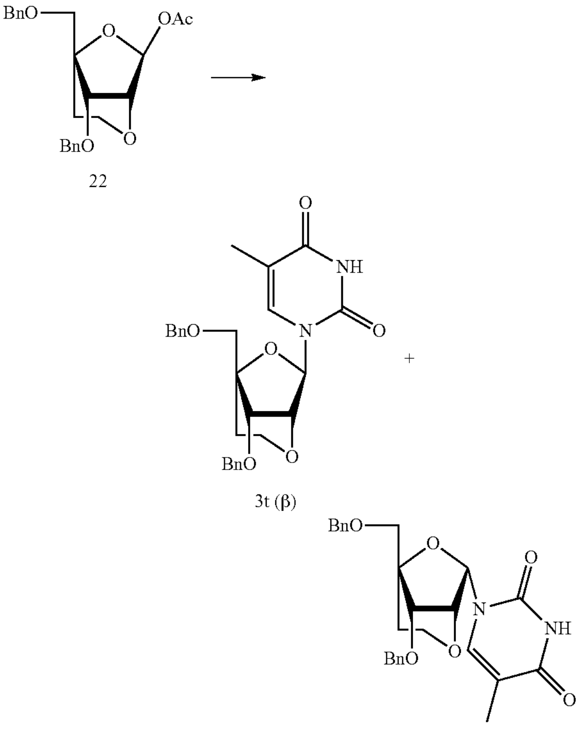

22

3t (β)

3t (α)

To the compound 22 (30 mg, 0.075 mmol) obtained in Example 5-1 and bistrimethylsilyl thymine (40.8 mg, 0.151 mmol) was added 1,2-dichloroethane (0.3 mL), followed by stirring at room temperature. Thereafter, chlorotrimethylsilane (TMSCl), bromotrimethylsilane (TMSBr), iodotrimethylsilane (TMSI), and trimethylsilyl trifluoromethanesulfonate (TMSOTf) as activators were added each in an amount of 2.0 equivalents (0.151 mmol) to the starting material, followed by stirring at temperatures shown in the table. The reaction solution was sampled, and the starting material, the α-adduct, and the β-adduct were analyzed by HPLC. Table 1 shows the results.

TABLE 1

| Activator | Reaction (° C.) temperature | Reaction (h) time | HPLC P. A. (%)/210 nm 22 | 3t (β) | 3t (α) | β:α |
|---|---|---|---|---|---|---|
| TMSCl | 70 | 18 | 97.62 | N.D. | N.D. | — |
| TMSBr | 70 | 28 | 7.03 | 67.98 | 21.80 | 75.7:24.3 |
| TMSI | 25 | 4 | 4.30 | 74.38 | 16.62 | 81.7:18.3 |
| TMSOTf | 25 | 45 | 4.14 | 3.49 | 90.19 | 3.7:96.3 |

As a result of the examination, the α-adduct was stereoselectively obtained under the conditions using TMSOTf, whereas the β-adduct was stereoselectively obtained under the conditions using TMSBr and TMSI. Among them, the reaction proceeded well even at room temperature when using TMSI.

(Example 13) Screening of Activator for Amidite-Formation

[Formula 127]

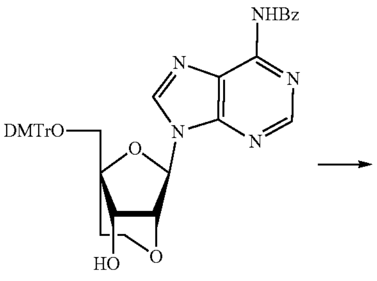

21

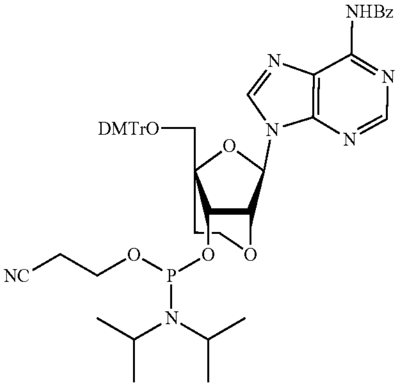

1a

To dichloromethane (1 mL) were added the hydrate (100 mg, 0.14 mmol) of the compound 21 obtained in Example 4-3,2-cyanoethyl N,N,N',N'-tetraisopropyl phosphorodiamidite (51.7 mg, 0.17 mmol), and 5-benzylthiotetrazole, 5-phenyltetrazole, 4,5-dicyanoimidazole, and 2,4,5-tribromoimidazole as activators, each in an amount of 1.15 equivalents (0.16 mmol), to the starting material, followed by stirring at 20 to 30° C. Table 2 shows the results of confirming completion of the reaction by HPLC.

TABLE 2

| Activator | Reaction time (h) | HPLC area percentage (%) 1a |
|---|---|---|
| 5-Benzylthiotetrazole | 3 | 93.57 |
| 5-Phenyltetrazole | 22 | 88.94 |
| 4,5-Dicyanoimidazole | 3 | 95.36 |
| 2,4,5-Tetrabromoimidazole | 48 | 96.45 |

As a result of the examination, good results were obtained under the conditions using 4,5-dicyanoimidazole and 2,4,5-tribromoimidazole.

(Example 14) Verification of Molecular Sieve Effect

[Formula 128]

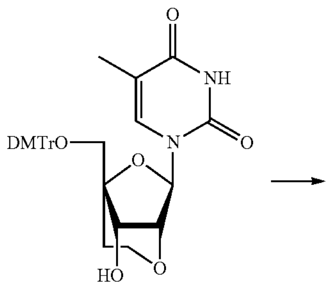

17

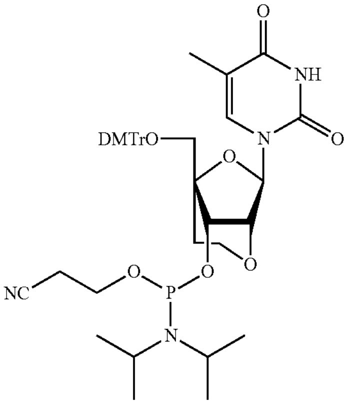

1t

To dichloromethane (10 v/w) were added the compound 17 obtained in Example 2-3, dibutylhydroxytoluene (0.10 equivalent), 2-cyanoethyl N,N,N',N'-tetraisopropyl phosphorodiamidite (1.10 equivalent), and 4,5-dicyanoimidazole (1.0 equivalent), followed by stirring at 20 to 30° C. in the presence or absence of molecular sieve 4A (0.5 wt %). Table 3 shows the results of confirming the progress of the reaction by HPLC.

TABLE 3

| Molecular sieve 4A | HPLC area percentage (%) | |
|---|---|---|
| (wt %) | 17 | 1t |
| None | 2.8 | 96.5 |
| 0.5 | 0.07 | 98.5 |

By using the molecular sieve, the compound 17 was completely converted into the compound 1t.

(Example 15) Synthesis of oligonucleotide

An oligonucleotide consisting of a desired sequence/structure can be synthesized by the following method.

Using an automatic nucleic acid synthesizer ("ABI 394 DNA/RNA Synthesizer", available from Applied Biosystems), synthesis is performed according to the phosphoramidite method (NucleicAcids Research, 12, 4539 (1984)). As a reagent, activator solution-3 (product No. 013-20011, a 0.25 mol/L 5-benzylthio-1H-tetrazole/acetonitrile solution, available from Wako Pure Chemical Industries, Ltd.), CAP A for AKTA (product No. L040050, a 1-methylimidazole/acetonitrile solution, available from Sigma-Aldrich Co. LLC), Cap B1 for AKTA (product No. L050050, an acetic anhydride/acetonitrile solution, available from Sigma-Aldrich Co. LLC), Cap B2 for AKTA (product No. L050150, a pyridine/acetonitrile solution, available from Sigma-Aldrich Co. LLC), or DCA Deblock (product No. L023050, a dichloroacetic acid/toluene solution, available from Sigma-Aldrich Co. LLC) is used. As a thiation reagent for forming a phosphorothioate bond, phenyl acetyl disulfide (product No. FP07495, available from Carbosynth Holdings Limited) dissolved in a 1:1 (v/v) solution of acetonitrile (product No. 01837-05, dehydrated, available from KANTO CHEMICAL CO., INC.) and pyridine (product No. 11339-05, dehydrated, available from KANTO CHEMICAL CO., INC.) to 0.2M is used. As an amidite reagent, phosphoramidite of 2'-O-Me nucleoside (adenosine, product No. ANP-5751, cytidine, product No. ANP-5752, guanosine, product No. ANP-5753, or uridine, product No. ANP-5754) available from ChemGenes is used. As ENA monomers such as 9-(2,6-anhydro-4-{[bis(4-methoxyphenyl) (phenyl) methoxy]methyl}-3-O-{(2-cyanoethoxy) [di(propane-2-yl) amino]phosphanyl}-5-deoxy-α-L-lyxo-hexofuranosyl)-N-benzoyl-9H-purin-6-amine (Compound 1a), 1-(2,6-anhydro-4-{[bis(4-methoxyphenyl) (phenyl)methoxy] methyl}-3-O-{(2-cyanoethoxy) [di(propane-2-yl)amino] phosphanyl}-5-deoxy-a-L-lyxo-hexofuranosyl)-4-benzamide-5-methylpyrimidin-2 (1H)-one (Compound 1c), and 1-(2,6-anhydro-4-{[bis(4-methoxyphenyl) (phenyl) methoxy]methyl}-3-O-{(2-cyanoethoxy) [di(propane-2-yl) amino]phosphanyl}-5-deoxy-a-L-lyxo-hexofuranosyl)-5-methylpyrimidine-2,4(1H,3H)-dione (Compound 1t), the compounds synthesized in the aforementioned examples are used. Glen Unysupport 0.1 μmol (available from GlenResearch) can be used as a solid-phase carrier, to synthesize an oligonucleotide having a desired sequence. The program used for 0.2 μmol scale attached to the automatic nucleic acid synthesizer is used, where, however, the time required for condensation of amidite is 600 seconds, and the time required for thiation is 150 seconds.

An oligonucleotide having a ligand unit at the 5' end can be synthesized following the synthesis of the nucleotide chain, according to the method disclosed in International Publication No. WO 2019/172286, by reacting the phosphoramidite of the ligand unit in the same manner. As the phosphoramidite compounds corresponding to $X^{18}$ and $X^{20}$, which are GalNAc units, the compound 39D of Reference Example 39 and the compound 41D of Reference Example 41 according to International Publication No. WO 2019/172286 are respectively used.

While oligomers are cleaved from the support by treating protected oligonucleotide analogs having the target sequence with 300 μL of concentrated ammonia water, protecting cyanoethyl groups on phosphorus atoms and protective groups on nucleobases are removed. Using Clarity QSP (available from Phenomenex Inc.), purification is performed according to the protocol attached.

INDUSTRIAL APPLICABILITY

The present invention provides a crystalline 2,4-bridged common intermediate useful for producing various ENA monomers and a method for stereoselectively producing the intermediate, thereby enabling various ENA monomers to be produced efficiently.

The invention claimed is:

1. A compound represented by formula (I'):

(I')

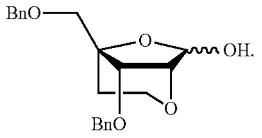

2. A method for producing a compound represented by formula (VI):

(VI)

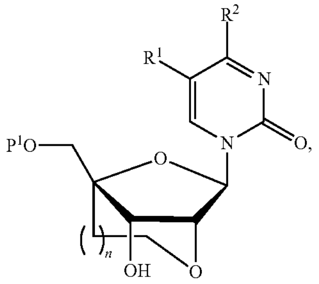

or a salt or a tautomer thereof;

wherein:

$R^1$ represents a lower alkyl group or a hydrogen atom;

$R^2$ represents a hydroxyl group, an amino group, or an amino group protected by an aliphatic acyl group or an aromatic acyl group;

$P^1$ represents a trityl group optionally substituted with 1 to 3 lower alkoxy groups;

n represents an integer of 0 to 4;

$Z^1$ and $Z^2$ are identical or different and each represent a protective group for a hydroxy group; and $X^1$ represents a group that forms a leaving group.

3. A method for producing a compound represented by formula (X):

(X)

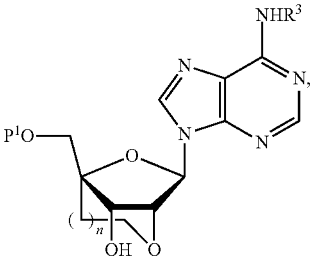

or a salt or a tautomer thereof, the method comprising:

(i) a step of reacting a compound represented by formula (II):

(II)

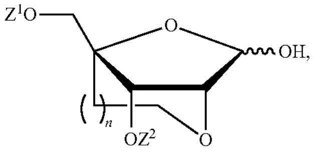

with an activator in a solvent, to convert a hydroxyl group at the 1-position into a group that forms a leaving group;

(ii) a step of reacting the compound represented by formula (XI) obtained in step (i):

(XI)

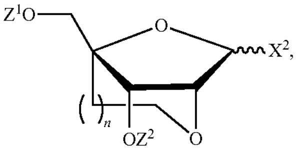

with a compound represented by formula (XII):

(XII)

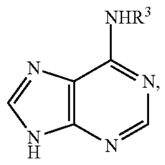

or a salt or a tautomer thereof, in a solvent in the presence of an acid reagent;

(iii) a step of performing isomerization, to stereoselectively obtain a compound represented by formula (XIII):

(XIII)

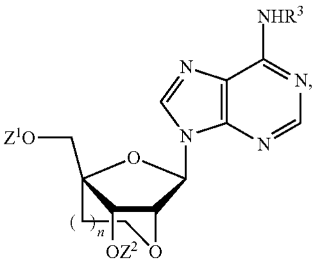

or a salt or a tautomer thereof;

(iv) a step of reacting the compound represented by formula (XIII) obtained in step (iii):

(XIII)

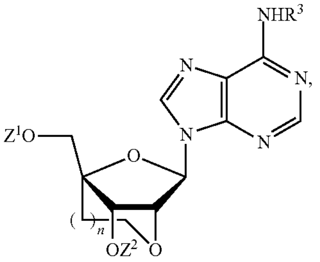

or a salt or a tautomer thereof, with a deprotection reagent for a hydroxyl group in a solvent, to deprotect $Z^1$ and $Z^2$; and (v) a step of reacting the diol compound obtained in step (iv) or a salt or a tautomer thereof, with a protection reagent for a primary hydroxyl group and selectively protecting the primary hydroxyl group, to obtain a compound represented by formula (X):

(X)

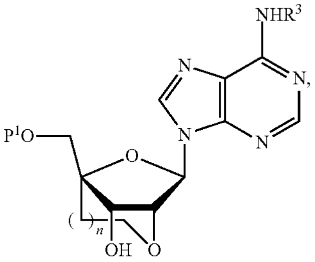

or a salt or a tautomer thereof;

wherein:

$R^3$ represents an aliphatic acyl group or an aromatic acyl group;

$P^1$ represents a trityl group optionally substituted with 1 to 3 lower alkoxy groups;

n represents an integer of 0 to 4;

$Z^1$ and $Z^2$ are identical or different and each represent a protective group for a hydroxy group; and $X^2$ represents a group that forms a leaving group.

4. A compound represented by formula (XIV):

(XIV)

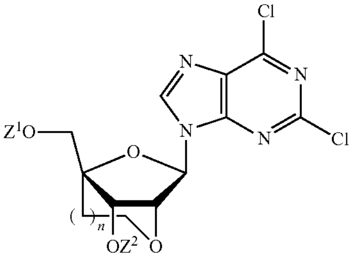

wherein $Z^1$ and $Z^2$ are identical or different and each represent a protective group for a hydroxy group, and n represents an integer of 0 to 4, or a salt thereof.

5. A compound represented by formula (XIV'):

(XIV')

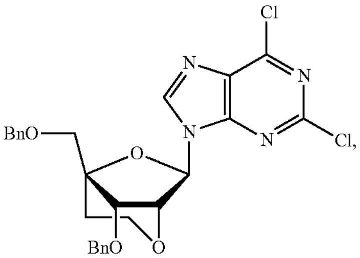

6. A method for producing a compound represented by formula (XVIII):

(XVIII)

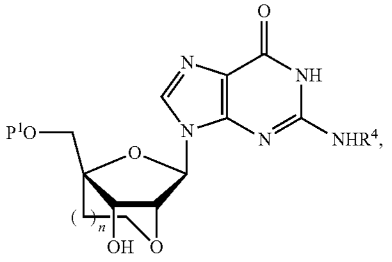

or a salt or a tautomer thereof, the method comprising:

(i) a step of reacting a compound represented by formula (XIV):

(XIV)

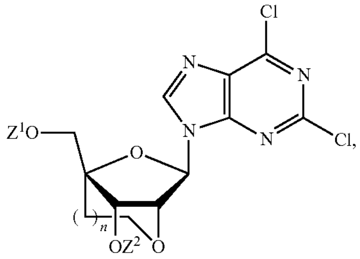

or a salt thereof, with benzyl alcohol optionally substituted with a lower alkyl, lower alkoxy, halogen, or cyano group in a solvent in the presence of a base, to replace the chlorine atom at the 6-position of the purine ring with a benzyloxy group optionally substituted with a lower alkyl, lower alkoxy, halogen, or cyano group;

(ii) a step of cross-coupling the compound represented by formula (XIX) obtained in step (i):

(XIX)

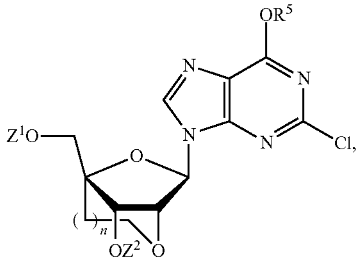

or a salt thereof, with an amidating agent in a solvent in the presence of a palladium catalyst and a phosphine ligand, to obtain a compound represented by formula (XX):

(XX)

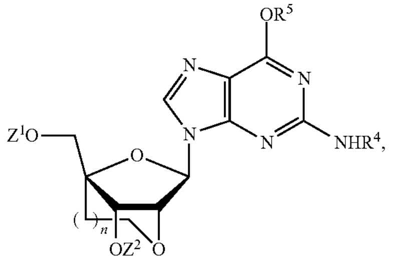

or a salt or a tautomer thereof;

(iii) a step of reacting the compound represented by formula (XX) obtained in step (ii):

(XX)

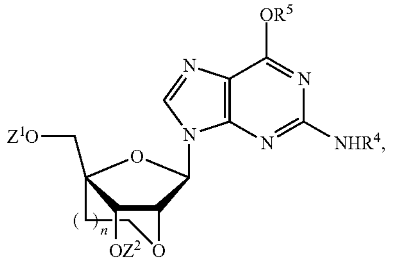

or a salt or a tautomer thereof, with a deprotection reagent for a hydroxyl group in a solvent, to deprotect $Z^1$, $Z^2$ and $R^5$; and (iv) a step of reacting the compound represented by formula (XXI) obtained in step (iii):

(XXI)

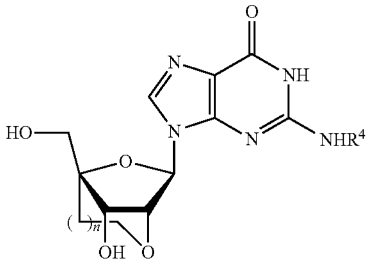

or a salt or a tautomer thereof, with a protection reagent for a primary hydroxyl group and selectively protecting the primary hydroxyl group, to obtain a compound represented by formula (XVIII):

(XVIII)

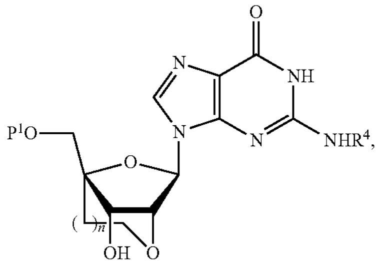

or a salt or a tautomer thereof;

wherein:

$P^1$ represents a trityl group optionally substituted with 1 to 3 lower alkoxy groups;

$R^4$ represents an aliphatic acyl group or an aromatic acyl group;

n represents an integer of 0 to 4;

wherein $Z^1$ and $Z^2$ are identical or different and each represent a protective group for a hydroxy group; and $R^5$ represents a benzyl group optionally substituted with a lower alkyl, lower alkoxy, halogen, or cyano group.

7. A method for producing a compound represented by formula (XXII):

(XXII)

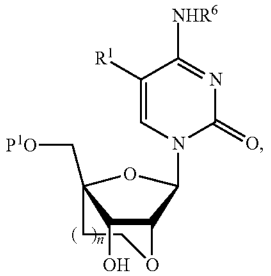

or a salt or a tautomer thereof, the method comprising:

(i) a step of reacting a compound represented by formula (XXIII):

(XXIII)

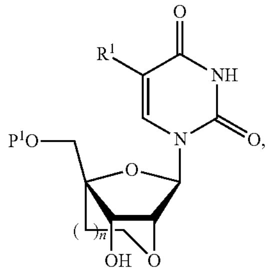

or a salt or a tautomer thereof, with a protection reagent for a hydroxyl group in a solvent, to protect the hydroxyl group at the 3-position;

(ii) a step of reacting the compound represented by formula (XXIV) obtained in step (i):

(XXIV)

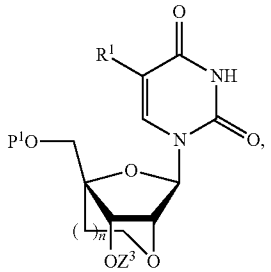

or a salt or a tautomer thereof, with an activator in a solvent in the presence of a base and a catalyst;

(iii) a step of then performing a reaction with an aminating agent, to obtain a compound represented by formula (XXV):

(XXV)

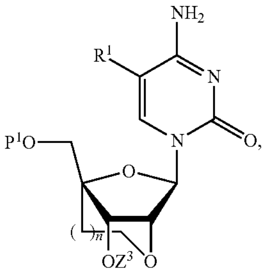

or a salt or a tautomer thereof;

(iv) a step of reacting the compound represented by formula (XXV) obtained in step (iii):

(XXV)

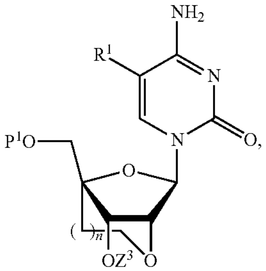

or a salt or a tautomer thereof, with an acylating agent in a solvent, and (v) a step of reacting the compound represented by formula (XXVI) obtained in step (iv):

(XXVI)

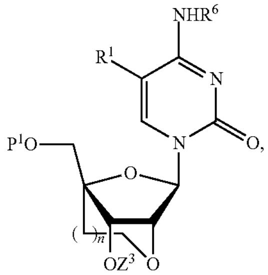

or a salt or a tautomer thereof, with a deprotection reagent for a hydroxyl group and deprotecting only $Z^3$, to obtain a compound represented by formula (XXII):

(XXII)

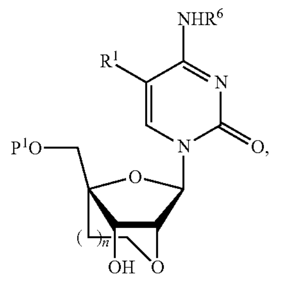

a salt or a tautomer thereof, wherein:

$R^1$ represents a lower alkyl group or a hydrogen atom;

$R^6$ represents an aliphatic acyl group or an aromatic acyl group;

$P^1$ represents a trityl group optionally substituted with 1 to 3 lower alkoxy groups;

n represents an integer of 0 to 4; and $Z^3$ represents an aliphatic acyl group or an aromatic acyl group.

8. A production method comprising the steps of:

reacting a compound represented by formula (XXVII):

(XXVII)

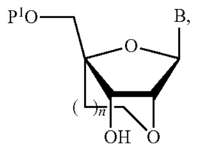

or a salt or a tautomer thereof, with an amidite-forming reagent in a solvent in the presence of an activator and a drying agent, to produce a compound represented by formula (XXVIII):

(XXVIII)

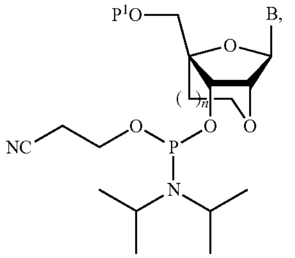

or a salt or a tautomer thereof wherein:

$P^1$ represents a trityl group optionally substituted with 1 to 3 lower alkoxy groups;

B represents a 2-oxo-pyrimidin-1-yl group optionally having one or more substituents selected from the group α below or a purin-9-yl group;

n represents an integer of 0 to 4; and group α represents a hydroxyl group, a protected hydroxyl group, a lower alkoxy group, a mercapto group, a protected mercapto group, a lower alkylthio group, an amino group, a protected amino group, a lower alkylamino group, a lower alkyl group, or a halogen atom.

9. A method for producing an oligonucleotide, comprising:

(A) a step of synthesizing an ENA monomer by the method according to claim 8; and (B) a step of extending the nucleotide chain according to a desired sequence using the ENA monomer obtained in step (A); and a phosphoramidite compound of another nucleic acid, and/or a phosphoramidite compound of a ligand.

10. The method according to claim 9, wherein the oligonucleotide consists of a sequence represented by any one formula selected from DMD AO01 to DMD A015 below:

(SEQ ID NO: 1)
(DMD AO01) HO-$C^{e2s}$-$A^{m1s}$-$G^{m1s}$-$T^{e2s}$_$T^{e2s}$-$U^{m1s}$-$G^{m1s}$-$C^{e2s}$-$C^{e2s}$-$G^{m1s}$-$C^{e2s}$-$T^{e2s}$-$G^{m1s}$-$C^{e2s}$-$C^{e2s}$-$C^{e2s}$-$A^{m1s}$-$A^{m1s}$-$CH_2CH_2OH$;

(SEQ ID NO: 2)
(DMD AO02) HO-$T^{e2s}$-$G^{m1s}$-$T^{e2s}$-$T^{e2s}$-$C^{e2s}$-$T^{e2s}$-$G^{m1s}$-$A^{m1s}$-$C^{e2s}$-$A^{m1s}$-$A^{m1s}$-$C^{e2s}$-$A^{m1s}$-$G^{m1s}$-$T^{e2s}$-$T^{e2s}$-$T^{e2s}$-$G^{m1s}$-$CH_2CH_2OH$;

(SEQ ID NO: 3)
(DMD AO03) HO-$C^{e2s}$-$G^{m1s}$-Ce25-$T^{e2s}$-$G^{m1s}$-$C^{m1s}$-$C^{e2s}$-$C^{e2s}$-$A^{m1s}$-$A^{m1s}$-$T^{e2s}$-$G^{m1s}$-$C^{e2s}$-$C^{e2s}$-$A^{m1s}$-$U^{m1s}$-$C^{e2s}$-$C^{e2s}$-$CH_2CH_2OH$;

(SEQ ID NO: 4)
(DMD AO04) HO-$C^{e2s}$-$A^{m1s}$-$T^{e2s}$-$A^{m1s}$-$A^{m1s}$-$T^{e2s}$-$G^{m1s}$-$A^{m1s}$-$A^{e2s}$-$A^{m1s}$-$A^{m1s}$-$C^{e2s}$-$G^{m1s}$-$C^{m1s}$-$C^{e2s}$-$G^{m1s}$-$C^{e2s}$-$C^{e2s}$-$CH_2CH_2OH$;

(SEQ ID NO: 5)
(DMD AO05) HO-$T^{e2s}$-$U^{m1s}$$C^{e2s}$-$C^{m1s}$-$C^{e2s}$-Ande-A $^{m1s}$-$T^{e2s}$-$U^{m1s}$-$C^{m1s}$-$T^{e2s}$-$C^{e2s}$-$A^{m1s}$-$G^{m1s}$-$G^{m1s}$-$A^{e2s}$-$A^{m1s}$-$T^{e2s}$-$CH_2CH_2OH$;

(SEQ ID NO: 6)
(DMD AO06) HO-$C^{e2s}$-$C^{e2s}$-$A^{m1s}$-$T^{m1s}$-$T^{e2s}$-$U^{m1s}$-$G^{m1s}$-$T^{e2s}$-$A^{m1s}$-$U^{m1s}$-$T^{e2s}$-$T^{e2s}$-$A^{m1s}$-$G^{m1s}$-$C^{e2s}$-$A^{m1s}$-$T^{e2s}$-$G^{m1s}$-$CH_2CH_2OH$;

(SEQ ID NO: 7)
(DMD AO07) HO-$G^{m1s}$-$G^{m1s}$-$C^{e2s}$-$T^{e2s}$-$G^{m1s}$-$C^{m1s}$-$T^{e2s}$-$T^{e2s}$-$U^{m1s}$-$G^{m1s}$-$C^{e2s}$-$C^{m1s}$-$C^{m1s}$-$T^{e2s}$-$C^{e2s}$-$A^{m1s}$-$G^{m1s}$-$C^{e2s}$-$CH_2CH_2OH$;

(SEQ ID NO: 8)
(DMD AO08) HO-$G^{m1s}$-$C^{e2s}$-$T^{e2s}$-$A^{m1s}$-$G^{m1s}$-$G^{m1s}$-$T^{e2s}$-$C^{e2s}$-$A^{m1s}$-$G^{m1s}$-$G^{m1s}$-$T^{e2s}$-$G^{m1s}$-$C^{m1s}$-$T^{e2s}$-$T^{e2s}$-$U^{m1s}$-$CH_2CH_2OH$;

(SEQ ID NO: 9)
(DMD AO09) HO-$A^{m1s}$-$C^{e2s}$-$C^{e2s}$-$G^{m1s}$-$C^{m1s}$-$C^{e2s}$-$T^{e2s}$-$U^{m1s}$-$C^{m1s}$-$C^{e2s}$-$A^{m1s}$-$C^{m1s}$-$T^{e2s}$-$C^{e2s}$-$A^{m1s}$-$G^{m1s}$-$A^{e2s}$-$G^{m1s}$-$CH_2CH_2OH$;

-continued (SEQ ID NO: 10)
(DMD AO10) HO-$G^{e2s}$-$G^{e2s}$-$C^{e2s}$-$A^{e2s}$-$T^{e2s}$-$U^{m1s}$-$U^{m1s}$-$C^{m1s}$-$U^{m1s}$-$A^{m1s}$-$G^{m1s}$-$U^{m1s}$-$t^{m1s}$-Te25-$G^{e2s}$-$G^{e2s}$-$A^{e2s}$-$G^{e2s}$-$CH_2CH_2OH$;

(SEQ ID NO: 11)
(DMD AO11) HO-$G^{m1s}$-$G^{m1s}$-$C^{e2s}$-$A^{m1s}$-$T^{e2s}$-$T^{e2s}$-$U^{m1s}$-$C^{e2s}$-$T^{e2s}$-$A^{m1s}$-$G^{m1s}$-$U^{m1s}$-$T^{e2s}$-$T^{e2s}$-$G^{m1s}$-$G^{m1s}$-$A^{e2s}$-$G^{m1s}$-$CH_2CH_2OH$;

(SEQ ID NO: 12)
(DMD AO12) HO-$A^{e2s}$-$G^{m1s}$-$T^{e2s}$-$U^{m1s}$-$T^{e2s}$-$G^{m1s}$-$G^{m1s}$-$A^{e2s}$-$G^{m1s}$-$A^{m1s}$-Tes-$G^{m1s}$-$G^{m1s}$-$C^{e2s}$-$A^{e2s}$-$G^{m1s}$-$T^{e2s}$-$T^{e2s}$-$CH_2CH_2OH$;

(SEQ ID NO: 13)
(DMD AO13) HO-$C^{e2s}$-$T^{e2s}$-$c^{m1s}$-$C^{e2s}$-$T^{e2s}$-$U^{m1s}$-$C^{e2s}$-Ce23-$A^{m1s}$-$T^{e2s}$-$G^{m1s}$-$A^{m1s}$-$C^{e2s}$-$T^{e2s}$-$C^{e2s}$-$A^{m1s}$-$A^{m1s}$-$G^{m1s}$-$CH_2CH_2OH$;

(SEQ ID NO: 14)
(DMD AO14) HO-$C^{e2s}$-$T^{e2s}$-$G^{m1s}$-$A^{m1s}$-$A^{m1s}$-$G^{m1s}$-$G^{m1s}$-$T^{e2s}$-$G^{m1s}$-$T^{e2s}$-$T^{e2s}$-$C^{e2s}$-$T^{e2s}$-$T^{e2s}$-$G^{m1s}$-$T^{e2s}$-$A^{m1s}$-$C^{e2s}$-$CH_2CH_2OH$;

and (SEQ ID NO: 15)
(DMD AO15) HO-$T^{e2s}$-$T^{e2s}$-$C^{m1s}$-$C^{e2s}$-$A^{m1s}$-$G^{m1s}$-$C^{e2s}$-$C^{e2s}$-$A^{m1s}$-$T^{e2s}$-$T^{e2s}$-$G^{m1s}$-$T^{e2s}$-$G^{m1s}$-$T^{e2s}$-$T^{e2s}$-$G^{m1s}$-$A^{m1s}$-$CH_2CH_2OH$, wherein the left side represents the 5' end, and the right side represents the 3' end, A, G, C, U, and T respectively represent adenosine, guanosine, cytidine, uridine, and thymidine in which D-ribofuranose is modified and the carbon atom at the 5'-position is phosphorothioate-bound to the structural unit displayed on the left side, the e2s attached to each nucleotide or nucleoside indicates that D-ribofuranose is 2'-O,4'-C-ethylene-bridged, and the 3'-position binds to the carbon atom at the 5'-position of the nucleotide or nucleoside adjacent to the right side via —OP(═S)(—OH)—O—, the mis attached thereto indicates that D-ribofuranose is 2'-O-methylated, and the 3'-position binds to the carbon atom at the 5'-position of the nucleotide or nucleoside adjacent to the right side via —OP(═S)(—OH)—O—.

11. The method according to claim 9, wherein the oligonucleotide consists of a sequence represented by any one formula selected from GSD AO01 to GSD AO16 below, and the ligand is represented by $X^{18}$ or $X^{20}$ in the following formulas:

(SEQ ID NO: 16)
(GSDAO01) $X^{18}$-$A^{m1s}$-$A^{e2s}$-$g^{m1s}$-$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H;

(SEQ ID NO: 17)
(GSDAO02) $X^{18}$-$A^{e2s}$-$U^{m1s}$-$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1s}$-$C^{e2t}$-H;

(SEQ ID NO: 18)
(GSDAO03) $X^{18}$-$U^{m1s}$-$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{s2s}$-$G^{m1s}$-$C^{e2s}$-$U^{m1t}$-H;

(SEQ ID NO: 19)
(GSDAO04) $X^{18}$-$A^{m1s}$-$A^{m1s}$-$A^{e2s}$-$U^{m1s}$-$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H;

(SEQ ID NO: 20)
(GSDAO05) $X^{18}$-$A^{m1s}$-$A^{e2s}$-$U^{m1s}$-$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1s}$-$C^{e2t}$-H;

(SEQ ID NO: 21)
(GSDAO06) $X^{18}$-$A^{e2s}$-$U^{m1s}$-$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1s}$-$C^{e2s}$-$U^{m1t}$-H;

(SEQ ID NO: 22)
(GSDAO07) $X^{18}$-$A^{m1s}$-$A^{e2s}$-$U^{m1s}$-$C^{m1s}$-$C^{e2s}$-$G^{m1s}$-$A^{m1s}$-$U^{m1s}$-$G^{m1s}$-$G^{m1s}$-$C^{e2s}$-$G^{m1s}$-$A^{m1s}$-$A^{e2s}$-$G^{m1t}$-H;

(SEQ ID NO: 23)
(GSDAO08) $X^{18}$-$A^{e2s}$-$U^{m1s}$-$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2t}$-H;

(SEQ ID NO: 24)
(GSDAO09) $X^{18}$-$U^{m1s}$-$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-Ae25-$G^{m1s}$-$C^{e2s}$-$U^{m1t}$-H;

(SEQ ID NO: 25)
(GSDAO10) $X^{18}$-$A^{m1s}$-$A^{m1s}$-$A^{e2s}$-$U^{m1s}$-$c^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-Gmt-H;

(SEQ ID NO: 26)
(GSDAO11) $X^{18}$-$A^{m1s}$-$A^{e2s}$-$U^{m1s}$-$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-Ae23-$G^{m1s}$-$C^{e2t}$-H1;

(SEQ ID NO: 27)
(GSDAO12) $X^{18}$-$A^{e2s}$-$U^{m1s}$-$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2s}$-$U^{m1t}$-H;

-continued (SEQ ID NO: 28)
(GSDA013) $X^{20}$-$A^{m1s}$-$A^{e2s}$-$U^{m1s}$-$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1t}$-H;

(SEQ ID NO: 29)
(GSDA014) $X^{20}$-$A^{e2s}$-$U^{m1s}$-$C^{m1s}$-$C^{e2s}$-$G^{m1s}$-$A^{e2s}$-$U^{m1s}$-$G^{m1s}$-$C^{m1s}$-$C^{e2s}$-$G^{m1s}$-$A^{m1s}$-$A^{e2s}$-$G^{m1s}$-$C^{e2t}$-H;

(SEQ ID NO: 30)
(GSDA015) $X^{20}$-$A^{m1s}$-$A^{m1s}$-$A^{e2s}$-$U^{m1s}$-$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1t}$-H;

and (SEQ ID NO: 31)
(GSDA016) $X^{20}$-$A^{m1s}$-$A^{e2s}$-$U^{m1s}$-$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2t}$-H, wherein the left side represents the 5' end, and the right side represents the 3' end, A, G, C, U, and T respectively represent adenosine, guanosine, cytidine, uridine, and thymidine in which D-ribofuranose is modified and the carbon atom at the 5'-position is phosphorothioate-bound to the structural unit displayed on the left side, the e2s attached to each nucleotide or nucleoside indicates that D-ribofuranose is 2'-O,4'-C-ethylene-bridged, and the 3'-position binds to the carbon atom at the 5'-position of the nucleotide or nucleoside adjacent to the right side via —OP(═S)(—OH)—O—, the e2t attached thereto indicates that D-ribofuranose is 2'-0,4'-C-ethylene-bridged, and the 3'-position binds to the hydrogen atom at the 3' end via —O—, the mis attached thereto indicates that D-ribofuranose is 2'-O-methylated, and the 3'-position binds to the carbon atom at the 5'-position of the nucleotide or nucleoside adjacent to the right side via —OP(═S)(—OH)—O—, the m1t attached thereto indicates that D-ribofuranose is 2'-O-methylated, and the 3'-position binds to the hydrogen atom at the 3' end via —O—, and $X^{18}$ and $X^{20}$ respectively represent GalNAc units represented by the following formulas, wherein the bond bound to the phosphate group indicates its bonding to the carbon atom at the 5' end of the oligonucleotide to form a phosphodiester bond:

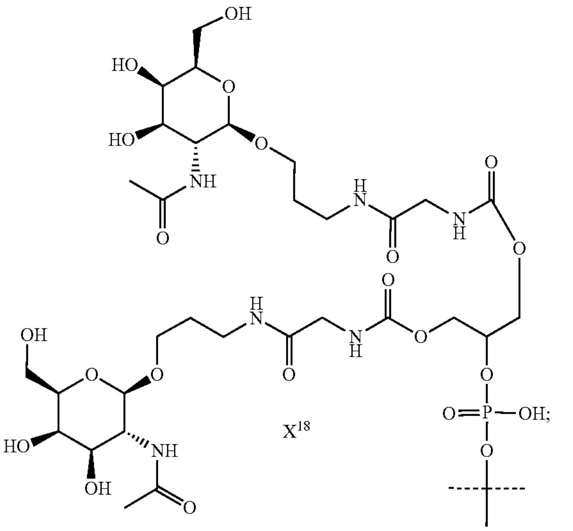

$X^{18}$

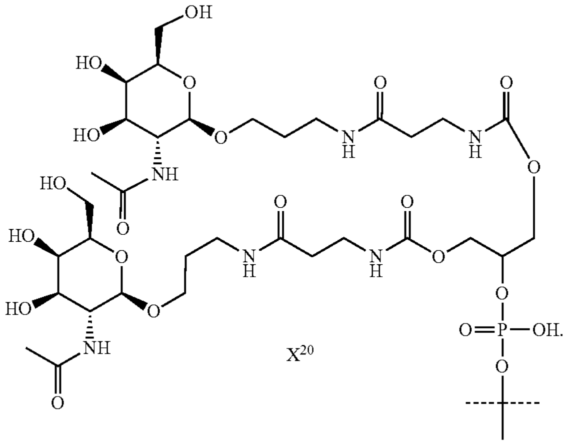

$X^{20}$

12. A method for producing a compound represented by formula (II):

(II)

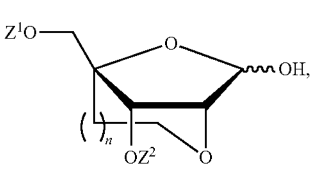

the method comprising:

(i) a step of solvolyzing the acetal moiety of a compound represented by formula (III):

(III)

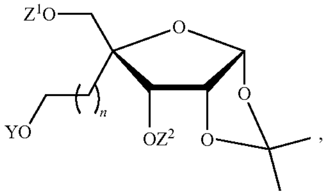

in a lower alkyl alcohol solvent in the presence of an acid catalyst, to deprotect Y;

(ii) a step of cyclizing the diol moiety of the compound represented by formula (IV) obtained in step (i):

(IV)

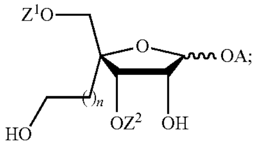

and (iii) a step of hydrolyzing the anomer position of the compound represented by formula (V) obtained in step (ii):

(V)

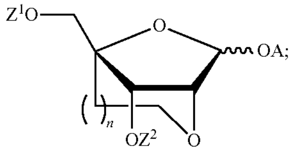

wherein the acid catalyst is sulfuric acid, p-toluenesulfonic acid, or methanesulfonic acid, wherein step (ii) is performed using a trivalent phosphorus reagent and an azodicarboxylate ester, wherein the trivalent phosphorus reagent is triphenylphosphine or tri(n-butyl)phosphine, wherein the azodicarboxylate ester is diethyl azodicarboxylate, diisopropyl azodicarboxylate, or di t-butyl azodicarboxylate, wherein step (iii) is performed using an acid, and wherein the acid is hydrochloric acid, sulfuric acid, trifluoroacetic acid, methanesulfonic acid, or p-toluenesulfonic acid;

wherein:

$Z^1$ and $Z^2$ are identical or different and each represent a protective group for a hydroxy group;

n represents an integer of 0 to 4;

Y represents a methyl group substituted with 1 to 3 aryl groups; a methyl group substituted with 1 to 3 aryl groups in which each aryl ring is substituted with a lower alkyl, lower alkoxy, halogen, or cyano group; a lower alkoxymethyl group; a tetrahydropyranyl group; or a silyl group; and A represents a lower alkyl group.

13. A method for producing a compound represented by formula (VI):

(VI)

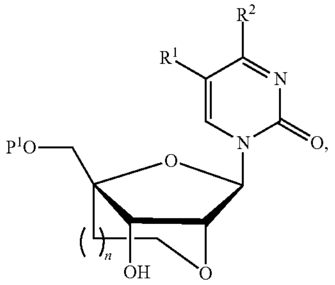

or a salt or a tautomer thereof, the method comprising:

(i) a step of reacting a compound represented by formula (II):

(II)

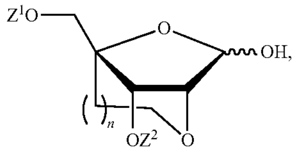

with an activator in a solvent, to convert a hydroxyl group at the 1-position into a group that forms a leaving group;

(ii) a step of reacting the compound represented by formula (VII) obtained in step (i):

(VII)

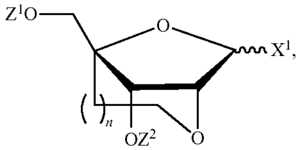

with a compound represented by formula (VIII):

(VIII)

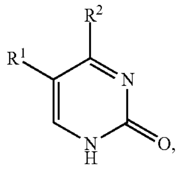

or a salt or a tautomer thereof, in a solvent in the presence of a halogenating agent, to stereoselectively obtain a compound represented by formula (IX):

(IX)

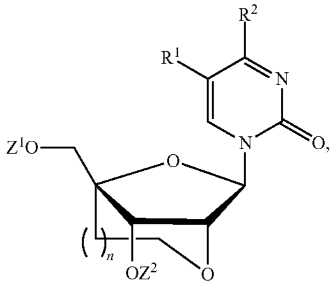

or a salt or a tautomer thereof;

(iii) a step of reacting the compound represented by formula (IX) obtained in step (ii):

(IX)

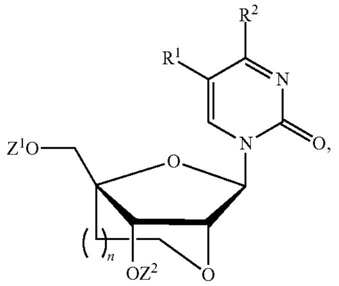

or a salt or a tautomer thereof, with a deprotection reagent for a hydroxyl group in a solvent, to deprotect $Z^1$ and $Z^2$; and (iv) a step of reacting the diol compound obtained in step (iii) or a salt or a tautomer thereof, with a protection reagent for a primary hydroxyl group, to obtain a compound represented by formula (VI):

(VI)

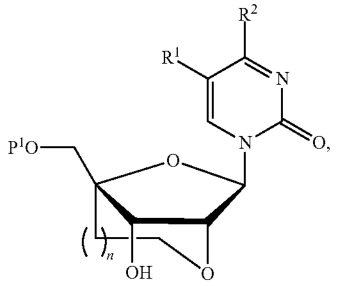

wherein the activator is acetic anhydride, benzoic anhydride, trichloroacetonitrile, carbonyldiimidazole, or diphenyl chlorophosphate, and wherein the halogenating agent is chlorotrimethylsilane, bromotrimethylsilane, or iodotrimethylsilane;

wherein:

$R^1$ represents a lower alkyl group or a hydrogen atom;

$R^2$ represents a hydroxyl group, an amino group, or an amino group protected by an aliphatic acyl group or an aromatic acyl group;

$P^1$ represents a trityl group optionally substituted with 1 to 3 lower alkoxy groups;

n represents an integer of 0 to 4;

$Z^1$ and $Z^2$ are identical or different and each represent a protective group for a hydroxy group; and $X^1$ represents a group that forms a leaving group.

14. A method for producing a compound represented by formula (VI):

(VI)

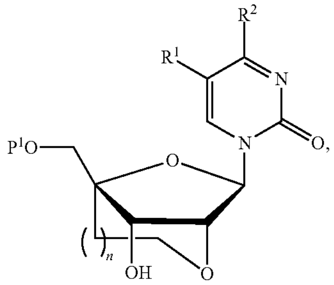

or a salt thereof or a tautomer, the method comprising:

(i) a step of reacting a compound represented by formula (II):

(II)

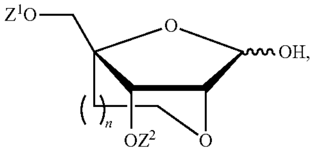

with an activator in a solvent, to convert a hydroxyl group at the 1-position into a group that forms a leaving group;

(ii) a step of reacting the compound represented by formula (VII) obtained in step (i):

(VII)

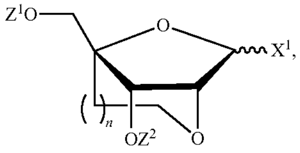

with a compound represented by formula (VIII):

(VIII)

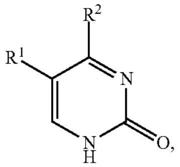

or a salt or a tautomer thereof, in a solvent in the presence of a halogenating agent, to stereoselectively obtain a compound represented by formula (IX):

(IX)

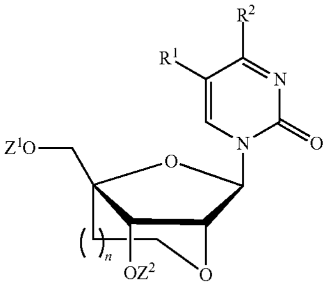

or a salt or a tautomer thereof;

(iii) a step of reacting the compound represented by formula (IX) obtained in step (ii):

(IX)

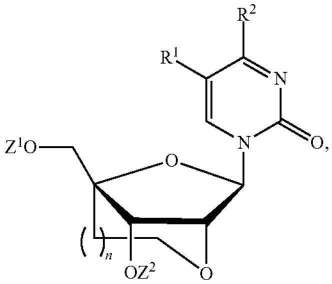

or a salt or a tautomer thereof, with a deprotection reagent for a hydroxyl group in a solvent, to deprotect $Z^1$ and $Z^2$; and (iv) a step of reacting the diol compound obtained in step (iii) or a salt or a tautomer thereof, with a protection reagent for a primary hydroxyl group, to obtain a compound represented by formula (VI):

(VI)

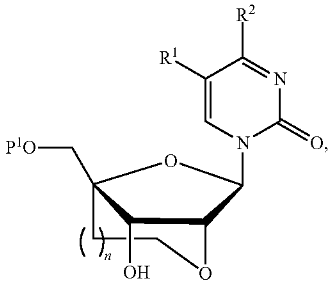

wherein the activator is acetic anhydride, benzoic anhydride, trichloroacetonitrile, carbonyldiimidazole, or diphenyl chlorophosphate, and wherein the halogenating agent is chlorotrimethylsilane, bromotrimethylsilane, or iodotrimethylsilane;

wherein:

$R^1$ represents a lower alkyl group or a hydrogen atom;

$R^2$ represents a hydroxyl group, an amino group, or an amino group protected by an aliphatic acyl group or an aromatic acyl group;

$P^1$ represents a trityl group optionally substituted with 1 to 3 lower alkoxy groups;

n represents an integer of 0 to 4;

$Z^1$ and $Z^2$ are identical or different and each represent a protective group for a hydroxy group; and $X^1$ represents a group that forms a leaving group.

15. A method for producing a compound represented by formula (X):

(X)

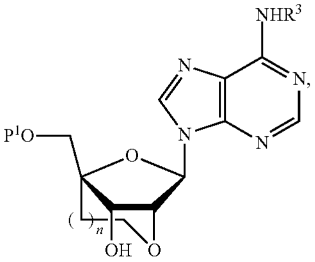

or a salt or a tautomer thereof, the method comprising:

(i) a step of reacting a compound represented by formula (II):

(II)

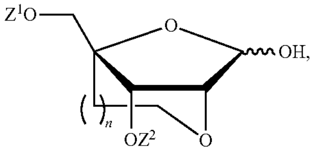

with an activator in a solvent, to convert a hydroxyl group at the 1-position into a group that forms a leaving group;

(ii) a step of reacting the compound represented by formula (XI) obtained in step (i):

(XI)

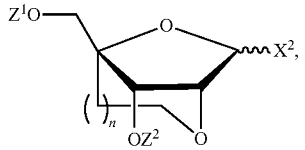

with a compound represented by formula (XII):

(XII)

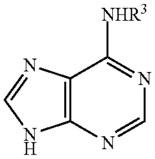

or a salt or a tautomer thereof, in a solvent in the presence of an acid reagent;

(iii) a step of performing isomerization, to stereoselectively obtain a compound represented by formula (XIII):

(XIII)

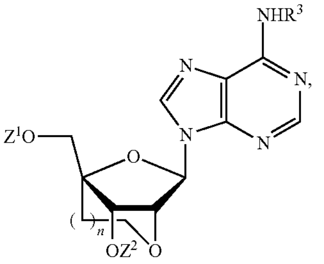

or a salt or a tautomer thereof;

(iv) a step of reacting the compound represented by formula (XIII) obtained in step (iii):

(XIII)

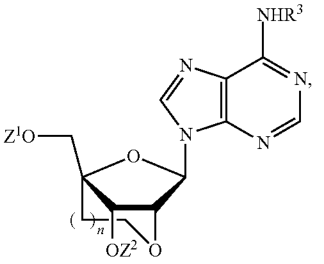

or a salt or a tautomer thereof, with a deprotection reagent for a hydroxyl group in a solvent, to deprotect $Z^1$ and $Z^2$; and (v) a step of reacting the diol compound obtained in step (iv) or a salt or a tautomer thereof, with a protection reagent for a primary hydroxyl group and selectively protecting the primary hydroxyl group, to obtain a compound represented by formula (X):

(X)

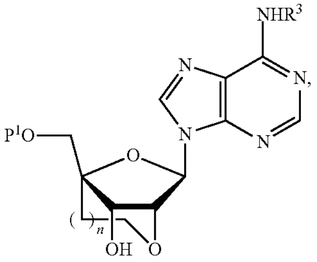

wherein the activator is acetic anhydride, benzoic anhydride, trichloroacetonitrile, carbonyldiimidazole, or diphenyl chlorophosphite, and wherein the acid reagent is trimethylsilyl trifluoromethanesulfonate and trifluoroacetic acid;

wherein:

$R^3$ represents an aliphatic acyl group or an aromatic acyl group;

$P^1$ represents a trityl group optionally substituted with 1 to 3 lower alkoxy groups;

n represents an integer of 0 to 4;

$Z^1$ and $Z^2$ are identical or different and each represent a protective group for a hydroxy group; and $X^2$ represents a group that forms a leaving group.

16. A method for producing a compound represented by formula (XXII):

(XXII)

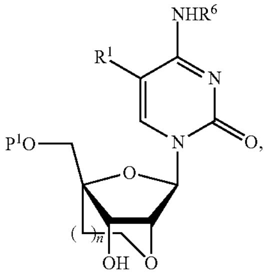

or a salt or a tautomer thereof, the method comprising:

(i) a step of reacting a compound represented by formula (XXIII):

(XXIII)

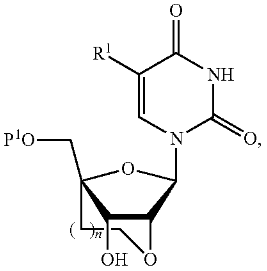

a salt or a tautomer thereof, with a protection reagent for a hydroxyl group in a solvent, to protect the hydroxyl group at the 3-position;

(ii) a step of reacting the compound represented by formula (XXIV) obtained in step (i):

(XXIV)

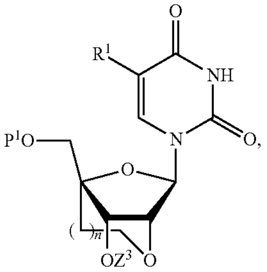

or a salt or a tautomer thereof, with an activator in a solvent in the presence of a base and a catalyst;

(iii) a step of then performing a reaction with an aminating agent, to obtain a compound represented by formula (XXV):

(XXV)

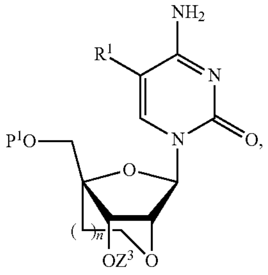

or a salt or a tautomer thereof;

(iv) a step of reacting the compound represented by formula (XXV) obtained in step (iii):

(XXV)

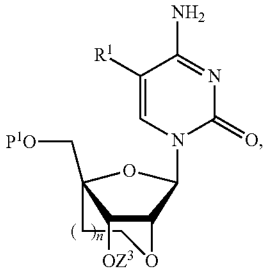

or a salt or a tautomer thereof, with an acylating agent in a solvent, (v) a step of reacting the compound represented by formula (XXVI) obtained in step (iv):

(XXVI)

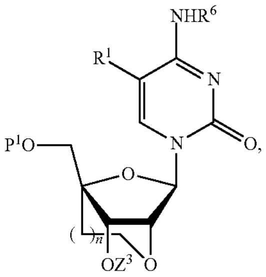

or a salt or a tautomer thereof, with a deprotection reagent for a hydroxyl group and deprotecting only $Z^3$, to obtain a compound represented by formula (XXII):

(XXII)

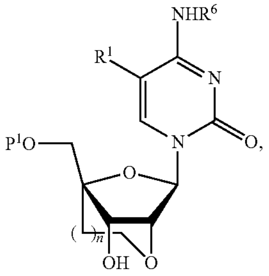

wherein the activator is p-toluenesulfonyl chloride or 2,4,6-triisopropylbenzenesulfonyl chloride;

wherein:

$R^1$ represents a lower alkyl group or a hydrogen atom;

$R^6$ represents an aliphatic acyl group or an aromatic acyl group;

$P^1$ represents a trityl group optionally substituted with 1 to 3 lower alkoxy groups;

n represents an integer of 0 to 4; and $Z^3$ represents an aliphatic acyl group or an aromatic acyl group.

17. A production method comprising the steps of:

reacting a compound represented by formula (XXVII):

(XXVII)

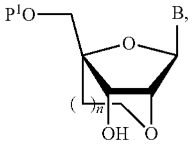

or a salt or a tautomer thereof, with an amidite-forming reagent in a solvent in the presence of an activator and a drying agent, to produce a compound represented by formula (XXVIII):

(XXVIII)

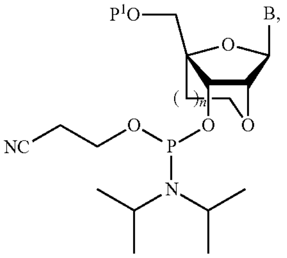

or a salt or a tautomer thereof wherein the activator is 4,5-dicyanoimidazole, wherein the amidite-forming reagent is 2-cyanoethyl N,N,N',N'-tetraisopropyl phosphorodiamidite, and wherein the drying agent is molecular sieve 3A, molecular sieve 4A, or molecular sieve 5A;

wherein:

$P^1$ represents a trityl group optionally substituted with 1 to 3 lower alkoxy groups;

B represents a 2-oxo-pyrimidin-1-yl group optionally having one or more substituents selected from the group α below or a purin-9-yl group;

n represents an integer of 0 to 4; and group α represents a hydroxyl group, a protected hydroxyl group, a lower alkoxy group, a mercapto group, a protected mercapto group, a lower alkylthio group, an amino group, a protected amino group, a lower alkylamino group, a lower alkyl group, or a halogen atom.

18. A production method comprising the steps of:

reacting a compound represented by formula (XXVII):

(XXVII)

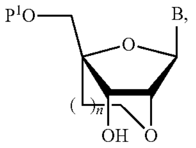

or a salt or a tautomer thereof, with an amidite-forming reagent in a solvent in the presence of an activator and a drying agent, to produce a compound represented by formula (XXVIII):

(XXVIII)

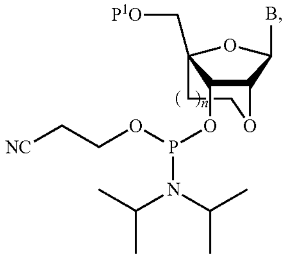

or a salt or a tautomer thereof wherein the activator is 4,5-dicyanoimidazole, wherein the amidite-forming reagent is 2-cyanoethyl N,N,N',N'-tetraisopropyl phosphorodiamidite, and wherein the drying agent is molecular sieve 3A, molecular sieve 4A, or molecular sieve 5A;

wherein:

$P^1$ represents a trityl group optionally substituted with 1 to 3 lower alkoxy groups;

B represents a 2-oxo-pyrimidin-1-yl group optionally having one or more substituents selected from the group α below or a purin-9-yl group;

n represents an integer of 0 to 4; and group α a represents a hydroxyl group, a protected hydroxyl group, a lower alkoxy group, a mercapto group, a protected mercapto group, a lower alkylthio group, an amino group, a protected amino group, a lower alkylamino group, a lower alkyl group, or a halogen atom.

* * * * *